(12) United States Patent
Dikunova-Pertseva

(10) Patent No.: US 12,005,136 B2
(45) Date of Patent: Jun. 11, 2024

(54) METHOD FOR TRANSLUCENT DYEING OF HAIR (VARIANTS) AND COMPOSITION FOR THE IMPLEMENTATION THEREOF

(71) Applicant: Yulia Dikunova-Pertseva, Stavropol (RU)

(72) Inventor: Yulia Dikunova-Pertseva, Stavropol (RU)

( * ) Notice: Subject to any disclaimer, the term of this patent is extended or adjusted under 35 U.S.C. 154(b) by 61 days.

(21) Appl. No.: 17/923,723

(22) PCT Filed: Mar. 15, 2021

(86) PCT No.: PCT/RU2021/050069
§ 371 (c)(1),
(2) Date: Nov. 7, 2022

(87) PCT Pub. No.: WO2021/225471
PCT Pub. Date: Nov. 11, 2021

(65) Prior Publication Data
US 2023/0165775 A1 Jun. 1, 2023

(30) Foreign Application Priority Data
May 6, 2020 (RU) ................................. 2020115433

(51) Int. Cl.
*A61Q 5/10* (2006.01)
*A61K 8/19* (2006.01)
*A61K 8/34* (2006.01)
*A61K 8/65* (2006.01)
*A61K 8/92* (2006.01)
*A61Q 5/02* (2006.01)
*A61Q 5/06* (2006.01)
*A61Q 5/08* (2006.01)

(52) U.S. Cl.
CPC .................. *A61K 8/65* (2013.01); *A61K 8/19* (2013.01); *A61K 8/345* (2013.01); *A61K 8/925* (2013.01); *A61Q 5/02* (2013.01); *A61Q 5/065* (2013.01); *A61Q 5/08* (2013.01); *A61K 2800/262* (2013.01); *A61K 2800/4322* (2013.01); *A61K 2800/884* (2013.01)

(58) Field of Classification Search
CPC . A61K 8/65; A61K 8/19; A61K 8/345; A61K 8/925; A61K 2800/262; A61K 2800/4322; A61K 2800/884; A61K 2800/43; A61K 8/44; A61K 8/00; A61Q 5/02; A61Q 5/065; A61Q 5/08; A61Q 5/10
USPC ............................................................ 8/405
See application file for complete search history.

(56) References Cited

U.S. PATENT DOCUMENTS

| | | | | |
|---|---|---|---|---|
| 4,104,021 A | * | 8/1978 | Lapidus | A61K 8/411 8/429 |
| 6,758,867 B2 | * | 7/2004 | Patel | A61Q 5/02 8/408 |
| 2003/0140428 A1 | * | 7/2003 | Patel | A61Q 5/02 8/408 |
| 2015/0209250 A1 | * | 7/2015 | Massoni | A61K 8/466 8/406 |
| 2017/0239158 A1 | * | 8/2017 | Goutsis | A61K 8/368 |

FOREIGN PATENT DOCUMENTS

RU 2679606 C2 * 2/2019 ............... A61Q 5/10

* cited by examiner

*Primary Examiner* — Eisa B Elhilo
(74) *Attorney, Agent, or Firm* — Nadya Reingand

(57) ABSTRACT

The group of inventions relates to the field of hairdressing and includes a method for the translucent dyeing of hair which is carried out by the step-by-step layered application of requisite compositions onto a strip of hair with mechanical action and constant monitoring of the process, said method comprising preparation of the hair for dyeing and dyeing with a dye which has been diluted with an oxidizing agent, wherein preparation for dyeing is carried out using compositions in the form of diffusions which are a mixture of components in which shampoo is used as an active substance, and dyeing is carried out using diffusions which are a mixture of components comprising an oxidative dye and a low-concentration oxidizing agent. The invention also relates to diffusions for implementing the method.

14 Claims, No Drawings

METHOD FOR TRANSLUCENT DYEING OF HAIR (VARIANTS) AND COMPOSITION FOR THE IMPLEMENTATION THEREOF

FIELD OF THE INVENTION

The claimed invention relates to hairdressing, more specifically, to methods of human hair dyeing in hairdressers or beauty salons.

DESCRIPTION OF THE PRIOR ART

Currently, naturalness and giving them the most natural shade ranks first in popularity in hair dyeing. Moreover, hair should look healthy and alive.

There are known methods of human hair dyeing with dyeing compositions comprising the precursors of oxidizing dyes that are commonly called oxidizable bases. Precursors of oxidizing dyes or oxidizable bases are colorless or mildly dyed compounds which as combined with oxidizing agents can form dyeing elements resulting from oxidative condensation.

It is also known that using such oxidizable bases, it is possible to change the resulting shades, using them in combination with dye-forming substances or color modifiers.

The variety of molecules used at the level of oxidizable bases and dye-forming substances facilitates obtaining a varied color palette.

The so-called "permanent" color achieved thanks to such oxidizing dyes shall meet certain requirements. In particular, it should not have the disadvantages of a toxicological plan, it should provide the shades of desired intensity and have good resistance to external factors (light, weather conditions, washing, permanent treatment, sweating, friction).

Also, dyes should ensure a complete coating of gray hair. Dyes should have, if possible, the least selectivity, i.e. they should facilitate, if possible, minimal color deviations along the whole length of the keratin fiber, which can be unequally sensitive (damaged) in the area between the hair top and hair root.

Oxidative fiber dyeing is done, as a rule, in an alkaline medium in the presence of hydrogen peroxide. However, the use of alkaline media in the presence of hydrogen peroxide has such a disadvantage as a noticeable fiber destruction and a significant hair discoloration, which is not desirable.

The following methods of gradual hair dyeing are known that make dyeing less traumatic.

The method of gradual hair dyeing is known under RF Patent No. 2679606 (Application: 2016134428; IPC A61K 8/22, A61K 8/34, A61K 8/44, A61Q 5/10. Patent holder: COMBE INTERNATIONAL LTD. (US). Published on 12 Feb. 2019)[1], which includes the following stages: a) application of the air-oxidized hair dyeing composition to the hair; b) removal of an air-oxidized hair dyeing composition from the hair immediately after application; and c) repeated Stages a) and b), at intervals. The known method when used daily enables for these compositions to gradually increase the color intensity, as a result of which the consumer can change the frequency of application from daily to weekly or, as soon as the desired color is achieved, apply even less often to maintain color.

The method of permanent hair dyeing with cleansing and minimal damage to the hair is known under U.S. Pat. No. 6,758,867 (Application US20010034511; IPC: A61K8/34, A61K8/41, A61Q5/02. Applicant: UNILEVER HOME & PERSONAL CARE [US]. Published on 31 Jul. 2003) [2]. It deals with a way to achieve a permanent desired change in hair color via the use of compositions for daily hair care. It assumes that an appropriate composition oxidized by air oxygen is applied to the hair, left for a certain time and washed off. Such shampooing procedures will gradually dye hair without damage, for example, due to decreased exposure time. Each subsequent processing will add color until the desired shade is obtained. Depending on the concentration of active agents and the exposure period, the desired shade can be achieved in six to eight treatments. It was found that since any single treatment does not exceed the threshold of irreversible damage, the total damage resulting from multiple treatments is lower than the damage from a single traditional treatment. This process gives the user control over the amount of color applied to one's hair, as well as the ability to stop further application if the first color does not match one's taste. The user also has the opportunity to switch to a different shade immediately, without waiting for six to eight weeks that are recommended for normal procedures. During the usual processing of hair dye, it is not recommended to apply and dye the hair at the same time due to severe damage. In a known method, the desired shade can be achieved in several treatments over a long period of time at home, and not in one visit to a hairdressing salon.

U.S. Pat. No. 4,104,021 is known, revealing a method of hair dyeing in which the shade depth gradually increases with successive procedures (application US20010034511; IPC A61K8/00; A61K8/22; A61K8/23; A61K8/33. Applicant: COMBE INC. Published on 1 Aug. 1978 [3], which discloses a method in which human hair is dyed with successive treatments at selected intervals using oxidation colors (aromatic primary amines and aminophenols) mixed with an oxidizer ($H_2O_2$ or its derivative) during each treatment—the amount of oxidation dye applied during each treatment stays essentially the same, and the amount of oxidizing agent increases from the first to the last treatment to ensure a gradual increase in shade depth. The mixture is left on hair for almost the same period during each treatment, followed by removal by washing off.

The preparations under this invention may also comprise known additives or excipients, such as hair care products, for example, quaternized copolymers of vinyl pyrrolidone, carboxyvinyl polymers and the like, plasticizers, thickeners, substances to improve sliding and moisturizing substances, such as silicone copolymer, foam enhancers, preservatives, perfumes and the like.

The known methods enable for the daily use of these compositions to gradually increase the color saturation, as a result of which the consumer can change the application frequency from daily to weekly or, as soon as the desired color is achieved, and apply even less often to maintain color. Due to gradual manifestation of hair dyeing and further use of formulations to maintain a certain dyeing degree, the advantage can be achieved for growing hair to be practically invisible.

However, in the above-mentioned, as well as other known methods of gradual hair dyeing, the dye is applied to the entire hair shaft without regard for the previously dyed or damaged hair sections. As a result, the applied dye agent either "disappears" on the damaged area and the color is not visible or hardly noticeable, or it is applied to the dyed section and darkens it. Thus, the known methods do not compensate for color fall-outs and hair structure irregularities and do not facilitate getting a smooth color along the entire length of the hair shaft.

In addition, the known methods enable getting the desired shade after a number of applications over a long period of time, and not within a single visit to a hairdressing salon.

Currently, volumetric (3D, spatial) hair dyeing, including lightening (discoloration, highlighting), glazing and multi-dyed dyeing of individual strands (coloring), has become the most popular in the art of hair dyeing. Liquid or paste-like lighteners or dyes are applied directly to the hair section to be dyed along its whole length. After some time, the hair grows back, and the hair root has a color different from the dyed hair section, which makes the hairstyle, sooner or later, less attractive. Despite the fact that hair highlighting and dyeing facilitate "masking" this disadvantage, still, after a while, hair dyeing is inevitable. Both overgrown and previously dyed hair sections that do not require additional dyeing are subjected active agentsing, which unnecessarily injures the hair.

Compositions for simultaneous lightening and dyeing of hair are known, for example, a composition containing acid and basic dyes resistant to discoloration, and a single-stage method for simultaneous lightening and dyeing of hair in one stage according to RF patent No. 2308936 (IPC A61K 8/18 (2006.01) A61Q 5/08 (2006.01) A61Q 5/10 (2006.01). Application 2003130278/15, Patent Holder L'AVAN GUARD INC (US). Published on 27 Oct. 2007) [4]. The invention relates to hair discoloration compositions capable of lightening the hair at a single stage by up to seven tones, while simultaneously giving the hair various shades that can either neutralize the warm shade that occurs during discoloration, or providing the lightened hair with other desirable bright colors.

In the method of simultaneous hair lightening and dyeing at a single stage, according to the invention, a composition is prepared containing a powdered persulfate alkaline discoloration composition that have silicate and/or carbonate salts as a source of alkalinity, and a compatible dye agent that has at least one chromophore. This dye agent contains in ortho- or para-position relative to the chromophore at least one inactivating group selected from nitro-, sulfonic or halogen groups. Besides, it can comprise at least one weakly activating group selected from alkyl groups located in ortho- or para-positions relative to the chromophore. Then, the composition is mixed with hydrogen peroxide solution to obtain a homogeneous cream, and this homogeneous cream is applied to hair for lightening and dyeing. The strands are wrapped in aluminum foil and left in thermostat at 45° C. for 15 minutes.

The well-known one-step method [4] of gradual hair dyeing involves single-layer dyeing that does not enable achieving a smooth color on damaged and/or previously dyed hair.

Hair dyes and hair lighteners are used to make gray hair less noticeable, or active agents hair to the desired color. Hair dyes are 1) temporary dyes (dyeing shampoo, color conditioner, color treatment conditioner, etc.), which are easy to apply; the color persists for a short time; 2) semi-permanent dyes (hair manicure, hair manicure for clean-type hair, etc.) that provide a dyeing effect that can be continuously left due to penetration of acid dye into hair; and 3) permanent dyes, which provide, in essence, a permanent dyeing effect due to the oxidative polymerization of the dye agent inside hair. The specific type of commercially available hair dye is selected depending on the intended use.

Each of these dye types is made with numerous color numbers. Commonly, each dye color is indicated on the package containing the dye, or by means of a strand of a sample of dyed hair.

However, even when the same color dye is used, hair color after dyeing varies significantly depending on the hair color mixture before dyeing.

Dyed hair can be naturally pigmented hair or hair dyed with artificial colors, or a heterogeneous mixture of gray and dyed hair. The known dyeing methods do not facilitate obtaining the exact desired hair color after dyeing.

Therefore, it is difficult to predict the color that will result from hair dyeing, only based on the instructions for the finished dyeing composition or sample strands, and the problem arises that the actual hair color after dyeing differs from the expected color.

The technical result achieved by the claimed method is elimination of the demerits of the known hair dyeing methods and compositions intended for hair dyeing, and obtaining a stable, smooth, predictable color on hair that can be damaged, gray and/or previously dyed, after a single application. This application includes the stage of a gentle hair preparation for dyeing, including alignment by color and quality, neutralization of the lightening background, applying a substrate for the desired color followed by translucent main color hair dyeing of the prepared hair shaft, i.e., by repeated application of thin, transparent layers of the dyeing composition to the hair, layer by layer, color by color, including the necessary subsequent refinement and final glaze coating (lamination).

The technical result is also achieved via the use of compositions for the implementation of the claimed method.

The method of translucent hair dyeing was developed by the author to solve a number of tasks set to the hairdresser-colorist:
1. Dyeing of the previously dyed hair with a minimal damage to hair structure;
2. Hair recovery within the dyeing process with replenishing the missing materials and restoration of broken ties, cuticle closing and giving shine to hair;
3. Dyeing within low, slightly alkaline or slightly acidic pH ranges;
4. 100% fitting into any colors due to the use of coloristic techniques and the ability to shift the color around the color wheel;
5. The predicted color washout from one to 8 months;
6. Enhanced color stability due to four factors:
    i. 6.1. Neutralization of the lightening background;
    ii. 6.2. Dyeing with a elevated color content (the dye agent is added taking into account washing out within the first 1.5-2 weeks);
    iii. 6.3. The extension of pigment attachment area in the destroyed hair cortex (due to recovery procedures before dyeing, within and after it);
    iv. 6.4. The depth of dye penetration and layer-by-layer dyeing;
7. Exclusion of color darkening due to a large percentage of the natural base in dyes and, therefore, an accurate fitting to the tone depth level;
8. Solving the problems of gray hair dyeing;
9. Solving the problems of blonde hair dyeing;
10. The most gentle lightening with lightening products by partial application or total application to the entire hair shaft;
11. Enhanced the color brightness via the use of direct-effect dyes.

The claimed method is suitable for dyeing of any hair type.

DISCLOSURE OF THE INVENTION

The technical result is achieved by implementing the hair dyeing method in a step-by-step and layer-by-layer manner, as the necessary components are applied to the hair shaft with mechanical impact and with a constant process monitoring, including hair preparation for dyeing to obtain a hair shaft aligned along the whole length by quality and color and reduced to a neutral tone, and dyeing with a dye agent diluted with an oxidizer, to obtain the transparency of dye agent layers applied on the hair shaft;

moreover, preparation for dyeing is done using diffusion compositions, being a mixture of components, where shampoo is used as an active agent;

moreover, dyeing is done using diffusion compositions which are a mixture of components containing at least one oxidative dyeing agent and a low concentration oxidizer;

At the same time, hair preparation for dyeing includes the following activities:
- a) Hair cleansing;
- b) Hair shaft alignment by quality and color,
  moreover, hair shaft alignment by quality is done with hair recovery using active agents,
  moreover, alignment by color is done with introducing the missing colors into the damaged hair sections,
  moreover, the lightening background is replenished with pigments of warm shades with simultaneous hair structure recovery;
- c) Hair shaft alignment by neutralizing the resulting lightening background on the hair with the opposite color to obtain a neutral, gray color, for laying out the required color on it with a predicted result;
- d) Applying a color substrate to create a base for the required dye color;

At the same time, dyeing to the desired color includes the following activities:
- e) Applying the composition with the main dye color on the hair as a thin transparent translucent dye layer;
- f) Leaving the hair dye composition on hair;
- g) Removal of hair dye composition from hair after the maturity period;
- h) Visual control of color manifestation;
- i) Hair shaft alignment with color and/or refinement of the result; Repeating the activities sequence, including Steps d), e), g), h), and i);
- l) Final translucent color application;
- m) As soon as the required result is obtained, the compositions applied are washed off from hair, and the hair is restored.

The method is applied using the diffusion compositions below:
- Acid diffusion;
- Lightening diffusion;
- Discoloration diffusion;
- Dyeing diffusion;
- Pre-pigmenting diffusion;
- Lightening and pre-pigmenting diffusion mix;
- Neutralizing diffusion;
- Lightening and neutralizing diffusion mix;
- Artistic diffusion;
- Max-mix diffusion (neutralization+pre-pigmentation+lightening+dyeing);
- Diluted diffusion;
- Diffusion with direct-effect pigments;
- Clay diffusion.

After cleansing the hair to obtain the final color lighter than the natural tone, lightening is done, and then the applied composition is removed.

Hair lightening is done using a discoloration diffusion composition comprising a lightening powder and an oxidizer.

The discoloration diffusion additionally contains liquid amino acids, oil, silicone, and a thickener.

In the discoloration diffusion, the oxidizer is contained in the concentration of 1% to 3%.

Hair lightening is done using a lightening diffusion composition comprising a dye representing special blonds and Tone Depth Level of at least 10 levels, 9% or 12% oxidizer and a shampoo.

Hair lightening is done using a lightening diffusion composition comprising a dye, Tone Depth Level 10, 3% to 12% oxidizer and a shampoo.

The alignment of the hair shaft by quality with hair structure recovery is done with applying gelatin, glycerin, amino acids, collagen, and oils.

Color alignment with warm color pigments with simultaneous hair structure recovery is done with pre-pigmenting diffusion: a warm color mixtone, a warm color dye, a low concentration oxidizer 1% to 2%. The proportions of the oxidizer are selected based on the mixtone density and in an amount that enables dyeing within pH range 4.5 to 6.

A mask was introduced into the composition of the pre-pigmenting diffusion.

Color alignment with warm-color pigments with simultaneous hair structure recovery is done with pre-pigmenting diffusion: dye, water, liquid amino acids, and this diffusion is applied to pre-washed hair after the recovery procedure with a mask. After the exposure, an oxidizer is applied. Then the hair is washed, the recovery procedure is done with a mask again, and, if the color is not sufficient, the pre-pigmentation procedure is repeated with water.

Neutralization of the resulting lightening background is done using a neutralizing diffusion composition comprising a neutralizing dye, a mixtone and 1% to 9% oxidizer.

At the same time, neutralization and lightening of undesirable colors are done using a neutralizing and lightening diffusion composition comprising a neutralizing dye agent of Tone Depth Level 1 to 9, a neutralizing mixtone, special blonds, an oxidizer 4.5% to 12% and a shampoo.

The substrate for creating a base for the desired dyeing color is created using diffusion compositions, while shampoo is used as the active agent of the substrate base.

Hair dyeing is done using a dyeing diffusion composition of a dye agent of Tone Depth Level 1 to 9, 1% to 9% oxidizer and a shampoo.

Hair dyeing is done using a dyeing diffusion composition, which additionally includes liquid amino acids, oil, fish oil, the amount of which depends on the mass of the dye and the desired color.

Hair dyeing is done using a dyeing diffusion composition, which additionally includes mixtones, and 1% to 3% oxidizer.

Hair dyeing is done using a dyeing diffusion composition, which additionally includes silicone and a thickener.

Hair dyeing is done using a dyeing diffusion composition, which additionally includes a shampoo.

Hair dyeing is done using a dyeing diffusion composition comprising a dye agent of Tone Depth Level 1 to 9, water and liquid amino acids.

When dyeing natural hair with darkening, orange or red mixtones are introduced into the dyeing diffusion, which correspond to the lightening background, blue or green mixtones to neutralize the lightening background, a low concentration 1% to 3% oxidizer, and a shampoo.

When dyeing natural hair with darkening, liquid amino acids, oil, silicone, and a thickener are introduced into the dyeing diffusion.

When dyeing natural hair tone-to-tone by dyeing diffusion with oxidative dyes, a composition with a reduced pH is used.

When dyeing natural hair tone-to-tone, a dyeing diffusion with direct-effect pigments is used, comprising direct-effect pigments and an oxidizer.

Tone-to-tone dyeing of natural hair is done with dyeing diffusion with direct-effect pigments, comprising direct-effect pigments, an oxidizer and an oxidative dye.

Neutralizing or pre-pigmenting, or artistic, or diluted diffusions are used to correct the color of dyeing by lasing.

To adjust the color by translucent hair dyeing, a diluted diffusion is used, comprising a dye, an oxidizer of 1%, and a shampoo.

To adjust the dyeing color, a pre-pigmenting diffusion is used, comprising a warm-color dye agent, a mixtone from yellow to purple, 1% to 3% oxidizer, a mask, and a shampoo.

To adjust the dyeing color, a pre-pigmenting diffusion is used, comprising a mixtone from yellow to purple, an oxidizer 1% to 1.5%, a mask, and a shampoo.

To adjust the dyeing color, a pre-pigmenting diffusion is used, comprising a dye, a mixtone, a direct-effect pigment pre-oxidized with 1% to 6% an oxidizer, and a shampoo, and a mask.

To adjust the dyeing color, a pre-pigmenting diffusion is used, comprising a warm-direction dye, a warm-direction mixtone, and water.

To adjust the dyeing color, a neutralizing diffusion is used, comprising a neutralizing dye, a mixtone and 1% to 9% oxidizer.

To adjust the dyeing color, artistic diffusion is used, comprising a mixtone and an oxidizer in a ratio of 1:20.

The completion of dyeing result is done with pre-pigmenting diffusions that do not contain water.

The final glaze coating is done using a diluted diffusion composition comprising mixtones, 1% an oxidizer, and a shampoo, and a mask.

The hair exposure time to the diluted diffusion composition makes 7-25 minutes, while the final color polishing is done with constant mechanical impact with hands, with visual control of color manifestation. The composition is then removed with water, and the hair is washed with shampoo. Finally, a recovery mask with an acidic pH is applied, which is then washed off with water.

The technical result is also achieved by implementing the hair dyeing method according to Option 2 is done in a step-by-step and layer-by-layer manner, as the necessary components are applied to the hair shaft with a mechanical impact and a constant process monitoring, including hair preparation for dyeing to obtain a hair shaft aligned along the whole length by quality and color and reduced to a neutral tone, and dyeing with a dye agent diluted with an oxidizer, to obtain the transparency of dye agent layers applied on the hair shaft;

moreover, preparation for dyeing is done using diffusion compositions, being a mixture of components, where shampoo is used as an active agent;

moreover, dyeing is done using diffusion compositions which are a mixture of components containing at least one oxidative dyeing agent and a low concentration oxidizer;

At the same time, hair preparation for dyeing includes the following activities:
a) Removal of dirt from hair;
b) Removal of cosmetic pigment;
c) Removal of composition from the hair;
d) Hair pH lowering to a more acidic side;
e) Hair shaft alignment by quality and color,
moreover, hair shaft alignment by quality is done with hair recovery using active agents,
moreover, alignment by color is done with introducing the missing colors into the damaged hair sections,
moreover, the lightening background is replenished with pigments of warm shades with simultaneous hair structure recovery;
f) Hair shaft alignment by neutralizing the resulting lightening background on the hair with the opposite color to obtain a neutral, gray color, for laying out the required color on it with a predicted result,
or
g) Hair shaft alignment by re-neutralizing the resulting lightening background;
h) Composition removal with water;
i) Applying a color substrate to create a base for the required dye color;
j) Composition removal with water;
k) Hair recovery with active agents;
l) Dyeing in the desired color, which includes the following actions:
m) Applying the composition with the main dye color on the hair as a thin transparent translucent dye layer;
n) Leaving the hair dye composition on hair;
o) Removal of the hair dye composition from hair after the maturity period;
p) Visual control of color manifestation;
q) Hair shaft alignment with color and/or refinement of the result;
r) Repeating the activities sequence, including Steps in), n), o), p), q);
s) Final translucent color application;
t) As soon as the required result is obtained, the compositions applied are washed off from hair, and the hair is restored.

The method is applied using the diffusion compositions below:
Acid diffusion;
Lightening diffusion;
Discoloration diffusion;
Pre-pigmenting diffusion;
Lightening and pre-pigmenting diffusion;
Neutralizing diffusion;
Lightening and neutralizing diffusion mix;
Dyeing diffusion;
Artistic diffusion;
Max-mix neutralizing, pre-pigmenting, lightening, and dyeing diffusion;
Diluted diffusion;
Diffusion with direct-effect pigments;
Clay diffusion.

The removal of cosmetic pigment is done with acid diffusion, comprising a mixture of shampoo and acid wash in the proportion of 0.5-3.0 parts of shampoo to 3.0-0.5 parts of acid wash with the possibility of repeated application and subsequent rinsing with water.

The removal of cosmetic pigment is done with discoloration diffusion, where the ratio of the amount of lightening powder to the amount of oxidizer is 1 part of the lightening powder to 1 part of oxidizer to 1 part of lightening powder to 200 parts of oxidizer.

The composition of the discoloration diffusion includes thickeners and active agents.

Removal of cosmetic pigment is done with lightening diffusion in the composition: dye special blonde Tone Depth Levels 11, 12, 14, 9% or 12% oxidizer, and a shampoo.

Removal of cosmetic pigment is done with lightening diffusion in the composition: Tone Depth Level 10 series dye, 3% to 12% oxidizer, and a shampoo.

Removal of cosmetic pigment by acid diffusion is done before applying discoloration or lightening diffusions.

Removal of cosmetic pigment by acid diffusion is done before and after the application of discoloration or lightening diffusions.

Removal of cosmetic pigment by acid diffusion is done after application of discoloration or lightening diffusions.

The removal of cosmetic pigment is done using clay diffusion comprising: clay, water brought to a boil, glycerin; clay diffusion is used before discoloration diffusion.

A nourishing mixture comprising gelatin, glycerin, amino acids, collagen, and oils is used to align the hair shaft by quality.

Color alignment with warm color pigments with simultaneous hair structure recovery is done with pre-pigmenting diffusion comprising: warm color mixtone, warm color dye, low concentration oxidizer 1% to 2%, while the oxidizer proportions are selected based on the mixtone density and in an amount that enables dyeing within pH range 4.5 to 6.

A mask is introduced into the composition of the pre-pigmenting diffusion.

Color alignment with warm-color pigments with simultaneous hair structure recovery is done with pre-pigmenting diffusion comprising: a dye agent, water, and liquid amino acids. The specified diffusion is applied to pre-washed hair after the recovery procedure with a mask, and after exposure, an oxidizer is applied; then, the hair is washed, the recovery procedure is done with a mask once again, and, if there is not enough color, repeat the pre-pigmentation procedure with water.

The hair shaft alignment by neutralizing the resulting lightening background is done using neutralizing diffusion, taking into account the lightening background of the cosmetic base and the natural hair base.

The method uses neutralizing diffusion comprising: a light-tone dye Tone Depth Levels 9 or 10, a neutralizing color mixtone, 1% to 9% oxidizer, and a shampoo. The neutralizing diffusion is performed with a large number of mixtones and with a smaller amount of dye agent.

The method uses neutralizing aqueous diffusion comprising: a neutralizer dye, a mixtone, water, and liquid amino acids.

The hair shaft alignment with re-neutralization of the lightening background—hair oversaturation with neutralizing colors, is done using diluted diffusion, comprising: a mixtone, an oxidizer, and a shampoo.

The hair shaft alignment with re-neutralization of the lightening background—hair oversaturation with neutralizing colors, is done using diluted diffusion, comprising: a mixtone and an oxidizer.

The hair shaft alignment with color is done using the composition of the base-substrate comprising: a dye or a mixtone and a dye, or a dye and a mixtone with an oxidizer, as well as active agents—a shampoo and/or a mask, and/or a thickener; at the same time. Besides, a dye agent of the tone depth level with a low percentage of oxidizer 1%-2% is used. The composition of the substrate is applied to hair by a thin layer; it is left and washed off. In case of color irregularity or an undesirable shade, the application of a substrate layer to the dense hair with composition adjusted, followed by leaving for some time and rinsing until the desired smooth color is obtained along the entire length of the hair shaft.

Hair dyeing is done using dyeing diffusion comprising: a dye agent of the main color Tone Depth Level 1 to 9, 1% to 9%, an oxidizer and a shampoo.

Hair dyeing is done using dyeing diffusion, which additionally includes active agents: liquid amino acids, oil, and fish oil in amounts depending on the mass of the dye agent and the desired color.

Hair dyeing is done using dyeing diffusion, which additionally includes mixtones, and an oxidizer in a concentration of 1% to 3%.

Hair dyeing is done with dyeing diffusion, which additionally includes silicone and a thickener.

Hair dyeing is done with dyeing diffusion, which additionally includes shampoo.

Dyeing is done with dyeing diffusions with water comprising: the main color dye agent is 1 to 9 Tone Depth Levels, water, and liquid amino acids.

The refinement of the color after dyeing is done with artistic diffusion comprising: a dye agent, an oxidizer, and a shampoo.

The completion of dyeing result is done with pre-pigmenting diffusions that do not contain water.

The final color glaze coating is done using a diluted diffusion composition comprising mixtones, 1% oxidizer, a shampoo, and a mask.

The hair exposure time to the diluted diffusion composition makes 7-25 minutes, while the final color polishing is done with constant mechanical action with hands, with visual control of the color manifestation; removal of the composition with water and washing with shampoo; at the end of the process, a recovery mask with an acidic pH is applied, which is then washed off with water.

Hair recovery is done with active agents such as emulsifiers, masks, various oils including jojoba and linseed, amino acids, glycerin, acids, and thickeners.

The technical result is also achieved by implementing the hair dyeing method according to Option 3 is done in a step-by-step and layer-by-layer manner, as the necessary components are applied to the hair shaft with a mechanical impact and a constant process monitoring, including hair preparation for dyeing to obtain a hair shaft aligned along the whole length by quality and color and reduced to a neutral tone, and dyeing with a dye agent diluted with an oxidizer, to obtain the transparency of dye agent layers applied on the hair shaft;

moreover, preparation for dyeing is done using diffusion compositions, being a mixture of components, where shampoo is used as an active agent;

moreover, dyeing is done using diffusion compositions which are a mixture of components containing at least one oxidative dyeing agent and a low concentration oxidizer;

At the same time, hair preparation for dyeing includes the following activities:
    a) Hair cleansing;
    b) Hair loosening;
    c) Removal of the composition from hair with water;
    d) Making a substrate for gray hair,
    e) Removal of the composition in the sequence: a shampoo, water, and a mask application,
    f) Dyeing in the desired color, which includes the following actions:
    g) Applying the composition with the main dye color on the hair as a thin transparent translucent dye layer;

h) Removal of the composition in the sequence: shampoo, water;
i) Color adjustment;
k) Removal of the composition in the sequence: shampoo, water;
l) Hair recovery with active agents.

The method is applied using the diffusion compositions below:
Acid diffusion;
Lightening diffusion;
Discoloration diffusion;
Dyeing diffusion;
Pre-pigmenting diffusion;
Lightening and pre-pigmenting diffusion mix;
Neutralizing diffusion;
Lightening and neutralizing diffusion mix;
Artistic diffusion;
Max-mix neutralizing, pre-pigmenting, lightening, and dyeing diffusion;
Diluted diffusion;
Diffusion with direct-effect pigments;
Clay diffusion.

Hair loosening is done simultaneously with pre-pigmentation, and before dyeing in the desired color, hair recovery is done with active agents.

Hair loosening is done simultaneously with the substrate, including neutralization and pre-pigmentation.

Hair cleansing by removing direct-effect pigments or plant dyes is done with clay diffusion: clay diluted in hot water, glycerin, with preliminary application of alcohol to dry hair.

Hair loosening is done with lightening diffusion.

Hair loosening is done with lightening diffusion: a dye agent, which is a special blonde of Tone Depth Level 10, an oxidizer, and a shampoo.

Loosening with lightening is done with lightening diffusion: a dye agent, which is a special blonde of Tone Depth Levels 11, 12, 14, 12% or 9% oxidizer, and a shampoo.

Loosening with Lightening is done with lightening diffusion: Tone Depth Level 10 series dye, 3%-12% oxidizer, and a shampoo.

Simultaneous lightening with pre-pigmentation is done with lightening and pre-pigmenting diffusion: a special blonde of Tone Depth Levels 11, 12, 14, a warm-color dye agent, a warm-color mixtone, 12% or 9% oxidizer, and a shampoo.

Simultaneous loosening with pre-pigmentation is done with lightening and pre-pigmenting diffusion: a dye agent of Tone Depth Level 10, a dye agent of Tone Depth Level 5 to 9, a mixtone, 3%-12% oxidizer, and a shampoo.

The loosening of gray hair by lightening diffusion simultaneously with a neutralizing-pigmenting substrate is done with diffusion: a dye agent of Tone Depth Level 10 and a special blonde of Tone Depth Levels 11, 12, 14, a warm-color mixtone, a mixtone to neutralize the background of natural hair lightening, 3% to 12% oxidizer, and a shampoo.

The substrate for gray hair is done with diffusion: a main color dye, a neutralizing mixtone, a pre-pigmenting mixtone, an oxidizer 1% to 12%, and a shampoo.

Hair dyeing is done with dyeing diffusion: a main color dye, a warm-color mixtone, a mixtone of neutralizing effect, and an oxidizer.

For hair dyeing with 40-60% of gray hair, a double amount of warm color is added to the dyeing diffusion, while a dye of the natural series Tone Depth Level 7.0-1.0 is added.

When the amount of gray hair gets closer to 60%, a brown-red color is added to the dyeing diffusion.

Hair dyeing with 100% gray is done with lightening, pre-pigmenting and dyeing diffusion: a dye agent of Tone Depth Levels 10-12, a warm-color mixtone, 12% oxidizer, and a shampoo.

Hair dyeing is done with dyeing diffusion with water: a main color dye, water, and liquid amino acids.

Color refinement is done with diffusions: artistic diffusion, diluted diffusion, diffusion with direct-effect pigments.

The color refinement is done with artistic diffusion: mixtones and 1% to 3% oxidizer.

Color refinement is performed with diluted diffusion: a dye agent, a mixtone, an oxidizer, and a shampoo.

Color refinement is performed with diluted diffusion: a dye agent and an oxidizer.

Color refinement is done with diffusion with direct-effect pigments: direct-effect pigments and an oxidizer.

Color refinement is done with diffusion with direct-effect pigments: direct-effect pigments and an oxidative dye.

Color refinement is done with diffusion with direct-effect pigments: direct-effect pigments, an oxidizer, an oxidative dye, and a shampoo.

Hair structure recovery is done with applying gelatin, glycerin, amino acids, collagen, oils and other active agents.

Diffusion compositions for hair dyeing according to the invention include:

Acid diffusion comprising: a shampoo and acid wash in the proportion of 0.5-3.0 parts of shampoo to 3.0-0.5 parts of acid wash;

Lightening diffusion comprising: a dye agent, an oxidizer, and a shampoo;

Discoloration diffusion comprising: 1 part of lightening powder: 1 part of oxidizer to 1 part of lightening powder to 200 parts of oxidizer;

Dyeing diffusion comprising: a dye agent of Tone Depth Levels 1 to 9, 1% to 9% oxidizer, and a shampoo, or a dye agent, 1% to 9% oxidizer, amino acids, oil, fish oil, or a dye agent+water+liquid amino acids;

Pre-pigmenting diffusion comprising: a warm-color dye agent, a
  mixtone, an oxidizer, a shampoo, and a mask or
  a mixtone, an oxidizer, a mask, and a shampoo,
  or a warm-color dye agent, a mixtone, a direct-effect pigment, an oxidizer, a mask, and a shampoo,
  or a warm-color dye agent, a warm-color mixtone, water, or a warm-color dye agent, a mixtone from orange to fuchsia, an oxidizer, and a shampoo;

Lightening and pre-pigmenting mix diffusion comprising: a dye agent, a mixtone, an oxidizer, and a shampoo;

Neutralizing diffusion comprising: a neutralizing dye, a mixtone, and 1% to 9% oxidizer;

Lightening and neutralizing diffusion comprising: a neutralizing a dye agent of Tone Depth Levels 1 to 9, a neutralizing mixtone, special blonds of Tone Depth Levels 10, 11, 12, 14, 4.5% to 12% oxidizer, and a shampoo;

Artistic diffusion comprising: a mixtone, an oxidizer in the ratio of 1:10; moreover, the oxidizer should be 1% to 3%;

Max-mix neutralizing, pre-pigmenting, lightening, dyeing diffusion comprising: a dye agent for loosening gray hair, a dye for pre-pigmentation of gray hair, a mixtone for neutralizing the color of natural hair, a basic tone, mixtones for color leveling and/or adding, an oxidizer, and a shampoo;

Diluted diffusion comprising: a dye agent, a mixtone, an oxidizer, and a shampoo; or a dye agent, an oxidizer; or a mixtone and an oxidizer;

Diffusion with direct-effect pigments comprising: direct-effect pigments, an oxidizer or additionally an oxidative dye or a shampoo;

Clay diffusion comprising: clay, hot water, and glycerin.

Terms and Definitions

Active agents—detergent surfactants, emulsifiers, a mask, various oils (jojoba, linseed), amino acids, liquid and dry solutions, glycerin, acids, and thickeners.

An oxidizer—the present invention refers to a mixture comprising hydrogen peroxide (oxide), a catalyst, buffer components, fragrances, preservatives, and thickeners. The oxidizer percentage specifies the content of oxide (hydrogen peroxide) in it, i.e. 3% oxidizer (corresponds to 10 vol) means 3% content of oxide (hydrogen peroxide).

Oxide is hydrogen peroxide comprised in an oxidizer.

Dyeing composition is a mixture comprised in a cream or oil base, it includes dyes and various substances: alkali, acids, oils, emulsifiers, etc.

A mixture is a system comprising two or more substances (mixture components). A homogeneous mixture is called "a solution" (gas, liquid or solid), and an inhomogeneous one is called "a mechanical mixture". In a mixture, the initial baseline substances are included unmodified.

Diffusions in this method of translucent hair dyeing are compositions intended for gradual gentle hair dyeing and achieving the necessary level of hair tone depth by repeatedly applying dyes and their penetration to a certain hair depth.

Dye agents are organic compounds used for hair dyeing. In such dyes, brown color prevails.

Pigments are substances that can give different bodies a particular color.

Direct-effect pigments are applied directly to hair and do not require mixing with an oxidizer or a developer. According to pH level (a measure expressing product acidity), direct-effect pigments are qualified slightly acidic products and are considered safe for hair and scalp;

A mixtone is a dye in which the concentration of pure colors prevails (blue, green, red, yellow, etc.);

An oxidizing dye is a dye that comprises a pigment in its composition, the color of which is manifested only via oxygen;

Permanent oxidative dyes are dye agents resistant to wear;

A mask is an intensive hair cream.

A classic dyeing method is a dyeing method commonly used in hairdresser's and beauty salons.

A tone depth level (TDL) is the level of hair lightness. In hairdressing, there are 14 tone depth levels, ten tone depth levels of them (1-10) are for natural hair. Hereinafter, Tone Depth Level numbers are also called "rows". Tone Depth Levels 11-14 are special discoloration rows intended mainly to lighten the pigment.

Special blonds are dyes being a part of lightening diffusions. Tone Depth Levels 12-14 are a special series, intended rather to lighten the pigment in hair than active agents it. These dyes first lighten and then dye. Dyes with Tone Depth Level less than 11 and 10 can also be treated as lightening dyes.

Non-special blonds 9, 8, 7, 6, 5, 4, 3, 2, 1. Row 5 is more intended to dye, lightening will be secondary.

Re-pigmentation or pre-pigmentation is adding warm-color pigments to the hair shaft.

Neutralization is converting any color into neutral gray, by adding colors opposing each other in the color wheel.

Wearability of dyeing is its durability, the ability not to wear out.

The natural base is the tone level depth (lightness) of natural hair and also the amount of pigment that is part of hair, its amount varies genetically in each person.

The measurement units used in this method for composition components: for powdered—grains (g); for liquid—milliliters (ml); for creamy components—centimeters (cm).

All components included in the diffusion compositions have a different physical state (powder, liquid, cream), structure, density and viscosity. They are commercially available in different factory packaging. In practical work, it is not convenient to make compositions of them in the same measurement units. In addition, in salons they are used in factory packaging: dye agents are creams in tubes, the product is extracted from them shaped as a "strip". It is easily measured in length units, for example, in centimeters (hereinafter abbreviated as "cm").

The powder is easier to measure in weight units—grains (hereinafter—"g").

Liquids are manufactured in vials, often with measuring caps, they are easier to be measured in units of volume—milliliters (hereinafter—"ml").

DETAILED DESCRIPTION OF THE EMBODIMENT

1. Definition of Translucent Hair Dyeing Method (THD Method)

The method of translucent hair dyeing (THD method) assumes application of a dyeing mixture on hair by thin, transparent layers, layer by layer, "color by color", to achieve a stable result of hair dyeing and for 100% fitting into colors.

Glazing layering is known as a dyeing technique. The layering technique in dyeing means that each subsequent transparent layer of dye is applied onto a previously dried layer. The more such layers, the more expressive the dyeing texture becomes in its diversity. It is this complex (textured and color) combination of all applied layers that causes emergence of a special coloristic effect that gives the finished product its volume and shine.

In the claimed translucent hair dyeing method, a dye agent is diluted with an oxidizer to obtain the transparency of the applied dye layer on the hair shaft. The dye layers should be applied to the prepared hair shaft, aligned in quality and color, and brought to a neutral tone.

The method enables you to improve the structure and avoid damage to hair by effectively adding the active agents.

The claimed translucent hair dyeing method is suitable for any hair type, because it is adjustable.

The author has identified the components facilitating the impact on the dyeing process and obtaining the desired color.

The main method components:
1) a shampoo;
2) a mask (for hair);
3) an oxidizer;
4) a dye agent;
5) a mixtone-type dye agent;
6) a pigment-type dye agent of direct-effect;
7) thickeners for adding viscosity;
8) acids;
9) active additives;
10) water;
11) temperature;

12) exposure time;
13) the amount of color (any type of dye);
14) mechanical impact.

Below is a more detailed description of each of the components of the claimed method.

1) Shampoo:
   affects the penetration depth of the dye pigment into the hair cortex (acts as a transporter, delivers substances deeper into the hair);
   dilutes the color density quite strongly due to a more soapy mixture, the amount of the mixture when applied to the hair decreases significantly;
   the soap content of the composition makes it easy to apply.
2) Hair mask (emulsifiers, oils, keratin, wheat proteins, silk, acids, waxes)
   affects pH of the dye agent;
   affects the mixture density (consistency);
   affects the dye fat content (makes the dye more enriched with the components that are in the mask);
   the dye penetrates less deeply into the cortex.
3) An oxidizer, an oxide:
   the main color developer;
   the main color diluent. It is advisable to add more oxide parts, rather than shampoo, because the oxidizer has an acidic pH, which is of great importance in this method;
   mixture acidifier (the more oxide parts, the more acidic is pH).
4) Dye agent:
   the main product when brown (natural) color is added;
   dyeing basis;
   the main alkaline product;
   the main product in classic and translucent natural hair dyeing;
   the main product when black color is added;
   makes it easier to fit into the desired tone depth levels (i.e. lightness levels).
5) Mixtone-type dye agent:
   the main component to cater for creating pure and intensive colors;
   basic color concentrate;
   facilitates dramatic palette colors' changing and shifting them to any color direction.
6) Direct effect pigments:
   make any dyeing brighter (i.e. they are the brightness basis);
   enable the color to be washed cleaner, as the molecule chemical composition of these pigments makes the color more stable during the oxidation process.
7) Viscosity (thickeners):
   prevents the dye from penetrating too deeply, i.e. modifies the penetration depth;
   enables you to put more pigments on one area;
   enables improving the stability of the lightening reaction;
   slows down slightly the chemical lightening process;
   enables the dye to almost not mix with another dye lying deeper on hair.
8) Acids:
   facilitate influencing pH of the reaction;
   reduce the aggressiveness of alkaline effect on hair;
   reduce the lightening process;
   partially neutralize the ammonia content of the dye agent.
9) Active additives:
   dilute the pigment (color);
   have been created to improve the dyeing composition quality (the addition of proteins, oils and various silicones enriches the dyeing composition content);
   affect pH;
   restore the hair structure (for example, amino acids re-build connections; fill holes; add components that build the hair (lipids, amino acids, moisture)).
10) Water:
    acts as a reaction conductor;
    dilutes the pigment;
    enables the hair to be soaked in dye in case of "dye+water" dyeing;
    makes dyeing more natural (transparent);
    reduces the aggressive impact on the hair;
    promotes better distribution of the dye;
    improves color fastness;
    increases the conductivity of hair care components.
11) Temperature:
    accelerates the lightening and dyeing reaction;
    improves the interaction between substances (components).
12) Exposure time:
    affects the color transparency in the end (the resulting color is dense or transparent);
    affects the lightening degree (stronger or weaker);
    affects color stability (the longer is the exposure time, the more persistent is the color).
13) Color quantity:
    it is an extremely important parameter in creating a color, as it affects the degree of color dilution, and the kind of dye to be applied;
    the lower is the Tone Depth Level, for example 1, 2, 3, 4, 5 (from dark to light), the less the alkaline agent content is in dyes, as it is not intended for intensive lightening, its purpose is to slightly highlight and arrange the pigment;
    Tone Depth Levels 5, 6, 7, 8, 9, 10 go the same way from a darker level 5 to a lighter 10. The increase in lightness is directly proportional to the amount of alkali in dyes, because Tone Depth Level 10—the light level—is intended for a greater lightening of natural hair.
    Tone Depth Levels (rows) 11, 12, 14 are special discoloration rows intended mainly to lighten the pigment.
14) Mechanical impact:
    it is a mechanical impact with hands on liquid compositions and semi-solid products, which ensures mass transfer and chemical interaction of atoms and molecules. For example, it is possible to "push" a large substance molecule, for example, of a pigment, etc., deeper into the hair cortex or to make the dye more resistant by forcibly penetrating it deeper into the cortex and filling in areas of damage.

2. Diffusion Compositions Used in the Claimed Method

To eliminate the disadvantages of commonly used commercial products and methods intended for hair dyeing, this invention offers diffusion compositions used to implement the hair dyeing method of the present invention.

The claimed diffusions enable layer-by-layer application of dyeing compositions. Diffusions, unlike those commonly used in classical dyeing products, contain less color or more, a pure or muted tone (i.e. adjustable) and a lower pH. Most importantly, the consistency of diffusions enables the dye and the dye care to penetrate deeper into hair layers, which classical products are not able to do. The classic mixture penetrates deeply only with alkali, which destroys the hair. Diffusion penetrates into the hair and restores it, and stains it, and enables you to see the color movement on the hair, i.e. the color change over time during the dyeing process.

Diffusions enable hair to be dyed at different penetration depths, regulate pH or viscosity of the dyeing composition.

In the claimed method, various types of diffusion compositions are used:
1. Acid diffusion.
2. Lightening diffusion.
3. Discoloration diffusion.
4. Dyeing diffusion.
5. Pre-pigmenting diffusion.
6. Lightening and pre-pigmenting diffusion mix.
7. Neutralizing diffusion.
8. Lightening and neutralizing diffusion mix.
9. Artistic diffusion.
10. Max-mix diffusion (neutralization+pre-pigmentation+lightening+dyeing).
11. Diluted diffusion (prepared for the substrate or to add a color nuance).
12. Diffusion with direct-effect pigments.
13. Clay diffusion.

The above compositions are intended to gradually achieve the necessary tone level and hair color in preparation or within translucent dyeing process until the required outcome is achieved.

Diffusion Types

TABLE 1

| Item No. | Diffusion | Composition | Use |
|---|---|---|---|
| 1 | Acid diffusion | Shampoo and acid wash in proportion of 0.5-3.0 parts of shampoo to 3.0-0.5 parts of acid wash. | Removal of cosmetic pigments; special blonds and Tone Depth Levels 1-10 |
| 2 | Lightening diffusion | Dye + oxide + shampoo | For lightening natural hair and with a cosmetic base of at least Tone Depth Level 7. |
| 2.1 | Lightening diffusion Type 1 | Dye + special blonde TDL 11, 12, 14 + oxide 12% or 9% + shampoo | For lightening natural hair; For lightening a cosmetic base of at least TDL 7; for a mild lightening effect; for gray hair loosening; for natural base loosening. |
| 2.2 | Lightening diffusion Type 2 | Dye TDL 10 + 3%-12% oxide + shampoo | For lightening natural hair; For lightening a cosmetic base of at least TDL 7; For a mild (1-1.5 tone up) lightening effect; For gray hair loosening; For natural base loosening. |
| 3. | Discoloration diffusion | 1 part of lightening powder: 1 part of oxide up to 1 part of lightening powder: 200 parts of oxide. | Lightening of natural hair; removal of cosmetic pigments |
| 3.1 | Mix 1 | Lightening powder + over 6% oxidizer + liquid amino acids + oil + silicone + thickener | |
| 3.2 | Mix 2 | Lightening powder + over 3% oxidizer + liquid amino acids + oil + silicone + thickener | |
| 3.3 | Mix 3 | Lightening powder + over 2% oxidizer + liquid amino acids + oil + silicone + thickener | |
| 3.4 | Mix 4 | Lightening powder + over 2% oxidizer + liquid amino acids + oil + silicone + thickener | |
| 4 | Dyeing diffusion | | For a full, resistant dyeing and |
| 4.1 | Type 1. Dyeing diffusion with shampoo | Any dye (Dye agent TDL 1 to 9) + oxidizer (1% to 9%), in the ratio of dye: oxidizer (1:2 to 1:6) + shampoo (2 to 300 ml). | as a substitute of classic dyeing with improved hair quality and minimal hair damage |
| 4.2 | Type 2. Dyeing diffusion with mixture enrichment without water | Dye oxidizer (in the proportion as specified by the manufacturer) + oxidizer 1% to 9% + amino acids, oil, fish oil | |

TABLE 1-continued

| Item No. | Diffusion | Composition | Use |
|---|---|---|---|
| 4.3 | Type 3. Dyeing diffusion with water | Dye + water + liquid amino acids. The ratio of the dye to water is 1:1 to 1:20, where 20 are parts of water + amino acids 1 part to 5 parts. | |
| 5 | Pre-pigmenting diffusion | | To add a warm pigment to hair cortex; To improve hair quality; |
| 5.1 | Pre-pigmenting diffusion Type 1 | Warm color dye + mixtone from yellow to purple + oxidizer + shampoo + mask | For pre-pigmentation of previously discolored hair; For hair recovery; For hair darkening. |
| 5.2 | Pre-pigmenting diffusion Type 2 | Mixtone + oxidizer + mask + shampoo | To add a warm pigment to the hair cortex; To improve hair quality |
| 5.3 | Pre-pigmenting diffusion Type 3 | Warm color dye + mixtone + (direct-effect pigment - optionally) + oxidizer + mask + shampoo | To add a warm pigment to the hair cortex; To improve hair quality |
| 5.4 | Pre-pigmenting diffusion Type 4 | Warm color dye + mixtone (warm color) + water | To add a warm pigment to the hair cortex; To improve hair quality |
| 5.5 | Pre-pigmenting diffusion Type 5 | Warm color dye + mixtone from orange to fuchsia + oxidizer + shampoo | For gray hair, loosening gray hair and pre-pigmentation of gray hair; For loosening the natural base; For vitreous hair type, for blonde hair wherein the pigment has been removed by lightening; For pre-pigmentation of previously lightened hair; For hair recovery; For hair darkening. |
| 6. | Lightening and pre-pigmenting diffusion | | For lightening and pre-pigmenting of gray and natural hair |
| 6.1 | Lightening and pre-pigmenting diffusion Type 1 | Dye + mixtone + oxidizer + shampoo | For loosening gray hair and natural base and simultaneous pre-pigmentation |
| 6.2 | Lightening and pre-pigmenting diffusion Type 2 | Dye (less alkaline than in Type 1) + oxidizer + shampoo. | To raise one tone up or loosen gray hair, when lightening is undesirable |
| 7 | Neutralizing diffusion | Neutralizing dye + mixtone + 1% to 9% oxidizer | To neutralize the background lightening of the natural base; To neutralize cosmetic colors; |
| 8 | Lightening and neutralizing diffusion | Neutralizing dye agent TDL 1 to 9 + neutralizing mixtone + special blonds (TDL (rows) 11, 12, 14 or 10) + sufficiently high 4.5% to 12% oxidizer + shampoo | To simultaneously lighten and neutralize unwanted color; For natural hair dyeing; For using when dyeing the roots of natural hair; For previously dyed hair that has an undesirable shade, and there is no desire to darken it. |
| 9 | Artistic diffusion | Mixtone: oxidizer 1:10; oxidizer 1% to 3%. | For hair dyeing of "artistic" type |
| 10 | Max-mix diffusion (neutralization + pre-pigmentation + lightening + dyeing) | A dye for loosening gray hair + a dye for pre-pigmentation of gray hair + a mixtone for neutralizing the color of natural hair + the desired tone + mixtones for leveling and/or adding color + an oxidizer + shampoo | For simultaneous neutralization, lightening, pre-pigmentation and dyeing to the desired color; Dyeing over 100% gray hair; Dyeing over 100% unevenly colored hair shaft (highlighted, lightened and darkened stripes). |
| 11 | Diluted diffusion (prepared for the substrate or to add a color nuance) | | For color refinement; For the substrate; For adding a color nuance. |
| 11.1 | Diluted diffusion Type 1 | Dye + mixtone + oxidizer + shampoo | |
| 11.2 | Diluted diffusion Type 2 | Dye + oxidizer | |
| 11.3 | Diluted diffusion Type 3 | Mixtone + oxidizer | |
| 12 | Diffusion with direct-effect pigments | Direct-effect pigments + oxidizer or + oxidative dye, or + shampoo | For dyeing with direct-effect pigments |
| 13 | Clay diffusion | Clay + hot water + glycerin | Removal of direct-effect pigments and plant dyes from hair |

In preparation for dyeing, it is necessary to remove the cosmetic or natural pigment Removal of cosmetic pigment from dyed hair in salons is usually done by applying an acid wash. Acid wash is a ready-made acid composition, the components of which displace the artificial dyeing pigment from the hair structure.

For example, a professional emulsion for removing resistant dyes "Estelle Color Off" is known (https://korona-txu/prochee/smyvka-ili-obestsvechivanie-chto-luchshe-chem-otlichaetsya-kak-sdelat-v-domashnih-usloviyah-foto-do-i-posle-otzyvy-tsena.html). The commercially available acid wash kit includes three different formulations—reducing, catalyzing and neutralizing. To prepare the wash, you need to mix the reducing agent and the catalyst in equal amounts and leave this composition on your head for 20 minutes. If after this time the color does not go away, the procedure is repeated. To complete the process, you need to wash off the composition with running water and treat the strands with a neutralizer. At the very end, rinse your hair thoroughly using a deep-cleansing shampoo.

The intensity of oxidation depends on the concentration of peroxide molecules comprising for dyeing. The higher it is, the stronger the reaction and the lightening effect.

As a result of acid washing, the hair becomes dry and stiff and breaks under constant mechanical damage (drying, styling, combing the hair). They need to be restored.

2.1. Acid Diffusion

The author noticed and confirmed by testing that a commercial acid wash at certain dilution proportions, when adding shampoo (neutral or acidic pH) to an acid wash, blurs the color, reducing the density of the pigment, and does not completely remove it. This composition was named "acid diffusion" as it affects the color.

Depending on the amount of shampoo, the color is blurred more or less. The more shampoo we use, the weaker the color is blurred. It is especially helpful when you need to change the color a little, on the contrary, if there is little shampoo and a lot of acid wash, then, the color is removed faster.

The preferred proportions in acid diffusion from shampoo and acid wash are 0.5-3.0 parts of shampoo to 3.0-0.5 parts of acid wash.

For example:
- shampoo (0.5):acid wash (1);
- shampoo (1):acid wash (0.5);
- shampoo (1):acid wash (3);
- shampoo (3):acid wash (1);
- shampoo (1):acid wash (2);
- shampoo (2):acid wash (1).

The quantitative parameters of acid diffusion can be:
- shampoo (50 ml):acid wash (2 ml);
- shampoo (2 ml):acid wash (50 ml).

The mixing range varies as needed.

Using the composition of acid diffusion with a high shampoo content and a low acid wash concentration, the hairdresser can apply layers of acid diffusion more than once, monitoring the process of pigment removal.

To remove the cosmetic pigments according to the invention, acid diffusion is used in the ratio: acid wash 50% (Stage 1 and Stage 2, where "Stage 1" is a reducing composition, and "Stage 2" is a catalyzing composition) and shampoo 50%. The shampoo with a pH of 5.5 and below is used. The proportions are different: the range is 1 g of Stage 1 acid wash+1 g of Stage 2 acid wash+1 g of shampoo and up to 200 g of Stage 1 acid wash+200 g of Stage 2 acid wash+200 g of shampoo. The less is the amount of shampoo in the diffusion, the stronger is the substance concentration to remove the cosmetic pigment; conversely, the more shampoo and less acid wash, the slower the composition works, as the concentration is reduced, but thanks to the shampoo it penetrates deep into the cortex.

The exposure time of acid diffusion varies 5 to 30 minutes; depending on the manner the cosmetic pigment is removed. The difference between acid diffusion and the widely used acid wash (hereinafter referred to as "classic") is that the components penetrate deeper into the cortex than in the classic acid wash, and the time of this procedure within the salon is also reduced. Thus, in salon environment, it is possible to perform five acid diffusions within one hour instead of a single acid wash, since one common method wash takes one or more hours of work in the salon.

It is very important that during the application of acid diffusion, it is not applied to the scalp, but only to the hair, thereby providing a gentle effect on the skin.

If the oxidizing pigment on the previously dyed hair shaft is not removed using acid washes or acid diffusion, the removal is done using the lightening products: powders, oils, pastes or lightening diffusion described below.

Acid diffusion has two applications.

The first use is the removal of cosmetic pigment before applying discoloration or lightening diffusion, which will facilitate careful removing a part of the cosmetic pigment (relative to alkaline removals) and preserve hair quality. Acidic diffusions will remove part of the pigment, while alkaline diffusions (discoloration and lightening) will work faster to remove the pigment, which will affect hair quality for the better. Examples of the use of acid diffusion before discoloration or dyeing are given in the relevant variants of the method.

The second use is the removal of cosmetic pigment by acid diffusion before and after discoloration or lightening diffusions, which gives a stronger removal of cosmetic pigment. Thus, it is possible to remove a dark cosmetic color on hair quality on which discoloration diffusions can no longer work. Examples of the use of acid diffusion before and after discoloration or dyeing are given in the relevant variants of the method.

2.2. Lightening Diffusion

Lightening diffusion is intended to lighten natural hair and hair with a cosmetic base of at least TDL 7.

The composition of the lightening diffusion includes a dye (special blonds and 10 rows of TDLs)+oxide+shampoo.

The lightening strength is 1-3 tones up. It loosens the hair well. It is recommended not to apply to the scalp, because the shampoo in the mixture helps the dye components to penetrate deeper into the skin. It enables not just to lighten, but to loosen the hair for a deeper penetration of the subsequent dyeing composition.

With classical lightening (blondification) in salons using special blonds, the composition is used: dye+oxide, preferably in a ratio of 1:2. The composition is applied to dry hair and left for 30 to 60 minutes.

The lightening strength depends on alkalinity of the dye agent. The higher alkaline is the dye agent, the better is lightening and vice versa.

Loosening of gray hair almost does not occur, but the lightening strength is better than in the claimed method.

Lightening diffusion according to the claimed invention is used as a preparation for dyeing, for the uniform coincidence of natural hair TDL with the dyed hair TDL, and a smooth transition from natural hair to the dyed one. Diffusion enables you to loosen and lighten hair within 10-30 minutes, as a preliminary stage, to understand what the lightening background and its density on hair of each individual. Since everyone's hair is genetically lightened differently, and they have different amounts of pigment, the hairdresser cannot find the right recipe for preparing for dyeing, and under the classic method he does it blindly.

2.2.1. Lightening Diffusion Type 1.

Composition: dye+special blonde TDLs 11, 12, 14 (00 ammonia and LT, Ltx—various designations of special blonds)+oxide 12% or 9%+shampoo.

Dilution proportions: 1 part of dye:1 to 30 parts of oxide:shampoo 2 to 300 ml.

The more shampoo, the stronger is the effect, because the composition is more dispersed, it will penetrate deeper and loosen the hair better and lighten it deeper in cortex, but lightening itself will be weaker than with the classical dyeing method.

The more oxide, the less is the lightening strength, the lower is pH.

The more dye, the greater is the lightening strength and the higher is pH.

This lightening diffusion is created:
for lightening natural hair;
for lightening the cosmetic base of at least TDL 7;
for a mild lightening strength;
for loosening gray hair;
for loosening the natural base.

2.2.2. Lightening Diffusion Type 2.

The lightening strength is weaker than that of Lightening diffusion Type 1.

Composition: Dye TDL 10+3%-12% oxide+shampoo.

The dye is less alkaline and, as a result, less lightening;

The diffusion is less aggressive than Lightening diffusion Type 1. It is often necessary to raise one tone up or loosen the gray hair, and parallel lightening is not desirable. Then the composition of Lightening diffusion Type 2 will be preferable.

Dilution proportions: 1 part of dye:1 to 30 parts of oxide:shampoo 2 to 300 ml.

The more shampoo, the stronger (the more dispersed) is the composition, the deeper it penetrates, the better it loosens hair and the deeper it lightens the cortex.

The more oxide, the less is the lightening strength, the lower is pH.

The more dye, the greater the lightening strength and the higher is pH.

This lightening diffusion is created:
for lightening natural hair;
for lightening the cosmetic base of at least TDL 7;
for a low (1-1.5 tones up) lightening strength;
for loosening gray hair;
for loosening the natural base.

2.3. Discoloration Diffusion

If the oxidizing pigment on the previously dyed hair shaft is not removed using acidic washes or acidic and lightening diffusions, the removal is done using lightening products: powders, oils, etc.

The basic substances for clarifying products are oxide in the form of hydrogen peroxide and persulfates. Hydrogen peroxide is responsible for the oxidation of melanin. Reacting with other substances, it breaks down into water and active oxygen, which destroys natural or artificial pigment. The concentration of hydrogen peroxide in the preparations varies 3 to 12%. Persulfates are salts that enhance the Lightening reaction. Ammonium persulfate is most often used. When it is mixed with water or hydrogen peroxide, ammonia is released. It opens the scaly layer of the hair (cuticle), facilitating the rest of the drug substances to penetrate into it. Ammonia has a pungent aroma and irritating effect on the skin and mucous membranes. Some manufacturers replace ammonium persulfate with potassium and sodium salts or other alkaline components that "loosen" the cuticle. Such products have a damaging effect on hair.

In the classical method, when hair is discolored using a lightening powder, the following composition is used: lightening powder with 3% to 12% oxidizer. Ratio: 1 part of powder: 1 part of oxide to 1 part of powder: 3 parts of oxide.

The exposure time makes 20-60 minutes without increasing the temperature regime. This lightening is quite aggressive and destroys the hair structure.

According to the claimed invention, the commercial discoloration preparations are used as discoloration diffusions in the examples below.

For example, the ratio of the amount of lightening powder to the amount of oxide is 1 part of the lightening powder: 1 part of oxide to 1 part of lightening powder: 200 parts of oxide. These ratios make it possible to make the discoloration diffusion more acidic and effective at other pH ranges, which preserves hair quality and increases the exposure time of the powder for a better lightening effect.

To increase the stability of this discoloration diffusion and to solve the problem of preserving the degree of lightening, it is necessary to increase the mixture density with the lightening product on the hair section, i.e. to make the composition thicker.

For this purpose, a number of thickeners have been used, for example, SMDA KOPOLIMER (Nirvel thickener), as well as food thickeners: agar-agar, cellulose, or polymer, for example, polyvinylpyrrolidone, etc. Thickeners facilitate changing the consistency of the product, which greatly affects the mixture viscosity. A more viscous lightening product does not enable persulfates to penetrate deep into hair cortex and improves the mixture the stability. The mixture viscosity is very important in the claimed method, since the mixture viscosity does not enable clarifying substances (persulfates) to penetrate deep into the cortex (if it is not necessary), and the shampoo just enables you to penetrate deep into the cortex, during the procedures of hair lightening and dyeing.

Thus, at sufficiently low percentages of oxidizer, such as: 1%, 1.5%, 2%, 2.5%, etc. up to a higher 12%, it is possible to lighten the hair cleanly, while maintaining the hair quality.

In another example, the composition for removing cosmetic pigments is discoloration diffusion with active agents in the ratio of components: lightening powder 1 part+ oxidizer 3% 10 parts+thickener 10 to 40 ml+liquid amino acids 10 to 60 ml+silicone oil (demiticone) 5-15 ml+aragan oil 5-15 ml. Thus, with a decrease in the percentage of the oxidizer in the form of hydrogen peroxide, the mixture alkalinity increases 12% to 3%, but an increase in the amount of oxide to 10 parts balances the amount of oxygen and, as a consequence, the mixture, i.e. a balance was obtained between a low percentage of oxide and the mixture alkalinity. Adding a thickener makes the discoloration composition more viscous and dense, which improves the mixture the stability. Discoloration diffusion does not penetrate deep into the cortex, which enables you to increase the exposure time on hair, because the stability is higher, the composition is not liquid, and more product can be applied to 1 $mm^2$ of hair shaft surface due to the mixture density. Adding amino acids makes it possible for amino acids to take over part of oxidation from the outside. In addition, amino acids are a building material for hair, which enables you to restore disulfide bonds responsible for the integrity of hair structure and to preserve hair quality.

Any oils used for such purposes are possible to be added to the composition. These are triglycerides, which facilitate retaining hair moisture due to a greasier mixture, and also to make the composition more plastic, i.e. convenient to apply. Adding silicone provides a temporary protection to hair against being destructed with persulfates.

Other examples of component ratios in discoloration diffusion can be any of the above, 1 part of lightening powder: 1 part of oxide to 1 part of lightening powder: 200 parts of oxide with a concentration of 1% to 12%.

Examples of discoloration diffusion compositions.

Example 2.3.1 Mix 1

50 g of lightening powder+oxidizer over 6% (300 ml)+ liquid amino acids (5 to 200 ml)+oil (2 to 50 ml)+ silicone (2 to 50 ml)+thickener (2 to 100 ml). The exposure time is visual. Maximum 60 minutes.

Example 2.3.2. Mix 2

50 g of lightening powder+oxidizer over 3% (500 ml)+ liquid amino acids (5 to 200 ml)+oil (2 to 50 ml)+ silicone (2 to 50 ml)+thickener (2 to 100 ml). The exposure time is visual. Maximum 60 minutes.

Example 2.3.3. Mix 3

50 g of lightening powder+oxidizer over 2% (700 ml)+ liquid amino acids (5 to 200 ml)+oil (2 to 50 ml)+ silicone (2 to 50 ml)+thickener (2 to 100 ml). The exposure time is visual. Maximum 40 minutes.

Example 2.3.4. Mix 4

50 g of lightening powder+oxidizer over 1% (1000 ml)+ liquid amino acids (5 to 200 ml)+oil (2 to 50 ml)+ silicone (2 to 50 ml)+thickener (2 to 100 ml). The exposure time is visual. Maximum 50 minutes.

Cosmetic pigment is removed by acidic diffusions, and only then with discoloration diffusion.

Lightening diffusions, intended to lighten the natural hair pigment, can lighten hair that is not dyed in dark tones. Therefore, it is used less often than discoloration diffusion.

As described above, after applying discoloration or lightening diffusion, the use of acid diffusion makes it possible to remove cosmetic pigment smooth more strongly than using acidic before discoloration.

2.4. Dyeing Diffusion

This composition is intended for a comprehensive, persistent dyeing and as a replacement for classical dyeing.

The use of dyeing diffusion gives the following advantages to the method:

reducing the dyeing period;

visual control of dyeing, you can see how the color changes;

ability to control the color (shifting to any side of the color wheel);

the dyeing composition in this dilution is much safer for hair;

guiding the chemical process on hair;

partial skipping the lightening stage;

adding active agents.

Example 2.4.1. Dyeing Diffusion with Shampoo

It includes any dye (TDL 1 to 9)+oxidizer (1% to 9%), in the ratio of dye:oxidizer (1:2 to 1:6)+shampoo (2 to 300 ml).

Example 2.4.2. Dyeing Diffusion with Mixture Enrichment without Shampoo

Composition. Dye+oxidizer+liquid amino acids+jojoba oil or others+fish oil.

Ratios: oxidizer+dye (as specified by the manufacturer) for example 1:1 (options 1:2 or 1:3 to 1:10 are possible)+1% to 9% oxidizer; amino acids are possible 5 to 60 ml; oil 5 to 60 ml; fish oil 5 to 30 ml.

Example 2.4.3. Dyeing Diffusion with Water

It can be executed with a dye, mixtone and other types of oxidative pigments, direct-effect pigments or a mixture of oxidative pigments+direct-effect pigments. To improve hair quality, amino acids or sulfur-containing (cysteine and methionine) are added to this mixture.

Composition. Dye+water+liquid amino acids

The ratio of the dye to water is 1:1 to 1:20, where 20 are parts of water+amino acids 1 to 5 parts.

The exposure time is 10 to 40 minutes under heat or with a vaporizer.

This diffusion makes it possible to saturate the hair with non-oxidized pigment (a small molecule) due to the hydrogen bonds of water, the pigment penetrates well into the hair structure deeply enough and nourishes the hair not only with pigment, but also with amino acids, from which the keratin of the hair is built.

This diffusion can be attributed to one of the most progressive dyeing tools, which enables you active agents your hair steadily with minimal damage. It is excellent for weakened and damaged hair and refers to safe dyeing.

2.5. Pre-Pigmenting Diffusion

Intended for:

adding warm pigment to hair cortex, from where it was artificially removed with discoloration agents or natural absence of pigment (gray hair);

hair quality improvement, because "empty" hair is refilled with pigment and care.

Example 2.5.1 Pre-Pigmenting Diffusion Type 1

This diffusion is intended for blonde hair when the pigment has been removed by lightening. It has been developed for:

pre-pigmentation of previously discolored hair;

hair recovery (due to saturation with pigment);

hair darkening.

The composition of Pre-Pigmenting Diffusion Type 1:

a warm-color dye (in dye designation, the first digit before the dot is the designation of lightness or tone depth; the digits after the dot are color designations used in this method: 3—golden color, 4—orange, 5—warm red, 6-magenta (fuchsia or cold red) from 9.33; 9.34; 9.35; 9.43; 9.44; 9.45; 9.54; 9.55; 9.56; 9.65; 8.33; 8.34; 8.35; 8.43; 8.44; 8.45; 8.54; 8.55; 8.56; 8.65; 7.33; 7.34; 7.35; 7.43; 7.44; 7.45; 7.54; 7.55; 7.56; 7.65; 6.33; 6.34; 6.35; 6.43; 6.44; 6.45; 6.54; 6.55; 6.56; 6.65; 5.33; 5.34; 5.35; 5.43; 5.44; 5.45; 5.54; 5.55; 5.56; 5.65; . . . etc.;

mixtone from yellow to purple (yellow; yellow-orange; orange-yellow; orange; orange-red; red-orange; red warm; red-red cold)+oxide 1% to 3%+mask+shampoo.

It is mandatory to pre-add a mask either to the mixture or to the hair to lower pH of the mixture.

To reduce the lightening of hair lightened so far, dyes below TDL 8, i.e. 7, 6, 5, should be used mainly (since these rows are less alkaline). If a dye of TDL 5 is taken, it is diluted with an oxidizer up to TDL 9 exponentially.

For example:
to get TDL 9, the oxidizer is taken as 1:1;
to get TDL 8, the oxidizer is taken as 1:2, and TDL 8.8 is obtained;
to get TDL 7, the oxidizer is taken as 1:3, and TDL 8.5 is obtained.

Therefore, TDL 5 in relation to the oxidizer as 1:5 will not provide TDL 9, but will be darker.

It is preferable to dilute the oxidizer in a larger degree to get an opportunity to layering the same weak tone until the desired saturated one is obtained, for example, layering a blue tone to obtain a saturated blue.

Since there are different color densities for different brands, there is no possibility to darken customer's hair within the claimed method. Thus, TDL 5 should be diluted with an oxidizer of 1% or 1.5% in a ratio of 1:12. Recommended proportions: 1 part of dye:oxidizer 1 to 60 parts: shampoo 2 to 300 ml:mask 2 to 300 ml.

The dilution proportions depend on the following factors:
The more is the oxidizer amount, the more the pigment is blurred and, as a result, the less likely it is to darken the hair, and the use of the layering method of layering ensures an accurate hit to the desired tone level depth;
The more is the oxidizer amount, the less is the lightening strength, the lower pH;
The denser the color is needed and the less the lightening strength, the lower TDL should be chosen. High TDL is not desirable, because often discolored hair requires recovery, not destruction;
The larger is the mask amount, the more viscous and dense is the mixture, which does not enable the pigment to penetrate deeply into the hair of good quality, but is excellent for severely damaged (porous) hair;
The larger is the mask amount, the lower is pH;
The more shampoo is in this diffusion, the more "fine-grained" is the mixture penetrates deeper into the cortex, and affects the distribution (alignment) of color on the hair shaft.

In this pre-pigmenting diffusion, a combination of shampoo and mask is very important for clarified hair, because there is a more uniform distribution of care and pigment, they are introduced deeper into the cortex.

Example 2.5.2. The Composition of Pre-Pigmenting Diffusion Type 2

Mixtone+oxidizer+mask+shampoo. The color is cleaner, pH is lower than that of the dye (most often);
The color is denser (as mixtones are more saturated);
The brightness is higher than that of dyes due to decrease of bases (brown);
It is mixed with an oxidizer of 1% or 1.5%. Proportions: 1 part of mixtone:oxidizer 1 to 60 parts:shampoo 2 to 300 ml:mask 2 to 300 ml.

Example 2.5.3. Composition of Pre-Pigmenting Diffusion Type 3

Warm color dye+mixtone+(direct-effect pigment—optionally)+oxidizer+mask+shampoo. The dye agent acts as an ammonia carrier for the mixtone.

pH is higher than with a mixtone, but it can be adjusted;
Simultaneously a natural warm color is set, it is more intensive and pure;
The brightness is higher than that of dyes due to the reduction of bases (brown);
The brightness is higher due to the use of direct-effect pigment.

Direct-effect pigment is used during pre-oxidation with an oxidizer 1% to 6%. It is done to see the color stability in wearing and to simplify the subsequent pigment removal from hair.

The dye is mixed with 1% or 1.5% oxidizer. Proportions from 0.2 to 40 cm of mixtone:from 0.2 to 60 cm of dye:direct-effect pigment from 0.2 to 40 cm:oxidizer 1 to 60 parts:shampoo 2 to 300 ml:mask 2 to 300 ml.

Example 2.5.4

Dye agent 6.34+mixtone orange (TDL 7)+oxidizer 1%+mask+shampoo (preferably "post color" or pH 5.5).

Proportions: Dye agent 2 cm+mixtone 10 cm+oxidizer 8 parts+mask 25 ml+shampoo 15-20 ml Example 2.5.5

Dye agent 7.45+mixtone (warm red)+direct-effect pigment (warm red)+oxidizer+mask+shampoo.

Proportions: Dye 3 cm+mixtone 8 cm+direct-effect pigment 10 cm+15 parts of oxidizer+shampoo 5 ml+mask 10 ml.

These examples show that the dye in this type of dilution together with the mixtone is taken in small amounts; it acts as an ammonia carrier. Thus, the proportions can be different depending on the density of baseline products: color density, TDL of dye, a mixtone, and direct-effect pigments;
The proportions depend on hair quality;
The mask amount will be more if it is necessary to lower pH and nourish the hair;
The oxidizer amount will be more if the dye agent selected is dense, in view of diluting the color density;
The oxidizer amount will be more if the hair is destroyed and requires a small amount of ammonia intensive-color dye;
The direct-effect pigment amount will be more if color brightness and purity are needed;
The shampoo amount will be more, and it will dilute the color more than the oxidizer, because the shampoo is a soap solution and, compared with the oxidizer, dilutes the dyeing mixture more strongly by about 10 times, but increases pH and makes the composition more finely dispersed.

Example 2.5.6 Composition of Pre-Pigmenting Diffusion Type 4

Pre-Pigmenting Diffusion Type 4 includes water.
Composition: Dye (warm color)+mixtone (warm color)+water.
The exposure time is 20-30 minutes under heat, application of 1% to 3% oxidizer for 15 minutes; washing it off with shampoo; application of a mask; translucent dyeing.

This composition enables you to saturate hair cortex. The hair keratin gets saturated with a fine pigment and care products that are comprised in the dyeing mixture. Water and its hydrogen bonds act as a conductor and saturate hair with moisture. Preferably, when dyeing, the specified composition should be matured under a vaporizer.

This composition is also remarkable for:
best hair saturating with pigments, it darkens excellently;
stable dyeing;
gentle hair affecting;
It is recommended to complete after pre-pigmenting diffusion with water-free diffusions, because color refinement is better performed with shampoo added diffusions, thus, color formation is visible.

Example 2.5.7 Pre-Pigmenting Diffusion Type 5 for Gray Hair

There is no natural pigment in gray hair.
The diffusion has been developed for:
gray hair loosening and pre-pigmentation;
natural base loosening, for vitreous hair type.
Composition: Dye agent (warm color)—it is recommended to use dirty orange-red and red-orange. It is preferable to take ammonia dye and higher TDLs (closer to Blonde 8, 9), such as 9.45; 9.54; 8.45; 8.54; 7.45; 7.54 and intensified, where three digits are specified after the dot, e.g. 8.555 or 7.444;
+mixtone from orange to fuchsia (orange; orange-red-red; red-orange, warm red);
+2% to 6% oxidizer;
+shampoo.

Shampoo is added to the mixture in larger amounts to increase the degree of penetration and increase pH of the mixture.

It is possible to apply the composition in several stages, by layering.

A warm-color red dye 1 cm to 4 cm TDL 5.555 or 6.555 is added to the mixture (the first digit means the TDL, digits 555 after the dot mean warm red).

Proportions: 1 part of dye:oxidizer 1 to 30 parts:shampoo 10 to 300 ml+warm red dye TDL 5, 6, 1 to 4 cm.

The more is the amount of oxidizing agent, the less is the lightening strength, the lower is pH. It is desirable to take less oxidizer, in the ratio of 1:1 or 1:2 with the dye.

The more is the dye amount, the greater the lightening strength and the higher pH. An extensive loosening reaction is needed, therefore, the dye agent selected should have a higher TDL (thus, it comprises more alkali) and the shampoo proportion should be increased, since it promotes a better penetration and loosening.

A warm red or orange color is added either from a mixtone or from a dye agent of TDLs 5, 6 (probably, a mixtone+a dye).

Pre-pigmenting diffusions differ in their composition. However, in all compositions, for gray hair, the shampoo proportions tend to increase, and the dye agent TDL 9.8 contains more ammonia. For pre-pigmentation of the damaged blonde, the dye agent TDL 7.6 is selected. In any case, the oxidizer tends to the proportion with the dye 1:1 to 1:5.

2.6. Lightening and Pre Pigmenting Diffusion

It was created for lightening and pre-pigmentation of natural and gray hair.

The lightening strength is 1-3 tones up. It loosens the hair well. It is advisable not to apply it to the scalp, as due to the shampoo, it helps the dye components penetrate deeper into the scalp.

Example 2.6.1. Composition of Lightening and Pre-Pigmenting Diffusion Type 1

Dye+special blonde TDLs 11, 12, 14 (00 ammonia and LT, Ltx—various designations of special blonds)+12% or 9% oxidizer+shampoo+a warm-color dye agent (the first digit before the dot is the designation of lightness or tone depth; the digits after the dot are color designations used in this method: 3—golden color, 4—orange, 5—warm red, 6—magenta (fuchsia or cold red) 9.33; 9.34; 9.35; 9.43; 9.44; 9.45; 9.54; 9.55; 9.56; 9.65; 8.33; 8.34; 8.35; 8.43; 8.44; 8.45; 8.54; 8.55; 8.56; 8.65; 7.33; 7.34; 7.35; 7.43; 7.44; 7.45; 7.54; 7.55; 7.56; 7.65; 6.33; 6.34; 6.35; 6.43; 6.44; 6.45; 6.54; 6.55; 6.56; 6.65; 5.33; 5.34; 5.35; 5.43; 5.44; 5.45; 5.54; 5.55; 5.56; 5.65; etc.
+a warm-color mixtone.

Dilution proportions: 1 part of special warm-color blond dye (warm yellow, orange, orange-red, red-orange, warm red): 1 to 30 parts of oxidizer:shampoo 2 to 300 ml+dye TDLs 5 to 9, 0.01 parts to 3 parts+mixtone 1 to 20 cm.

Since this diffusion should lighten and pre-pigment at the same time, a balance is needed in terms of oxidizer and shampoo amounts:
the oxidizer proportions are close to those declared by manufacturer's factory (mainly 1:2, where 2 are parts of the oxidizer, but there may be more);
mixtone and dye (not a special blond) cater for the color needed for pre-pigmentation.

The diffusion is created for loosening gray hair and natural base and simultaneous pre-pigmentation.

Example 2.6.2

Dye TDL 12.3 (30 g)+8.44 (30 g)+mixtone (3 cm)+oxidizer 110 ml+shampoo (30 ml).

Example 2.6.3. Composition of Lightening and Pre-Pigmenting Diffusion Type 2 the dye is less alkaline and, as a consequence, less lightening;
less aggressive than the first type of diffusion lightening and pre-pigmenting. It is often necessary to raise one tone up or loosen gray hair, and parallel lightening is not desirable, then this composition will be preferred.
Dye TDL 10+3%-12% oxidizer+shampoo.

Dilution proportions: 1 part of TDL 10 dye warm color blonde (warm yellow, orange, orange-red, red-orange, warm red): 1 to 30 parts of oxidizer:shampoo 2 to 300 ml+dye 5 to 9 TDL. 0.01 parts to 3 parts+mixtone 1 to 20 cm.

Example 2.6.4

10.3 (30 g)+8.44 (30 g)+mixtone (3 cm)+oxidizer 70 ml+shampoo (30 ml).

2.7. Neutralizing Diffusion

Neutralization is conversion of any colors to neutral, i.e. gray. The main task of neutralization is to "remove" unwanted colors, and to neutralize with opposite colors (according to the color wheel).

It is created to neutralize the lightening background of the natural base and to neutralize cosmetic colors (pigments introduced from the outside into the hair).

Composition: Dye TDL 1 to 10 (TDL 11 is not included), which contains blue, green, blue-green, green-blue, green-yellow and blue-purple colors+oxidizer+shampoo.

A mixtone can also be included to concentrate the same neutralizing colors, which includes blue, green, blue-green, green-blue, green-yellow and blue-purple. In 90% of cases, a mixtone is required, because the amount of red, orange and other colors in hair exceeds the amount of neutralizing color in the dye.

Hair dyeing is frequent, but a proper neutralization, however, is not done before or during dyeing in beauty salons, because using RYB-circle, the hairdressers believe that neutral is brown, and simply add the dye, and, possibly, the desired color orientation. The fact that the hair already contains its own pigment, which was dyed before, is not taken into account by the hairdresser. Thus, a brown tone+an undesirable lightening background+cosmetic unwanted pigment are accumulated in hair.

Composition of Neutralizing Diffusion:

neutralizing dye 1 part+mixtone 0.5 cm to 50 cm+1% to 9% oxidizer in the ratio: dye to oxidizer from 1:1 to 1:30 (2 to 300 ml preferably)+shampoo 2 to 300 ml.

The objective of this diffusion is to:

neutralize all unwanted colors;

enhance dyeing resistance;

in the method of translucent hair dyeing, it is responsible for the predicted color washout;

reduce the period of hair lightening and dyeing. With the classical method, it would take at least 50 minutes. According to the claimed invention, the period of hair lightening and dyeing takes 7 to 30 minutes;

facilitate achieving hair neutralization on any kind and to perform it perfectly by 100% (i.e. to get into gray); it enables executing visual color control;

calculate the exact amount of neutralizing mixtone.

2.8. Neutralizing and Lightening Diffusion

It is created when it is necessary to simultaneously lighten and neutralize an undesirable color. There is a neutralization rule: any color goes into dimming by half a tone—a tone when it is neutralized. It happens, firstly, due to TDL (lightness) inherent to all neutralizing colors; secondly, color+color already means darker.

The neutralizing and lightening diffusion is intended for:

avoiding darkening in case hair quality is favorable for it;

for dyeing natural hair, when you need to lighten it more than a regular dye will do, and to neutralize the lightening background;

for dyeing natural hair roots;

avoiding darkening of previously dyed hair having an undesirable shade.

Composition: Neutralizing dye TDL 1 to 9, from 0.01 parts to 1 part+neutralizing mixtone 0.5 cm to 50 cm+special blonds (TDL 11, 12, 14) or TDL 10 from 0.01 parts to 1 part+sufficiently high oxidizer 4.5% to 12%, 2 to 500 ml+shampoo, 2 to 200 ml.

The proportions depend on the lightening strength. Most desirable is seeing the lightening strength on the hair shaft (the more oxidizer, the less is the lightening strength; the more dye lightening rows, the stronger is the degree of lightening);

The proportions also depend on color concentration (density, saturation) of neutralizing mixtone and dye (the more oxidizer, the lighter is color).

Example 2.8

Hair is TDL 5. The lightening background is red. The purpose is to remove this color and not to darken the hair (for example, by obtaining TDL 6.1-ash gray). Since neutralization makes the color darker by a tone, in order not to darken the hair from TDL 5 to TDL, this diffusion type is applied.

Composition: Dye TDL 10 (20 g)+TDL 7.2 (brown-green dye) (30 g)+mixtone green (10 cm)+oxidizer 9% 120 ml+shampoo 20 ml.

The exposure time is 20 to 40 minutes. The background color of lightening was removed, and TDL was not darkened and made lighter-up to TDL 6.

Result. Color TDL 6.1 was obtained.

Advantages:

This diffusion reduces the time of hair lightening and dyeing. With the classical method, this process would take at least 50 minutes. According to the claimed invention, the time of hair lightening and dyeing takes 7 to 30 minutes;

It enables to achieve neutralization on any kind of hair and perform it 100% accurate (to get into gray), enables you to make visual color control;

The exact amount of neutralizing mixtone can be calculated;

Lightening penetrates deep into the hair; the background neutralization is deeply lais as well.

2.9. Artistic Diffusion

The artistic diffusion is created for hair dyeing of artistic type, when the mixtones are diluted separately in containers (separately pink, separately green, separately yellow, etc.). Mixtones are diluted in the ratio: mixtone to oxidizer from 1:10 to 1:40, preferably 1:20. The oxidizer in this case is low, from 1% to 3%.

The artistic dyeing diffusion is applied on hair (for example, dye 7.1+oxidizer 1.5%) 1:2; left for 10 minutes, mechanically massaged, then 20% of the composition is washed off with water, and the desired color is applied from a container with a certain mixtone (blue mixtone+oxidizer 1:20). The exposure time is visual, but not less than 7 minutes (dilution enables it or elevate the ratio to 1:40). When the desired color is reached, it is washed off with water and the process is completed with a mask with an acidic pH ("post color"), and washed off with water.

If the color does not suit the customer, you can simply wash off 20% of the composition with water and apply another color, for example, pink. As a result, 7.112 is obtained, where 7 is TDL, the figure "1" after the dot is a cold ash-blue color, and "2" is pink. The mixtone has strengthened the dye from 7.1 to 7.11.

You can create any colors, change them in 2-3 minutes and see the whole process of obtaining color.

2.10. Max-Mix Diffusion (Neutralization+Pre-Pigmentation+Lightening+Dyeing)

Max-mix diffusion is intended for simultaneous neutralization, lightening, pre-pigmentation and dyeing in the desired color.

Classical dyeing should meet these needs, but due to the lack of color concentration, it does not achieve it.

With this diffusion, you can dye over 100% of gray hair; dye over 100% of unsmooth hair shaft (e.g. highlights, lightened and darkened stripes).

Example 2.10

Composition: dye TDL 10.0 (10 g) (for loosening gray hair, for example)+TDL 6.34 (10 g) (for pre-pigmentation of gray hair)+blue-green mixtone (10 cm) (to neutralize the color of natural hair)+target tone TDL 7.1 (40 g)+mixtone magenta 3 cm (if green will prevail)+orange mixtone (4 cm) (as pre-pigmentation from the dye may not be enough)+oxidizer 110 g+shampoo 30 ml.

In this diffusion, black color may also be present to add gray and a natural base.

All these types of diffusions help to create colors with 100% getting into the desired color and to restore the hair structure parallel to dyeing.

2.11. Diluted Diffusion

Example 2.11.1 Diluted Diffusion Type 1

Diluted Diffusion Type 1 comprises a small the dye amount, from 1 to 20 cm, and mixtones predominate. The maximum oxidizer amount is 40-300 ml; shampoo 2 to 200 ml—depending on hair density, for hair loosening and as a diluent. Composition. Dye 1 to 20 cm, mixtone 1 to 100 cm, oxidizer 40-300 ml, shampoo 2 to 200 ml.

Example 2.11.2 Diluted Diffusion Type 2

Diluted Diffusion Type 2 comprises only a dye agent+oxidizer.

Diluted diffusion can be without adding a shampoo.

If the dye should penetrate deeper, shampoo is needed, if the dye is applied on hair surface, the shampoo is not required.

Composition. Dye 1 to 20 cm, maximum oxidizer amount 40-300 ml.

Example 2.11.3 Diluted Diffusion Type 3

The Diluted Diffusion Type 3 comprises only a mixtone+oxidizer.

In Diluted Diffusion Type 3, the mixtone amount from 1 to 100 cm prevails; the maximum oxidizer amount is 40-300 ml.

If the dye needs to be diluted to make the color lighter, or a finely dispersed consistency is needed, the shampoo is added in the amount of 2 to 200 ml.

Diluted diffusion is used to refine the color.

An Example of Color Refinement.

As a dyeing outcome, the tone turned out to be too cold. The composition of the diluted diffusion for refinement: mixtone orange 5 cm+low oxidizer, preferably 1%-1.5% (70 ml)+dye TDL 7.4 (2 cm) (as a carrier comprising more ammonia, for color durability)+shampoo 30 ml.

2.12. Diffusion with Direct-Effect Pigments

Diffusion with direct-effect pigments is used for dyeing with direct-effect pigments.

The diffusion is applied to wet hair: direct-effect pigments (50 g)+oxidizer 5 to 200 ml or direct-effect pigments (50 g)+oxidizer (5 to 200 ml)+oxidative dye (dye TDL 10.0 (1 cm to 20 cm); exposure time 5 to 40 minutes, preferably under heat, or diffusion is applied to wet hair: direct-effect pigments (50 g)+oxidizer (5 to 200 ml)+shampoo, or direct-effect pigments (50 g)+oxidizer (5 to 200 ml)+oxidative dye (dye type 10.0 (1 cm to 20 cm)+shampoo;

rinse with cool water, apply a mask, leave for 15 minutes under heat; rinse with water.

It is possible to re-apply diffusion, i.e. make a translucent dyeing.

13. Clay Diffusion

This type of diffusion enables you to remove direct-effect pigments, plant dyes, such as henna, basma, etc. from the hair.

Previously it was thought that it was impossible to completely remove this type of dyes, but clay diffusion enables you to do this.

The composition of clay diffusion: clay, preferably white-kaolin+hot water brought to a boil+glycerin.

The clay is kneaded with water brought to a boil (boiling water), then glycerin is added to the hot mixture.

Example of Clay Diffusion Composition 2.13.1

150 clay+150 water (boiling water)+10-20 ml of glycerin.

The resulting diffusion removes direct-effect pigments and plant dyes. The removal procedure is described in the relevant method.

3. Other Method Components 3.1. Substrate

The substrate is the basis for dyeing with the main color, i.e. applying "color to color", which can be performed at different depths of the hair cortex. The substrate enables you to saturate the necessary hair shaft with color before dyeing. The main substrate task is to prolong the dyeing weariness, to show hair shaft irregularities, to serve as an impeccable basis for creating a future 100% predictable color and a lasting color.

The substrate is performed with the diffusions mentioned above, different types of diffusions will give different versions of the substrate. Even a single diffusion, for example the diluted one, made more concentrated than the other, will provide a denser substrate. By choosing the oxidant concentration percentage and the dye amount, the diffusion penetration depth is adjusted and, as a result, this diffusion, performed before the main dyeing, becomes a substrate.

Types of substrate:

dense substrate, i.e. saturated in color, then the main dyeing becomes more transparent;

transparent substrate, i.e. not saturated in color, and the main dyeing, on the contrary, will be denser;

neutralizing substrate is used to neutralize the natural pigment (background lightening) and cosmetic base;

duplicate substrate is a substrate of the same color direction as the desired color. For example, it is necessary to create a persistent red color, then for durability they make the substrate orange, lighter than the desired one;

artistic substrate is used with direct-effect pigments;

re-neutralizing substrate is prepared for persistent dyeing, durability up to 5-6 months (leaching into the desired color occurs after 7-20 days, and the color is stable for 6 months).

Example 3.1.1

A substrate that re-neutralizes the orange background. Composition: blue mixtone 10 cm+oxidizer 6% (100 ml)+shampoo 50 ml; exposure time 7 to 40 minutes; blue color is obtained;

The substrate depth depends on the depth of its penetration into the cortex. The alkaline dye and the oxidizer percentage are responsible for it. The higher is the oxidizer percentage, the deeper is penetration. Oxidizer 12% penetrates the deepest; oxidizer 9% penetrates to the medulla, but less deeply than oxidizer 12%; oxidizer 7.5% penetrates to the middle of the hair; oxidizer 6% penetrates to the middle, but closer to the surface; oxidizer 1.5% penetrates on the hair surface, not deeply.

The deeper the pigment was located in the hair depth before dyeing, for example, the dyed hair was black, and the red pigment was deep inside, the deeper penetration is necessary to neutralize the pigment, and a deep substrate is used.

In another case, if 12% lightening dye was used on natural hair before dyeing, the lightening background was bared deep inside, and a deep substrate is also used;

The surface substrate is used:
when there was no deep penetration into the cortex before dyeing, and also when there is no task to create a durable color;
if the hair lightening is supposed to be next day after the dyeing day;
if they do not affect the natural base of previously undyed hair.

The main color is the main dyeing in the desired color. It is performed with diffusion or modified classical dyeing (with skipping the lightening stage, addition of dietary supplements, masks, acids, etc.).

Example 3.1.2

The dyeing composition of the main color is prepared comprising: dye TDL 7.1 (30 g)+oxidizer 1% (100 ml)+colorant 1.0 (5 cm)+mixtone orange pure color, opposite to blue, 3 cm+mask+active agents+oils;

The dyeing composition is left for 20-30 minutes after diluting in a container. Then, the dyeing composition of the main color is applied on washed wet hair, and there may also be care products on hair.

3.2. Final Color Refinement

Refinement is correcting the shortcomings that resulted from dyeing, for example, due to dyeing heterogeneity.

Refinement is always done mainly with dyeing, pre-pigmenting, neutralizing, or diluted diffusions. The diffusions should be sufficiently diluted in color, where the dye amount is small, 1 cm to 20 cm, and mixtones prevail. The amount of oxidizer is maximum 40-300 ml; shampoo amount—depending on hair density (for loosening) and as a diluent, from 2 to 200 ml.

Example of color refinement. As a result of dyeing, the tone turned out to be too cold. Refining composition to improve the situation: mixtone orange 5 cm+low oxidizer, preferably 1%-1.5% (70 ml)+dye TDL 7.4 (2 cm) (as a carrier comprising more ammonia, for color durability)+shampoo 30 ml.

3.3. Final Translucent Hair Dyeing—Glaze Coating by Layers

The final glaze coating (lamination) is an addition of a color nuance, i.e. the application of a thin layer of another color that will lie on the surface of the main color and glare when light is refracted. It is performed with diluted diffusion or diffusion with direct-effect pigments. For final glaze coating, it is preferable to use a direct-effect dye or a MEA dye, ammonia-free DEA dye, or direct-effect mix+ammonia-free dye.

Components of glaze coating composition: the base is an oxidizer of the lowest concentration (%) (10 to 300 ml)+direct-effect pigment (1 to 20 cm)+ammonia-free dye (1 to 5 cm);

It is recommended to acidify the composition with a mask (10 to 40 ml)+shampoo (2-100 ml).

The final color should be transparent, like a thin layer of dyeing composition.

Direct-effect pigments provide an optical mixing, which visually looks like an overlay of one color on another. In the glaze coating composition, the direct-effect pigment is mixed with the oxidizer to check its color stability, in addition, the direct-effect pigment, when mixed with the oxidizer, lies more smooth.

Example 3.3.1

Mixture of ammonia-free dye (red) TDL 5.55 1 cm+direct-effect pigment 10 cm (magenta)+oxidizer 100 ml+shampoo 30 ml+mask 30 ml.

Apply for at least 7 minutes, provide visual control over the color manifestation. Durability directly depends on the exposure time.

The translucent hair dyeing method can be performed in various ways, as described below. The main difference from the existing methods is layering of color onto color and non-classical dye diluting.

The implementation of the translucent hair dyeing method according to Option 1 is intended for dyeing natural hair, i.e. not previously subjected to dyeing or lightening. In the claimed method of hair dyeing, the dye is diluted with an oxidizer to obtain the transparency of the applied dye layer on the hair shaft. The dye layers should be applied to the prepared hair shaft, aligned by quality and color, and brought to a neutral tone.

Adding an oxidizer to a mixture with a direct-effect pigment makes it easier to extract this dye type from hair later.

Adding an oxidative dye to the mixture with a direct-effect pigment and an oxidizer enables the direct-effect pigment to lie more smoothly, even on hair shaft not uniform in quality, and go deeper into the cortex.

The translucent hair dyeing method according to Option 1 includes the following steps:
preparation for dyeing:
hair cleansing;
lightening, if necessary, lighter than the natural tone;
composition removal;
alignment of the hair shaft by quality.

Translucent hair dyeing includes the following steps:
hair dyeing to the desired tone with a dyeing composition;
dyeing composition removal;
hair shaft alignment by color or refinement of the result;
layering of the dyeing composition by lamination to achieve a volumetric dyeing;
composition removal;
hair recovery.

3.4. Lightening of Natural Hair

Depending on customer's desire, the following variants of natural hair dyeing are possible.
1. Lightening of natural hair with discoloration preparations (where persulfate salts are comprised).
2. Lightening of natural hair with hair dye.
3. Darkening of natural hair.
4. Tone-to-tone dyeing with oxidative dyes.
5. Toning with direct-effect pigments.

Example 3.4.1. Lightening of Natural Hair with Discoloration Preparations

There are fourteen Tone Depth Levels (TDLs) of hair color (i.e. lightness, where TDL 1 is black, TDL 7 is gray, TDL 14 is white).

The dye amount in the examples is indicated on average, as it varies depending on hair density and product application area (all hair or a strip, a hair area).

The thickener, as well as active agents, can be used in compositions, or they may be absent.

Example 3.4.1.1. Lightening by 1-3 Tones Up

Lightening of natural hair by 1-3 tones up is done in the following sequence:

Discoloration diffusion of viscous consistency is applied to wet hair, including lightening powder 50 g+oxidizer 1%-12% (100 ml to 1000 ml)+liquid amino acids (5-200 ml)+oil 2-50 ml+ silicone 2-50 ml+thickener (2 to 100 ml). The exposure time is visual, depends on the selected oxidizer concentration: for 1.5%, the maximum time is 2 hours; for 6%, the maximum time is 1.5 hours; for 12%, the maximum time is 60 minutes. The viscous consistency not only enables to lighten the hair, but also improves the product stabilization;

Discoloration diffusion is removed: wash the hair abundantly with water; shampoo for 5 minutes (shampoo pH 5.5 and below); rinse with water; apply a recovery mask with acidic pH for 10-15 minutes; rinse with water;

pH is lowered by specialized means or citric acid;

Hair recovery is made with active agents;

Dyeing is started. Dyeing is done with translucent glaze coating by layers, i.e. by repeated application of diffusion layers. Mainly dyeing, or pre-pigmenting, or neutralizing or diluted diffusions are used.

Example 3.4.1.2. Lightening by 4-5 Tones Up

It is required to lighten the hair by 4-5 tones up. Lightening is done in the following sequence:

Discoloration diffusion of viscous consistency is applied to wet hair, including lightening powder 50 g+oxidizer 1%-12% (100 ml to 1000 ml)+liquid amino acids (5-200 ml)+oil (2-50 ml)+ silicone (2-50 ml)+thickener (2 to 100 ml). The exposure time is visual, and it depends on the oxidizer concentration: for 1.5%, the maximum time is 2 hours; for 6%, the maximum time is 1.5 hours; for 12%, the maximum time is 60 minutes;

In case the desired tone level depth has not been reached, the procedure of applying discoloration diffusion with a lightening powder is repeated, while the oxidizer percentage in the mixture decreases or remains stable. The mixture has a viscous consistency.

For example: Diffusion 1:50 g powder+oxidizer 6% 300 ml+active agents+thickener.

Diffusion 2: lightening powder 50 g+500 ml oxidizer 3%+active agents+thickener;

Between application of Diffusions 1 and 2, the hair is washed only with water if there was no contact with the scalp;

Hair recovery mask with an acidic pH is applied, left for 10-20 minutes and rinsed with water;

Diffusion 3 is applied with the composition: lightening powder 50 g+oxidizer 1.5% 500 ml+active agents+thickener;

Rinse with water;

A recovery mask with an acidic pH is applied, left for 10-20 minutes and rinsed with water;

In case there was contact of the lightening powder with the scalp, then the hair is abundantly washed with water; washed with shampoo for 5 minutes (shampoo pH 5.5 and below); washed with water; a regenerating mask with acidic pH is applied for 10-15 minutes and washed off with water.

If the desired tone level depth is reached, the discoloration diffusion is removed:

Diffusion 3 is removed; the hair is washed abundantly with water; washed with shampoo for 5 minutes (shampoo pH 5.5 and below); washed with water; a regenerating mask with acidic pH is applied for 10-15 minutes and washed off with water;

pH is lowered by specialized means or citric acid;

Hair recovery mask with active agents is applied and rinsed with water;

Dyeing is started. Dyeing is done with translucent glaze coating by layers, i.e. by repeated application of diffusion layers. Mainly dyeing, or pre-pigmenting, or neutralizing or diluted diffusions are used.

Example 3.4.1.3. Lightening by 6-10 Tones Up

It is required to lighten the hair by 6-10 tones up. Lightening is done in the following sequence:

Discoloration diffusion of viscous consistency is applied to wet hair, including lightening powder 50 g+oxidizer 1%-6% (100 ml to 1000 ml)+liquid amino acids (5-200 ml)+oil (2-50 ml)+ silicone (2-50 ml)+thickener (2 to 100 ml). The exposure time is visual, and it depends on the oxidizer concentration: for 1.5%, the maximum time is 2 hours; for 6%, the maximum time is 1.5 hours Application 1 of oxidizer 6%, the exposure time is 60 minutes:

Mixture removal with a dry towel, so that the mixture is almost not on the hair. At the same time, there was no composition on the scalp;

A new mixture of the same composition is prepared, but the oxidizer concentration is taken lower, 3%. The oxidizer amount is also increased compared to Application 1. Composition: lightening powder 50 g+oxidizer 3% (100 ml to 1000 ml)+liquid amino acids (5-200 ml)+oil (2-50 ml)+ silicone (2-50 ml)+thickener (2 to 100 ml);

Leave for 40-60 minutes;

Mixture removal with a dry towel;

A new diffusion mixture is prepared, comprising: lightening powder 50 g+oxidizer 2% (100 ml to 1000 ml)+liquid amino acids (5-200 ml)+oil (2-50 ml)+ silicone (2-50 ml)+thickener (2 to 100 ml). The exposure time is visual; it depends on concentration of the selected oxidizer: for 1.5%, the maximum time is 2 hours; for 6%, the maximum time is 1 hour. The oxidizer is taken lower than that of the previous diffusion, for example 2%, but the amount of oxidizer is increased compared to Application 2. The exposure time is 40 minutes;

The test for hair extensibility is performed. If the test showed that hair quality enables them to be lightened further on, then Remove the mixture with a dry towel;

Prepare a new mixture; the oxidizer is taken lower, for example, 1%. The amount of oxidizer is increased compared to Application 3; the exposure time is 50 minutes.

Further, this composition is left with oxidizer 1%, and, washing off the previous mixture, the subsequent one is applied with a low oxidizer percentage. It reduces the degree of hair destruction. With a decrease in oxidizer percentage, pH of the composition is higher;

If the desired tone of level depth is not reached, the procedure of applying the lightening powder as part of discoloration diffusion is repeated, while the oxidizer percentage in the mixture is reduced. Constantly monitor the hair extensibility. If the quality is suitable, continue the procedure until the desired tone level depth is reached. If hair quality does not enable further lightening, quit the procedure;

Remove the mixture: the hair is abundantly washed with water; washed with a shampoo for 5 minutes (shampoo with pH 5.5 and below); washed with water; a regenerating mask with acidic pH is applied for 10-15 minutes; washed off with water;

pH is lowered by specialized means or citric acid;

Hair recovery mask is made;

Dyeing (translucent glaze coating) by layers is started;

The substrate is made (with a diluted diffusion);

Hair is washed with water and wrung out;

The acid diffusion is applied (to blur a part of the substrate color not to darken the color);

Dyeing in the desired color is made using the dyeing diffusion or direct-effect pigment diffusion, or other diffusions;

Hair is washed with water. If there was contact with the scalp, rinse with water, then shampoo the site, then rinse with water again;

The acid diffusion is applied (to blur a part of the final color);

Hair is washed with water. If there was contact with the scalp, rinse with water, then shampoo the site, then rinse with water again;

Hair recovery with active agents;

Refinement (color alignment) of hair with pre-pigmenting and neutralizing diffusions, other diffusions are possible;

Hair quality alignment (restoration of damaged areas);

Color refinement on areas where an undesirable color has appeared or the color is not stable;

Mixture removal in the sequence: water, shampoo, mask, water;

Hair recovery with active agents;

Translucent glaze coating of hair with diluted diffusion and direct-effect pigment diffusion;

Removal of diffusions in the sequence: water, shampoo, mask, water.

Examples of discoloration diffusions used when lightening natural hair with discoloration preparations are presented in Section "Diffusion compositions used in the claimed method", Part 3. "Discoloration diffusion", Mixtures 1-4 (see also Table 1, Items 3.1-3.4).

You can do all lightening with Mixture 4, i.e. with 1% oxidizer, which is more gentle for hair, but it will take a lot of time to achieve the desired lightness.

The proportions of the oxidizer and all components can be specified similarly to Example 3.3.3. Lightening by 1-3 tones up.

The strand stretchability test is done as follows: the discoloration powder is removed from a hair strand with a wet towel, and a mask is applied on the strand for 3 minutes. The mask is removed with a wet towel, and various strand sections are pulled in different directions with your fingers.

If a hair strand springs and does not tear, you can continue the procedure, if necessary. At the same time, constantly monitor the process.

If a strand is torn, the procedure should be discontinued.

If the strand is dense, then the hair is in good quality.

Example 3.4.2. Lightening of Natural Hair with Lightening Diffusion (See Table 1, Items 2.1-2.2)

Example 3.4.2.1. Lightening by 1-1.5 Tones Up

Lightening by 1-1.5 tones is done in the following sequence:

Special blonds of TDL rows 11, 12, 14 or 10 are applied to wet hair;

Dye of special series (11, 12, 14), 30 g+oxidizer 9%-12% (60 ml to 1000 ml)+shampoo (5 to 500 ml)+liquid amino acids (5-200 ml)+oil 2-50 ml+ silicone 2-50 ml+thickener (2 to 100 ml), a mixture of viscous consistency; or Dye of special series (11, 12, 14), 30 g+oxidizer 9%-12% (60 ml to 1000 ml)+shampoo (5 to 500 ml). The exposure time is visual, minimum 5 minutes, maximum 40 minutes;

Dye TDL 10 is applied to wet hair as follows: dye, 30 g+oxidizer 3%-12% (30 ml to 1000 ml)+shampoo (5 to 500 ml)+liquid amino acids (5-200 ml)+oil (2-50 ml)+ silicone (2-50 ml)+thickener (2 to 100 ml);

or dye TDL 10 is applied on the wet hair as follows: dye, 30 g+oxidizer 3%-12% (30 ml to 1000 ml)+shampoo (5 to 500 ml); and a mixture of viscous consistency. The exposure time is visual, minimum 5 minutes, maximum 40 minutes;

Mixture removal: the hair is abundantly washed with water; washed with shampoo for 5 minutes (shampoo pH 5.5 and below); washed with water; a regenerating mask with acidic pH is applied for 10-15 minutes, and washed off with water;

pH is lowered by specialized means or citric acid;

Hair recovery mask is made with active agents;

Dyeing is started.

Example 3.4.2.2. Lightening by 2-4 Tones Up

Lightening by 2-4 tones up is done in the following sequence:

Special blonds of TDL rows 12, 14 are applied to dry hair.

Dyeing composition comprising: dye, 60 g+oxidizer 9%-12% (120 ml to 1000 ml)+liquid amino acids (5-200 ml); a mixture of viscous consistency. The exposure time is visual, minimum 40 to 70 minutes;

Mixture removal: the hair is abundantly washed with water; washed with shampoo for 5 minutes (shampoo pH 5.5 and below); washed with water; a regenerating mask with acidic pH is applied for 10-15 minutes; washed off with water;

pH is lowered by specialized means or citric acid;

Hair recovery mask is made with active agents.

Dyeing is started, if necessary.

3.5. Darkening of Natural Hair

If it is necessary to darken natural blonde hair, and the customer wants to have a rich color as a result, then orange or red colors should be added to the dyeing composition, which correspond to the lightening background. Natural eumelanin and pheomelanin during oxidation appear in different colors with various TDLs.

Scheme 1.1 Manifestation of the lightening background with various TDLs on natural hair.

TDL 5, 4, 3—red;

TDL 6, 7—red-orange;

TDL 8, 9—orange;

TDL 10—yellow-orange.

Neutralization occurs in the following colors:
Scheme 1.2 Manifestation of neutralization with various TDLs on natural hair.
TDL 5, 4, 3—green;
TDL 6, 7—green-blue and blue-green;
TDL 8, 9—blue color;
TDL 10—blue-purple.

The examples indicate the average amount of dye and other components; it may vary depending on the density, length, porosity of the hair and saturation of the dye and mixtone.

Example 3.5.1. Natural Hair—Natural Blonde (TDL 8, 9, 10)

The intention is to dye hair TDL 9, 10 into TDL 6. The desired color is 6.1—ash-natural TDL 6.
Dyeing diffusion:
Dye 6.1 (50 g)+6.0 (30 g)+orange mixtone (2-8 cm)+blue mixtone (2 to cm)+low 1% to 3% oxidizer (80 to 500 ml)
or
Dye 6.1 (50 g)+6.0 (30 g)+orange mixtone (2-8 cm)+blue mixtone (2 to 6 cm)+low 1% to 3% oxidizer (80 to 500 ml),
or
Dye 6.1 (50 g)+6.0 (30 g)+orange mixtone (2-8 cm)+blue mixtone (2 to 6 cm)+low 1% to 3% oxidizer (80 to 500 ml)+shampoo (5 to 500 ml)+liquid amino acids (5-200 ml)+oil (2-50 ml)+ silicone from (2-50 ml)+thickener (2 to 100 ml),
or
dye 6.1 (50 g)+6.0 (30 g)+orange mixtone (2-8 cm)+low 1% to 3% oxidizer (80 to 500 ml)+shampoo (5 to 500 ml)+liquid amino acids (5-200 ml)+oil (2-50 ml)+ silicone (2-50 ml)+thickener (2 to 100 ml).

The composition exposure time is 10 to 40 minutes; dyeing is done on wet hair; then the mixture is removed: the hair is abundantly washed with water; washed with shampoo for 5 minutes (shampoo pH 5.5 and below); washed with water; a regenerating mask with acidic pH is applied for 10-15 minutes, and washed off with water;

Oxidizer proportions depend on intensity, mixtone amount and dye density. If you add 6 cm of blue saturated mixtone, it will be equivalent to adding 3-5 g of dye TDL 5.5, i.e. equivalent to hair darkening. To avoid it, you should add an oxidizer in larger amounts.

If there is a shampoo in the mixture, it will dilute the color more due to a better dye distribution over the hair shaft (i.e. a smaller amount of dye is laid on a large surface area of the hair).

Correction by the Method of Translucent Hair Dyeing

If the resulting color is not intensive enough, the diluted diffusion is used: dye 6.1 (10 g)+oxidizer 1% (80 ml)+shampoo (20 ml) are applied to the hair shaft and preferably not applied to the scalp. The exposure time makes 7 to 25 minutes with constant mechanical impact by hands; visual control; abundantly washed off with water.

If the process is over, remove the mixture: rinse abundantly with shampoo for 5 minutes; apply a recovery mask with an acidic pH for 10-15 minutes; rinse with water. If there is a desire to add colors, between the applied diffusions, they are simply washed off with water without removing the mixture.

Translucent Hair Dyeing—Glaze Coating by Layers

If you want to add a color nuance or remove an undesirable color nuance, the final glaze coating is done. In the example above: baseline hair color is TDL 9, 10; the desired color after dyeing—TDL 6.1 ash-natural. The diluted diffusion can be used: blue mixtone (2 cm) makes the color colder+pink mixtone (3 cm)+oxidizer 40 ml+shampoo 30 ml+mask 20 ml; exposure time 7 to 25 minutes, with constant mechanical impact by hands; visual control; rinsing with water abundantly. At the end of the process, remove the mixture by shampooing for 5 minutes; apply a recovery mask with an acidic pH for 10-15 minutes; rinse with water.

Example 3.5.2. Natural Hair (TDL 7, 6, 5)

To darken the natural hair of these TDLs, as a rule, it is enough just to use darkening dyeing compositions.
Example: natural hair TDL 7, the desire is to get TDL 5.0 (natural).
Dyeing composition containing dyeing+neutralizing+pigmenting diffusion in one composition: dye 5.0 (50 g)+1.0 (3 cm)+orange mixtone (2-8 cm)+blue mixtone (2 to 6 cm)+oxidizer low 1% to 3% (80 to 500 ml)
or
The same composition with the addition of shampoo (5 to 500 ml)+liquid amino acids (5-200 ml)+oil (2-50 ml)+silicone (2-50 ml)+thickener (2 to 100 ml),
or
Dye 5.1 (50 g)+1.0 (3 cm)+oxidizer low 1% to 3% (80 to 500 ml)+shampoo (5 to 500 ml)+liquid amino acids (5-200 ml)+oil 2-50 ml+ silicone 2-50 ml+thickener from (2 to 100 ml).
or
Dye 5.1 (50 g)+1.0 (3 cm)+low oxidizer 1% to 3% (80 to 500 ml)+liquid amino acids (5-200 ml)+oil 2-50 ml+ silicone 2-50 ml+thickener from (2 to 100 ml).

There may also be layers of other diffusions by the method of translucent hair dyeing.

Example 3.5.3. Natural Hair (TDL 4, 3)

Natural hair TDL 4. The desire to darken them to TDL 1.0 with a blue tint.
Dyeing composition:
Dye 1.0 (50 g)+blue mixtone (2 to 30 cm)+low oxidizer 1% (80 to 500 ml)+shampoo (5 to 500 ml)+liquid amino acids (5-200 ml)+oil (2-50 ml)+ silicone (2-50 ml)+thickener (2 to 100 ml)
or
Dye 1.0 (50 g)+blue mixtone (2 to 30 cm)+low oxidizer 1% (80 to 500 ml)+liquid amino acids (5-200 ml)+oil (2-50 ml)+ silicone (2-50 ml)+thickener (2 to 100 ml).

At the request of the customer, color refinement and translucent hair dyeing can be done.
3.6. Dyeing the Natural Hair "Tone to Tone"
3.6.1. Dyeing the Natural Hair "Tone to Tone" with Oxidative Dyes
When dyeing, the following dyes are used:
ammonia dye;
ethanolamine dye (ammonia-free).
When dyeing natural hair "tone to tone", two problems may arise.
The first problem is that the ammonia dye can raise the natural base (i.e., expose the color present inside the hair—the background, and the hair will become more ginger or redder or yellower, depending on TDL of natural hair).
Lightening background for natural hair:
TDL 3, 4, 5—red prevails;
TDL 6, 7—red-orange and orange-red prevails;
TDL 8—orange prevails;

TDL 9—orange-yellow;

TDL 10—warm yellow lightening background;

Thus, the task is to dye the hair and not affect the lightening background. In the method of translucent hair dyeing, it is done with pH lowering in the hair dyeing mixture to a more acidic side (acidification). Acidification is done with Dyeing Diffusions Type 2:
- oxidizer in larger quantities;
- hair mask;
- special acid-containing solutions.

The second problem is that on natural hair, the color present inside the hair (the lightening background) is already exposed due to exposure to the sun or oxygen. The customer wants to neutralize, i.e. remove, the unwanted red, orange and yellow. However, neutralization leads to a half-tone darkening. Therefore, you should first lighten the natural hair by a tone up and dye them tone to tone.

Thus, depending on the problem, there are two options for dyeing natural hair with ammonia dye "tone to tone".

Example 3.6.1.1

On moist hair, closer to wet, Dyeing Diffusion Type 2 is applied comprising:
- tone-to-tone dye (50 g)+low oxidizer 1% (200 to 500 ml)+regenerating mask with acidic pH (10 to 200 ml)+shampoo (5 to 500 ml)+liquid amino acids (5-200 ml)+oil (2-50 ml)+ silicone (2-50 ml). The exposure time is 7 to 30 minutes.

In this method, the predominance of a low concentration oxidizer and a hair mask is mandatory. It is recommended to add a little shampoo and to strive for the lower limit of the specified range or Dyeing Diffusion Type 2 comprising:
tone-to-tone dye (50 g)+low oxidizer 1% (200 to 500 ml)+regenerating mask with acidic pH (10 to 200 ml)+liquid amino acids (5-200 ml)+oil (2-50 ml)+ silicone (2-50 ml), exclude shampoo; exposure time 7-25 minutes;

Mixture removal: the hair is abundantly washed with water; washed with shampoo for 5 minutes (shampoo pH 5.5 and below); washed with water; a regenerating mask with acidic pH is applied for 10-15 minutes;

Color refinement by translucent hair dyeing. If the color is not saturated enough or has not reached the desired TDL (which is possible due to a highly diluted mixture), neutralizing, pigmenting, artistic or diluted diffusions are used:

"tone-to-tone" dye (10 g)+1% oxidizer (80 ml)+mask (10-200 ml)+shampoo (20 ml), which is applied to the hair shaft, it is advisable not to apply to the scalp; exposure time 7 to 25 minutes with constant mechanical impact by hands; visual control; rinse with water abundantly.

If the process is over, remove the mixture: shampoo for 5 minutes, apply a recovery mask with an acidic pH for 10-15 minutes; rinse with water. If there is a desire to add colors, between the diffusion application, wash the hair with water without removing the mixture;

Color refinement is done if there is a desire to add a color nuance or to remove an undesirable color nuance, for example, to make the color colder.

Diluted diffusion is used: blue mixtone (2 cm)+oxidizer (60 ml)+shampoo (20 ml)+mask (20 ml); exposure time 7 to 25 minutes, with constant mechanical impact by hands; visual control; rinse with water abundantly.

If the process is over, remove the mixture: rinse with shampoo for 5 minutes; apply a recovery mask with an acidic pH for 10-15 minutes; rinse with water.

As it is necessary to lighten only by one tone, it is preferable to use TDL 10 dyes.

Mixture removal: the hair is abundantly washed with water; washed with shampoo for 5 minutes (shampoo pH 5.5 and below); washed with water; a regenerating mask with an acidic pH is applied for 10-15 minutes;

Dyeing with dyeing diffusion:

Tone-to-tone dye (50 g)+cold-color dye (tone-to-tone with blue color, for example)+dye TDL 1.0 (1 to 10 cm)+low oxidizer 1% (100 to 500 ml)+regenerating mask with acidic pH (10 to 200 ml)+shampoo (5 to 500 ml)+liquid amino acids (5-200 ml)+oil (2-50 ml)+ silicone (2-50 ml); exposure time 7 to 30 minutes.

Dye TDL 1.0 must be included, as well as the neutralizing the lightening background is added.

The natural background neutralization means addition of colors opposite to the lightening background: red-green; orange-blue; yellow-blue-purple; orange-red-cyanide (blue-green)

or tone-to-tone dye (50 g)+mixtone of opposite color (2 to 6 cm)+dye TDL 1.0 (1 to 10 cm)+low oxidizer 1% (100 to 500 ml)+regenerating mask with acidic pH (10 to 200 ml)+shampoo (5 to 500 ml)+liquid amino acids (5-200 ml)+oil (2-50 ml)+(silicone 2-50 ml; exposure time 7 to 30 minutes;

Removal of the composition: the hair is abundantly washed with water; washed with shampoo for 5 minutes (shampoo pH 5.5 and below); washed with water; a regenerating mask with an acidic pH is applied for 10-15 minutes;

Color refinement by translucent hair dyeing method can be further used, as needed. If the color is not saturated enough, dyeing is done with diluted or pre-pigmenting, or neutralizing diffusion.

For example, with diluted diffusion comprising: tone-to-tone dye (10 g)+1% oxidizer (80 ml)+shampoo (20 ml). The mixture is applied to the hair shaft, preferably not applied to the scalp. The exposure time makes 7 to 25 minutes with constant mechanical impact by hands. Use visual control, rinse with water abundantly. If the process is over, remove the mixture: rinse with shampoo for 5 minutes; apply a recovery mask with acidic pH for 10-15 minutes; wash off with water. If there is a desire to add colors, between the applied diffusions, they are simply washed off with water without removing the mixture.

Translucent hair dyeing—glaze coating by layers

If you want to add a color nuance or remove an undesirable color nuance, the final glaze coating is done. In this case, the diluted diffusion or diffusion with direct-effect pigment is used.

For example, a light-brown (fair) color was created (it is created using herbal green "green-yellow"). It turned out that this color is not enough to get the desired result. Add a green-yellow mixtone (2 cm), which makes the color more light brown+pink mixtone (1 cm) (makes the color more attractive)+oxidizer 40 ml+shampoo (10 ml)+mask (20 ml). The exposure time makes 7 to 25 minutes with constant mechanical impact by hands. Use visual control, rinse with water abundantly. If the process is over, remove the mixture: rinse with shampoo for 5 minutes; apply a recovery mask with acidic pH for 10-15 minutes; wash off with water. As a result, an accurate "tone-to-tone" hit is obtained.

Make recovery with active agents.

3.6.2. Dyeing the Natural Hair "Tone to Tone" with Direct-Effect Pigments

Dyeing the natural hair "tone to tone" with direct-effect pigments is done as follows:

Direct-effect pigment diffusion is applied to wet hair: direct-effect pigments (50 g)+oxidizer (5 to 200 ml) or direct-effect pigments (50 g)+oxidizer (5 to 200 ml)+oxidative dye (1 cm to 20 cm). The exposure time is 5 to 40 minutes, preferably under heat.

Mixture removal: wash off with cool water, apply a mask, keep warm for 15 minutes; rinse with water.

It is possible to re-apply the mixture, i.e., translucent hair dyeing method can be further used with a direct-effect pigment.

For natural hair dyeing, acid diffusion can be used (see Section "Diffusion compositions used in the claimed method", Part 1).

3.7. Implementation of the Method of Translucent Hair Dyeing According to Option 1

In the method according to Option 1, pre-pigmenting diffusion is used if the natural hair has faded, but you need to get a smooth color. The composition and examples of pre-pigmenting diffusion are stipulated in "Diffusion compositions used in the claimed method", Part 5).

In the method according to Option 1, lightening and pre-pigmenting diffusion is used if the task is to lighten the hair and make the color more red. The composition and examples of lightening and pre-pigmenting diffusion are presented in "Diffusion compositions used in the claimed method", Part 6).

3.8. Implementation of the Method of Translucent Hair Dyeing According to Option 2

The method of translucent hair dyeing according to Option 2 is intended for dyeing the previously dyed hair, with minimal damage to the hair structure.

Frequent previous dyeing makes it necessary to resort to a preliminary removal of the previous dye to achieve the desired result after subsequent dyeing.

The previously dyed hair has a number of features in dyeing. In the claimed method, such a stage as the re-neutralization of the lightening background is important (see the relevant section in the description below). Dyeing with re-neutralization enables the color to no longer be washed out into an undesirable shade and active agents the hair extremely rarely, for example, once every 6 months.

The method of translucent hair dyeing according to Option 2 for dyeing of the previously dyed hair includes the following steps:

Cleansing of hair from dirt and cosmetic pigment;
Removal of the composition from the hair;
Lowering hair pH to a more acidic side;
Neutralization or re-neutralization of the lightening background;
Removal of the composition with water;
Making the substrate, based on the desired result;
Removal of the composition with water;
Hair recovery with active agents;
Dyeing to the desired color;
Removal of the composition with shampoo, then with water;
Hair recovery with active agents;
Color alignment or refinement;
Removal with water;

Final translucent hair dyeing;
Removal of the mixture with shampoo, applying a mask;
Hair recovery with active agents.

Hair cleansing, including from dirt and from direct-effect pigments, is done with shampooing.

In preparation for dyeing according to the claimed method, it is necessary to remove a cosmetic or natural pigment.

Removal of cosmetic pigment from previously dyed hair according to the claimed method is done using dilutions of lightening products. To remove a cosmetic pigment from previously dyed hair, acid diffusion is used in the claimed method (see "Diffusion compositions used in the claimed method", Part 1) with the ratio: acid wash (Stage 1 and Stage 2, where Stage 1 is a reducing composition and Stage 2 is a catalyzing composition) is 50% and shampoo 50%. Use shampoo with pH 5.5 and below. The proportions are different: the range varies from 1 g of Stage 1 acid wash+1 g of Stage 2 acid wash+1 g of shampoo up to 200 g of Stage 1 acid wash+200 g of Stage 2 acid wash+200 g of shampoo. The smaller is the shampoo amount in the mixture, the stronger is the substance concentration to remove the cosmetic pigment; and vice versa, the more is shampoo and less acid wash, the slower the composition operates, as the concentration is reduced, but due to shampoo, it penetrates deep into the cortex.

To bring the acid wash components deeper into the hair cortex, change the mixture concentration and adjust the dilution degree of the acid wash with shampoo. If the dye is not completely removed from hair, acid diffusion is repeated. Using the composition of acid diffusion with a high content of shampoo and a small concentration of acid wash, the hairdresser can apply acid diffusion layers more than once and control the process of pigment removal.

The exposure time of acid diffusion is 5 to 30 minutes, depending on how the cosmetic pigment is removed. Unlike the widely used (hereinafter referred to as the classic) acid wash, the components of acid diffusion penetrate deeper into the cortex than in the classic acid wash, and the time of this procedure within the salon is also reduced.

It is very important that during acid diffusion, the composition is not applied to the scalp, but only to the hair, thereby providing a gentle effect on the hair structure.

The exposure time is visual, it depends on the quality of customer's hair. Before starting the lightening procedure, hair quality is checked with a strand test.

The strand test is performed as follows. Take a classic composition of a lightening product and apply it to a hair strand 3 mm by 3 mm; wrap it in foil; the exposure time specified by the manufacturer, for example, 60 minutes (minimum 15 minutes). It is desirable to take a higher percentage of the oxidizer, for example, if it is planned to remove stripes or completely dark hair shafts with 5% oxidizer, the test is done with at least 6% oxidizer. As the dyeing procedures will be done after exposure to 5% oxidizer, i.e. the effect is chemical, and in total these procedures will give, for example, 6%, hair quality should be checked for it to withstand these manipulations. It is better to perform a strand test at high percentages to be aware of the damage degree done to the hair.

After the strand test exposure time, remove the composition with a wet towel until completely removed and then apply an acidic hair mask for 3-5 minutes. Remove the mask again with a wet towel and check the hair for extensibility. If it tears, the hair needs recovery, and only then discoloration can be made.

The pigmentation strips on the hair are removed by acid diffusion or with a lightening powder diluted with a low percentage oxidizer.

Example 3.8.1

Removal of cosmetic pigments by acid diffusion is done in the following sequence:

The acid diffusion composition is applied to the entire hair shaft or selectively to darkened areas.

The preferred proportions of shampoo and acid wash are 0.5-3.0 parts of shampoo to 3.0-0.5 parts of acid wash. For example:
- shampoo (0.5):acid wash (1);
- shampoo (1):acid wash (0.5);
- shampoo (1):acid wash (3);
- shampoo (3):acid wash (1);
- shampoo (1):acid wash (2);
- shampoo (2):acid wash (1).

The mixing range varies as needed depending on the hair condition and color density (darkness) of the.

Using the mixture composition with high shampoo content and a small concentration of acid wash, the hairdresser applies layers of acid diffusion more than once, controlling the process of pigment removal.

Gradual removal of cosmetic pigment by acid diffusion is less traumatic for the hair. The hairdresser can apply acid diffusion not to the entire hair shaft, but selectively, to individual areas.

Control over the color manifestation on hair is done using a strand test by applying hydrogen peroxide and leaving it for 3-5 minutes. If color darkening is revealed, once again the procedure and a strand test are done until a non-darkened color is obtained, if the hair quality is favorable.

If, as a result of acid diffusion, the pigment on the previously dyed hair shaft is not removed, the removal is done using lightening products: powders, oils, pastes or discoloration diffusion (see Section "Diffusion compositions used in the claimed method", Part 3).

The classic way of hair discoloration with lightening powder: lightening powder, oxide—more often 3% to 12% percent. Ratio: 1 part of powder: 1 part of oxidizer to 1 part of powder: 3 parts of oxidizer.

The exposure time is 20-60 minutes without increasing the temperature regime. This lightening is quite aggressive and destroys the hair structure.

In the claimed method, discoloration diffusion is used for the purpose of removing the pigment, where the ratio of the amount of lightening powder to the amount of oxidizer is 1 part of the lightening powder:1 part of oxidizer to 1 part of lightening powder: 200 parts of oxidizer. These ratios make it possible to make the composition more acidic and work in other pH ranges, which preserves hair quality and increases the exposure time of the powder for better lightening. To increase the stability of this mixture and maintain the degree of lightening, thickeners and active agents are included in discoloration diffusion (see Table 1, Item 3.2).

Example 3.8.2

Removal of cosmetic pigments with discoloration diffusion with active agents in the ratio of components: lightening powder, 1 part+oxide 3%, 10 parts+thickener 10 to 40 ml+liquid amino acids 10 to 60 ml+ silicone oil (demiticone) 5-15 ml+argan oil 5-15 ml.

Other examples of component proportions of clarifying mixture can be any of the above 1 part of lightening powder: 1 part of oxidizer to 1 part of lightening powder: 200 parts of oxidizer with a percentage of 1% to 12%.

Apply a mixture of lightening powder and oxidizer with a thickener and components that protect and restore the hair structure shown above to dark stripes and hair shaft, avoiding contact with the scalp. Insulation with foil, hair shaft towels, etc. is possible. They are left for exposure time is 5 to 180 minutes. Next, the mixture is removed from hair with a paper towel or washed off with water and applied again if necessary, if the desired lightening background has not been achieved and hair quality enables you to lighten further.

Thus, at fairly low percentages, such as: 1%, 1.5%, 2%, 2.5%, etc. up to a higher 12%, it is possible to lighten the hair while maintaining the hair quality.

It is possible to completely remove direct-effect pigments and plant dyes such as henna, basma, etc. from hair with the use of clay diffusion (see Section "Diffusion compositions used in the claimed method", Part 13).

Clay diffusions are used first, as some of the direct-effect pigments will go deeper into the cortex after applying discoloration diffusion, and they will be much more difficult or impossible to remove. Due to alkaline diffusions, these pigments (direct-effect or plant) change their color, for example, from orange to green. Since these pigments are located in the upper cortex layers, the task is solved to remove them first by clay diffusion. Only then the acidic and discoloration diffusion is used.

Example 3.8.3

Clay diffusion comprising: white clay 150 g+water brought to a boil (boiling water) 150 ml+glycerin 5-30 ml is applied to wet, well-pressed hair for 30 minutes under polyethylene and heat t=30-45° C.;

The hair is washed with warm water, closer to hot, t=40-50° C.;

Shampoo is applied 3 times. With each application, the shampoo is driven into the hair cortex, the scalp is not washed; left for 5 minutes; washed abundantly with water t=40-50° C. At the next shampoo application, tap in the shampoo for 5 minutes and rinse with water t=40-50° C.

Example 3.8.4

70% of alcohol is applied to hair, left for 10 minutes, then olive oil (or any oil) is applied. The oil is left on the hair for 20 minutes under heat; then washed with shampoo 2-3 times; then clay diffusion is prepared with the composition: clay 150 gr+water brought to a boil (boiling water) 150 ml+glycerin 5-30 ml;

The clay diffusion is applied to wet, well-pressed hair for 30 minutes under polyethylene and heat t=30-45° C.;

Hair is rinsed with water t=40-50° C.

Shampoo is applied 3 times. With each application, the shampoo is driven into the hair cortex, the scalp is not washed; left for 5 minutes; washed abundantly with water t=40-50° C. At the next shampoo application, tap in the shampoo for 5 minutes and rinse with water.

In the claimed method, the lightening diffusion is used for dyeing preparation, for matching TDL of own hair with TDL of dyed hair and a smooth transition from natural color to the dyed one. The lightening diffusion (2) is used (see Examples 2.1 and 2.2 of Section "Diffusion compositions used in the claimed method"). The diffusion enables you to loosen and lighten the hair better in 10-30 minutes.

Example 3.8.5. A Scheme for Cosmetic Pigment Removal

It is used before hair dyeing as an independent procedure.
1. Acid diffusion—multiple application. Rinsing with water between applications.
2. Shampoo removal. Shampoo repeatedly, three times.
3. Diffusion removal.
4. Color darkening test.
5. Hair recovery.
6. Dyeing is started.

Before applying discoloration or lightening diffusions:
1. Acid diffusion with multiple application. Rinse with water between applications.
2. Shampoo removal. Shampoo repeatedly, three times.
3. Strand test for darkening.
4. Discoloration diffusion or lightening diffusion.
5. Diffusion removal.
6. Hair recovery.
7. Dyeing is started.

Acid diffusion with repeated application before and after discoloration or lightening diffusions.
1. Acid diffusion.
2. Shampoo removal.
3. Strand test for darkening.
4. Discoloration diffusion or lightening diffusion.
5. Acid diffusion—multiple applications.
6. Diffusion removal. Shampoo three times.
7. Strand test for darkening.
8. Hair recovery.
9. Dyeing is started.

or

Acid diffusion with repeated application after discoloration.
1. Discoloration diffusion or lightening diffusion.
2. Acid diffusion—multiple applications.
3. Diffusion removal. Shampoo three applications.
4. Strand test for darkening.
5. Hair recovery.
6. Dyeing is started.

Acid diffusion has four uses.

Application 1 of acid diffusion (1) is the removal of cosmetic pigment before hair dyeing, which will facilitate will facilitate careful removing of a part of the cosmetic pigment without any type of lightening diffusion (discoloration and lightening). This is the best option for hair in poor condition. However, it is a longer process, slower achievement of the result.

Example 3.8.6. Natural Hair TDL7 was Dyed TDL 5 for 2 Years. The Desire is to have TDL7 Again Acid diffusions are made as the following compositions: 20 ml of Stage 1+20 ml of Stage 2+20 ml of shampoo. As applied to the hair, avoid contact with the skin; mechanically rub into the hair for 15-20 minutes; wash off abundantly with water, preferably at the temperature closer to hot.

Repeat the diffusion dilution again and go over the procedure once more. There may be a number of such procedures, depending on hair condition, the absence of allergic reactions to this product and customer's time to spare.

After diffusion completion, the hair is washed three times with a shampoo. Make a strand test for treatment with an oxidizer, and check whether a hair strand is darkened or not. If yes, notice how many tones will be darkened.

After reaching the desired lightening background and based on the tone depth seen after the strand test, dyeing is started.

The dyeing diffusion is applied comprising: dye 7.1+1.5%+reducing agents;

Refinement with diluted diffusion follows.

Application 2 of acid diffusion (1) is the removal of cosmetic pigment before applying discoloration or lightening diffusion, which will facilitate careful removing (compared to alkaline removals) of a part of the cosmetic pigment and preserve hair quality. Acidic diffusions will remove a part of pigment. Therefore, alkaline diffusions (discoloration and lightening) will work shorter to remove the pigment, which will affect hair quality for the better.

Example 3.8.7. Natural Hair TDL7 was Dyed TDL 5 for 2 Years. The Desire is to have TDL7 Again Acid diffusions are diluted as the following compositions: 20 ml of Stage 1+20 ml of Stage 2+20 ml of shampoo. As applied to the hair, avoid contact with the skin; mechanically rub into the hair for 15-20 minutes; wash off abundantly with water, preferably at the temperature closer to hot.

Repeat the diffusion dilution again and go over the procedure once more. After diffusion completion, the hair is washed three times with a shampoo. Make a strand test for treatment with an oxidizer, and check whether a hair strand is darkened or not. If yes, notice how many tones will be darkened.

After reaching the desired lightening background and based on the tone depth seen after the strand test, dyeing is started as in the first diffusion application or make dyeing with neutralization. The sequence of operations:

Making the substrate with neutralizing diffusion;

Application of dyeing diffusion comprising: dye agent TDL 7.1+1.5%+reducing agents;

Refinement with diluted diffusion.

If the desired lightening background has not been achieved, discoloration diffusion is applied; and only then we proceed to neutralizing, dyeing, diluted and other diffusions intended for pigment introduction.

Application 3 of acid diffusion (1) is cosmetic pigment removal with acid diffusion before and after discoloration or lightening diffusions.

Example 3.8.8. Natural Hair TDL7 was Dyed TDL 5 for 2 Years. The Desire is to have TDL7 Again Acid diffusions are made as the following compositions: 20 ml of Stage 1+20 ml of Stage 2+20 ml of shampoo. As applied to the hair, avoid contact with the skin; mechanically rub into the hair for 15-20 minutes; wash off abundantly with water, preferably at the temperature closer to hot.

Repeat the new diffusion dilution and repeat the procedure again. At the end, a test is done with an oxidizer to darken TDL.

If the desired lightening background has not been achieved, discoloration diffusion is applied. Remove the discoloration diffusion from hair.

If you have not reached the desired TDL, acid diffusion is applied again.

Dilute 20 ml of Stage 1+20 ml of Stage 2+20 ml of shampoo. As applied to the hair, avoid contact with the skin;

mechanically rub into the hair for 15-20 minutes; wash off abundantly with water, preferably at the temperature closer to hot.

If necessary, repeat the required number of times.
   Remove the mixture with water.
   Wash the hair abundantly with shampoo three times.
   Apply a mask.
   Dyeing is started.

Example 3.8.9. Natural Hair TDL7 was Dyed TDL 5 for 2 Years. The Desire is to have TDL7 Again 1) Apply acid diffusion to hair, avoiding contact with the scalp. Perform this procedure 3 to 8 times, leaving each diffusion for 10-15 minutes and rubbing it into the hair. Between diffusions, they are washed with warm water, closer to hot. At the end of all acid diffusions, they are washed with shampoo three times. Then make a strand test: choose one strand of 1 cm by 1 cm and apply oxidizer 3% for 3-5 minutes. Wait for the color to darken. Darkening may not happen. For example, before diffusions there was TDL 5 cosmetic base, it became TDL 6. The desire is to have TDL 7 cold, therefore, it is necessary to lighten the hair to TDL 8, because neutralization will provide darkening by a tone, and as a result, you will get a cold TDL 7.

2) Apply the discoloration diffusion comprising: 50 g of lightening powder+oxidizer 1% (1000 ml)+liquid amino acids (5-200 ml)+oil (2-50 ml)+ silicone (2-50 ml)+thickener (2 to 100 ml) on wet hair, avoiding contact with the skin. The exposure time is visual, maximum 50 minutes. If necessary, it is applied to the skin according to the manufacturer's recommendations and manufacturer's dilution proportions. Remove the mixture, first washing off with water abundantly, then with shampoo. The result is lightening of TDL 7.5.

3) Hair recovery is done.

4) Application of acid diffusions.

Apply acidic diffusions to hair, avoiding contact with the scalp. Perform this procedure 3 to 8 times, leaving each diffusion for 10-15 minutes and rubbing it into the hair. Between diffusions, they are washed with warm water, closer to hot. At the end of all acid diffusions, they are washed with shampoo three times. Then make a strand test, choosing one strand of 1 cm by 1 cm and apply oxidize 3% for 3-5 minutes. Wait for the color to darken. As a result, TDL 8.5 is obtained. Remove the oxidizer from the strand.

The pigment has been removed. If desired, you can continue the diffusion and remove more pigment and make the hair smooth lighter, but in this example there is no such task.

5) The substrate is made with a neutralizing diffusion: neutralizing dye, 1 part+mixtone from 0.5 cm to 50 cm+1% to 9% oxidizer in the ratio dye: oxidizer from 1:1 to 1:30 (2 to 300 ml preferably)+shampoo 2 to 300 ml.

Composition: TDL 8.1+green mixtone (3 cm)+80 ml oxidizer+10 ml shampoo.

6) Dyeing diffusion:

Dye agent TDL 7.1, 50 g+1.5% oxidizer, 80 ml+amino acids+oils+mask. Exposure time 10-30 minutes.

7) Final translucent dyeing with diffusion with direct-effect pigment.

Direct-effect pink pigment (5 cm)+mixtone pink (3 cm)+ oxidizer 40 ml+20 ml shampoo+20 ml mask.

Acid diffusion applied after discoloration or lightening diffusions provides a stronger removal of cosmetic pigment. Thus, it is possible to remove the dark cosmetic color on the hair quality when it is no longer possible to work with discoloration diffusions (hair will fall off). The acid diffusion will provide pigment removal on this hair and leave it on bearer's head. Moreover, sharp jumps in pigment removal were noted when acid diffusion was applied after the application of alkaline diffusions. If you treat hair with discoloration diffusion again, and then remove it from hair, and make an acid diffusion application again, there will be a jump in pigment removal.

At the end of the procedure, the hair is abundantly washed with shampoo. A strand test is made for treatment with an oxidizer to check for color darkening. The actually obtained TDL after the oxidizer is evaluated. The oxidizer is washed off with water, and dyeing diffusions are started. The sequence of operations:

Making the substrate with neutralizing diffusion;
   Application of dyeing diffusion comprising: dye agent TDL 7.1+1.5% oxidizer+reducing (active) agents;
   Refinement with diluted diffusion.

Application 4 of acid diffusion (1) occurs after a complete, 100% neutralization.

To ensure that the lightening background of dyed hair or the lightening background of the natural base do not distort the desired color, and the desired color to last for a long time and not to wash out into an undesirable one, a 100% neutralization or re-neutralization procedure is done. It means adding more of the opposite color and overflowing with the opposite color, as described in detail in Section "Re-neutralization".

During neutralization, there is a strong TDL darkening, but this darkening is temporary and is washed out gradually from customer's hair within 3 to 30 days. After neutralization, a part of the pigment is removed by acid diffusion.

Application 4.1 of acid diffusion (1). The author tested and noticed the following. Acid diffusion blurs the final color, leaving it, but making it lighter, although in hairdressing community it is believed that acid washing removes the pigment completely. Acidic diffusion first blurs the color, and then removes it completely. This borderline can be caught, which is what diffusion enables.

For example, if you take an acid wash, 5 ml (Stage 1)+acid wash, 5 ml (Stage 2)+40 ml of shampoo, you will get a very diluted diffusion that will lighten the final color slowly and gradually.

If necessary, you can increase the concentration of acid diffusion: acid wash 10 ml (Stage 1)+acid wash 10 ml (Stage 2)+30 ml of shampoo. Such diffusion will start working faster. It is necessary if the color is dark or saturated, i.e. there is more of it than needed in quantity.

As a result of the processes of natural pigment oxidation (sunlight) and chemical oxidation (lightening dyes, hair powders), hair colors become warmer. The lightening background appears, because the natural pigment, oxidizing, becomes warm (from red to warm yellow). The background lightening colors are different in all people, because hair has a different set of eumelanin and pheomelanin.

To obtain a predictable and maximally smooth color when dyeing according to the claimed method, it is necessary to make a preliminary dye application by pre-pigmentation and substrate application.

3.8.1 Alignment of Hair Shaft by Quality and Color

The hair shaft alignment according to hair quality is done by hair recovery using active agents.

Color alignment is done by adding the missing colors to the damaged hair areas.

At the same time, the lightening background is replenished with warm-color pigments with simultaneous hair structure recovery.

To add a warm-tone pigment to hair cortex, from where it was artificially removed with discoloration preparations, pre-pigmenting diffusion (5) is used (see Section "Diffusion compositions used in the claimed method", Part 5).

Pre-pigmentation is introduction of warm shades by using oxidizing pigments. It is not desirable to do it with direct-effect pigments, as the stability of these dyeing molecules is much lower than that of oxidizing ones. Direct-effect pigments do their best on the surface of hair that has been dyed with oxidizing pigments. However, it is possible to lay direct-effect pigments first or mix them with oxidizing ones.

3.8.2. Color Alignment

According to the claimed method, pre-pigmentation, neutralization, i.e. alignment of the hair shaft by color, is done with creating a color base for optimal manifestation of color applied over the base. Alignment can be done both by pre-pigmentation and neutralization.

The author revealed in practice that the alignment must be performed jointly with hair recovery, otherwise, the result will be extremely unstable, and the colors of dyes or mixtones that it will be done with will directly depend on the degree of damage done to hair and on the result that the customer wants to get. The more hair is destroyed, the warmer—red or red-orange pigment—is needed. The healthier is the hair, the more yellow, orange, and orange-red pigments will be preferred.

To obtain a predictable and maximally even color when dyeing according to the claimed method, it is necessary to saturate the hair with pigment, i.e. to create a special color base on hair—a "substrate", on which the manifestation of the color applied onto it will be optimal.

The main task of this dyeing stage is to create a "substrate" on hair matching the color or neutralizing it, and make it in such a way as to fill the hair structure with a pigment close to natural, or to neutralize the residuals of the natural pigment if it interferes with the desired color build up, with parallel recovery of the hair structure. It is a high-quality pigmentation that ensures the accuracy of the selected shade.

There are known methods of pre-pigmentation used in salons. According to one technique (http://cosmetic.ua/repigmentatsiya), the hairdresser applies a water-based composition enriched with yellow, orange, red pigment or a combination thereof onto hair, and immediately after that— an oxidizer mixed with ammonia dye (a durable dye). The effect of any durable (ammonia) dye is that a mixture of hydrogen peroxide (oxidizer) and ammonia contained in the dye opens the hair cuticle scales, "opening the gate" for the dye pigment. Thus, artificial pigments for dye retaining and dye pigments simultaneously penetrate into the hair, providing a lasting dyeing effect.

However, this pre-pigmentation does not provide for hair recovery and care as a result of the procedure, and does not take into account the individual features of customer's hair.

According to another known technique, a ready-made pre-pigmentation compound is applied by a thin layer either to the entire hair or only to light areas that need to be darkened. All excess compound is removed from hair with a disposable towel or a napkin Immediately, a dye of the selected shade is applied on top, and each strand is carefully emulsified, so that the dye can easily penetrate into the hair. This method also does not provide for hair recovery and care. Emulsification is done only for the depth of pigment penetration. The individual features of customer's hair are not taken into account.

The classical pre-pigmentation method is designed for a higher pH range and, as a result, a more severe hair destruction and absence of color stability during wear, i.e. an unstable result. Hair recovery is not provided before applying the mixture.

A high percentage of oxidizer+plus dyes with high TDLs (10, 9, 8) give a total lightening response simultaneously with pre-pigmentation reaction. In case the hair is destroyed, it is not provided for adding red color at high TDLs (for blondes).

Under the claimed method, pre-pigmentation is done with simultaneous hair structure recovery and with the possibility of gentle and gradual application of dyeing composition onto hair by a thin layer, with gradual filling the hair structure with pigment and active agents.

The substrate enables to visualize color fall-outs and irregularities in hair structure. Using a substrate, you can increase the amount of color needed to build up the target color. The color should be added where necessary, since due to the substrate (pre-dye) color absence will become noticeable.

The substrate base composition comprises a mixtone or a dye or a dye+a mixtone with an oxidizer. At the same time, the tone level depth (TDL) of the dye agent should be taken with a low oxidizer percentage: 1%, 1.5%, etc. The oxidizer percentage may be higher if the hair is not destroyed, and the goal is to bring color more deeply into the cortex, then the percentage, on the contrary, is taken higher: 6%, 9%, etc.

For example, to get a TDL 8 tone, TDL 5, 6, 7 tones should be taken and blurred with an oxidizer and shampoo to TDL 10, and then, a substrate should be made. The substrate can be tone-to-tone, but then color darkening will occur.

The substrate base composition comprises mainly: dye, or/dye+mixtone or/mixtone+oxide, and/or shampoo, and/or mask, and/or thickener.

Introduction of active agents, such as shampoo (surfactant) into the dyeing composition of the substrate, that acts as an emulsifier for easy pigment penetration into the hair structure or mask, or a thickener, the amount of which depends on the dye mass and the desired color, enables for gentle and gradual application of the dyeing composition to hair by a thin layer, with gradual filling the hair structure with pigments and active agents.

At the same time, the author evidences for a greater effectiveness of mechanical action when substrate layers are applied not with a brush, but with hairdresser/s fingers. Tactile impact enables the hairdresser to better feel hair density and product sufficiency. Application without the use of a brush facilitates fast composition application to all hair. The hair is simultaneously impregnated and massaged, which contributes to a faster and deeper penetration of the product into the hair structure.

The substrate composition is applied onto hair by a thin layer; left for a while; and washed off. In case of color irregularity or an undesirable shade, repeat application of the substrate layer onto dense hair with composition adjustment, followed by leaving and rinsing until the desired even color is obtained along the entire length of the hair shaft. The more damaged is the hair, the greater number of substrates you need to make. Each substrate shows where and how much color to put or to add.

As a result, a color aligned along the entire length of the hair shaft should be obtained.

The substrate can be neutralizing, as described below, or it can be performed before the main dyeing, i.e. the desired color. The substrate is not done if the hair shaft, as a result of preparation for dyeing, is satisfactory by color and quality.

Example 3.8.2.1. Alignment by Pre Pigmentation on the Mask

Recover the hair in any known method. For moisturizing, a nourishing hair mask is abundantly applied to wet hair. For 15 minutes they are being combed, and the mask is tapped in with hands (movements along cuticle growth from top to bottom), then covered with a film and left at the temperature of 25° C.-40° C. for 15-30 minutes.

Then pre-pigmenting diffusion is applied (see Section "Diffusion compositions used in the claimed method", Part 5) on damaged hair for alignment, preferably the lowest possible depth levels of dye tones (i.e. dyes 8 and below to 5) and the purest colors, i.e. without brown (natural) color—mixtones: red warm, red-orange, orange-red, orange and yellow golden.

The composition of pre-pigmenting diffusion depends on the degree of damage done to hair: the more destroyed is the hair, the more color should be taken. Dyeing is done with a mixture of dye and mask to lower pH and add moisture and lipids to hair.

Example 3.8.2.2. Pre Pigmenting Diffusion for Warm Color Alignment

Mixtone (of warm colors, as indicated above) from 1 cm to 10 cm+dye (from TDL 5.555, where 5 is warm red, 5.45 is orange-red, 5.54 is red-orange; 545; 5.44; 5.43; 5.34; 5.33; 6.55; 6.54; 6.45; 6.44; 6.43; 6.34; 6.33 etc.) on TDL 7 and up to 8. It is not advisable to take TDL 9 dye agent, as it has a fairly high percentage of alkali (i.e. it is created to lighten the hair), and it is required not to destroy, but to restore hair;

Mixtone can be added to the dye, from 1 to 20 cm, an oxide of the lowest concentrations of 1%, 1.5%, in extreme cases—2%. The ratio of dye to oxide is from 1:2 to 1:50. The proportions of the oxidizer are chosen based on mixtone density. Since the oxide has an acidic pH, it is added in larger quantities, to be able to dye within pH range from 4.5 to 6.

A mask from 10 ml to 50 ml can be introduced into the composition, not more than 30% of the mixture.

Example 3.8.2.3

Pre-pigmentation composition: mixtone, 3 cm+dye TDL 6.34, 1 cm+oxide 60 ml+hair mask 25 ml.

Another example of a pre-pigmentation composition: mixtone, warm red, 0.5 cm+dye TDL 6.55, 5 cm+oxide 30 ml+mask 10 ml.

A specialist in this area will realize that the proportions may vary depending on dyeing conditions.

A dye or a mixtone mixed with water can be used for pre-pigmentation.

The ratios with water can be different, depending on the color density of the mixtone or dye and the desire for hair lightness (the depth level of customer's hair tone).

Example 3.8.2.4. Pre Pigmentation with Water and Amino Acids

Pre-pigmenting water diffusion comprises: dye TDL 6.34+water+amino acids, with a ratio of 1:10 (1 part of the dye, 10 parts of water+5 parts of liquid amino acids). The composition is applied to pre-washed hair and the recovery procedure with a mask is done (as described above). The exposure time is 10 to 60 minutes. Then, an oxidizer is applied for 10-15 minutes, and the hair is washed. Do the recovery procedure with a mask again, and, if there is not enough color, repeat the pre-pigmentation procedure with water. Then dyeing within the range of low pH is started. Components for hair recovery (amino acids, oil, glycerin, etc.) are added to the dyeing composition.

This composition enables not only to bring in the necessary pigment (a pure color that is exactly coloristically required), but also to restore the hair by layers (with masks and active additives to dyeing composition). Besides, dyeing with water reduces the pigment oxidation time. The hair gets saturated with a pigment, and only after it the pigment manifests (the molecule becomes larger, and the color appears).

3.8.3 Neutralization of the Lightening Background of Previously Dyed Hair

Neutralization is bringing any colors to neutral, i.e. gray. The main task of neutralization is to "remove" any unwanted colors, to neutralize with opposite colors according to the color wheel.

This stage is intended to neutralize the lightening background of the natural base, to neutralize cosmetic colors (pigments introduced from the outside into the hair) using neutralizing diffusions.

The main feature and difference from neutralization of undyed hair is that you need to add two lightening backgrounds (LB): natural base LB (natural hair TDL)+cosmetic base LB (dyed hair TDL).

Scheme 2.1 Manifestations of Lightening Background for Various TDLs

Natural base:
TDL 3, 4, 5—red;
TDL 6—red-orange; orange-red; red-red (the difference in shades is related to a genetic factor—a different set of hair pigments);
TDL 7—red-orange; orange-red; orange-orange; orange-yellow;
TDL 8—orange-orange-yellow; orange; orange-red;
TDL 9—yellow-orange; yellow; yellow-yellow; orange-yellow;
TDL 10—light yellow; yellow.

Cosmetic base:
TDL 1, 2, 3, 4, 5—red;
TDL 6—red-orange; orange-red; red-red;
TDL 7—orange; orange-red; orange-orange; orange-yellow;
TDL 8—orange-orange-yellow; orange; orange-red;
TDL 9—yellow-orange; yellow; yellow-yellow; orange-yellow;
TDL 10—light yellow; yellow;
TDL 11—light-light yellow.

Thus, it is necessary to combine the cosmetic base colors with the natural base colors.

For example, the customer has natural hair TDL 7 (light brown), dyed for 2 years (24 months, every month) in TDL 5.0. LB natural TDL 7—orange. LB cosmetic TDL 5—red color. Add orange+red.

The customer often dyed, so there is more cosmetic pigment than natural in the hair shaft. Therefore, there is more red color and less orange comprised. Let's say, the customer's color is red-red-orange. Neutralization in this case is done as follows.

Scheme 2.2 Neutralization of the Lightening Background
TDL 1, 2, 3, 4, 5—neutralized with green emerald;
TDL 6—with green-blue;
TDL 7—with blue-green;
TDL 8—with blue-blue-green or blue;
TDL 9—with blue-purple;
TDL 10—with blue-purple.

In the example under consideration, the natural base of TDL 7+a larger amount of cosmetic base TDL 5. A decision is made to neutralize red-red-orange with green-green-blue-green.

The task is to apply these colors to hair and to wait for gray or slightly dim red and orange in the lightening backgrounds, if the customer wants to exclude these colors.

For previously dyed hair, neutralizing diffusion (7) is preferably performed with a large amount of mixtones and with less dye, since the dye contains more unnecessary color bases.

Neutralizing diffusion comprises: a light-tone dye TDL 9 or TDL 10+a mixtone of neutralizing color from 0.5 cm to 50 cm+1% to 9% oxidizer in the ratio dye: oxidizer from 1:1 to 1:30 (2 to 300 ml preferably)+shampoo from 2 to 300 ml.

TDL 9 or TDL 10 dye is taken as a transport to transfer the necessary color deeper into the cortex.

The exposure time is determined visually, until the desired color is reached or reduced to neutral gray. Remove the mixture with water. If there was contact with the scalp, rinse with shampoo, water and start hair recovery.

3.8.4. Neutralization with Water and Amino Acids

Neutralizing water diffusion comprising: neutralizer dye+mixtone 1 to 4 cm+water+amino acids, with a ratio of 1:10, where 1 part of the dye, 10 parts of water+5 parts of liquid amino acids. The composition is applied to pre-washed hair and completed recovery procedure with a mask (described above). The exposure time is 10 to 60 minutes. Then, an oxidizer is applied for 10-15 minutes, and the hair is washed. Do the recovery procedure with a mask again and, if there was not enough neutralization, repeat the neutralization procedure with water. Then start dyeing in the range of low pH+add components for hair recovery (amino acids, oil, glycerin, etc.) to the dyeing composition. This composition enables not only to bring in the necessary pigment (a pure color that is exactly coloristically required), but also to restore the hair by layers (with masks and active additives to dyeing composition). Besides, dyeing with water reduces the pigment oxidation time. The hair gets saturated with a pigment, and only after it the pigment manifests (the molecule becomes larger, and the color appears).

Further, when the hair shaft has become smooth, hair recovery is done.

When neutralizing the lightening background (LB) of cosmetic and natural base of previously dyed hair, the following cases may occur:

Case 1. There is no need for neutralization.
Case 2. Partial neutralization.
Case 3. Complete neutralization.
Case 4. Re-neutralization.
Case 1. There is No Need for Neutralization.

It is possible if the lightening background, i.e. the color of cosmetic or natural pigment does not distort the desired final color.

For example, LB of the cosmetic pigment is red, and the natural pigment is orange. When they are added together, they give red-orange or orange-red, depending on which color prevails in hair cortex, depending on frequency of hair dyeing (the more often the hair was dyed, the more is cosmetic pigment amount).

Another example, when there is no need for neutralization: LB of the cosmetic pigment is red-orange, and the desired final color is red-orange.

Another example—when LB is golden, and it will serve as a substrate to create a more intensive golden color.

Case 2. Partial Neutralization

Partial neutralization is needed when LB slightly interferes with creating the desired color, or when it is evident that LB will manifest over time.

Example: LB is red-orange, you need to create a color on an orange base. The red color will interfere. Neutralize the red color with green, until gray color is obtained. There remains orange-gray, on which the desired color is created. It is partial neutralization.

Case 3. Complete Neutralization

Complete neutralization is necessary when LB interferes with creating the desired color or when the color in LB should not wash out for a long time.

Example: The task is to put 100 molecules of a green lightening background (LB) on 100 molecules of a red background to obtain a neutral color. Complete, 100% neutralization always provides gray color. Then a color is created on the gray base. It should be borne in mind that in this case the neutralizing color molecules will be quickly washed out, in this case, green. As a result, 30% of green color will be washed out within the first 1.5-2 weeks. Over time, there will emerge a part of red that has remained without green color.

Case 4. Re-Neutralization of the Lightening Background

Re-neutralization is necessary when LB should be neutralized and not washed out anymore. For re-neutralization, colors are added that are opposite to LB colors. For example, green-blue is added to the red-orange LB, until the hair becomes green-blue.

Then, part of green-blue color is removed by acid diffusion, and the desired color is created.

Re-centralization in practice was invented by the author and tested for several years.

Since within the first 1.5-2 weeks after dyeing, 30% of color is washed out if the customer washes his hair every other day, the desired color is leached into an undesirable one and as a result, after 2-4 weeks the customer has a hair color that he did not want. It happens after the removal of cosmetic pigment or dyeing with a dye with a high percentage of oxidizer, or simply after frequent dyeing.

Re-neutralization eliminates leaching into an undesirable shade, and enables the color to "manifest" within 2-30 days. The resulting desired, beautiful, and persistent color is provided to the customer for long 2-6 months.

Re-neutralization is a deliberate hair oversaturation with neutralizing colors: blue, green, blue-green, light warm-green, and blue-purple. For example, 150 green molecules of green can be put on 100 red molecules, Thus, you do not need to wait until some green molecules are washed, but can remove the resulting color.

Re-neutralization is made:
to increase color fastness;
for long-term non-leaching into an undesirable shade (i.e., hair dyed in this manner will no longer become warm after 2-6 months to one year.)
to create even cool shades.

The re-neutralization process is done with diluted diffusion, but the amount of oxidizer is shifted to a smaller side, because the mixtone color should be saturated.

The diffusion composition can be borrowed from Section "Diffusion compositions used in the claimed method", Example 11.3.

The diluted diffusion contains only a mixtone+oxidizer. The amount of mixtone from 1 to 100 cm prevails; the amount of oxidizer is maximum 40-300 ml. Besides, shampoo is added in the amount of 2 to 50 ml for a deeper penetration and better distribution.

As a result, the hair should be completely blue or green, etc.

There are two ways to continue:

It can be dyed in the desired color, given that it will turn out to be darker by 1.5-2 tones;

It can be returned to gray or beige, warm beige with other opposite colors. It is also performed with Diluted Diffusion 11.3 comprising of only a mixtone+oxidizer. The amount of mixtone 1 to 100 cm prevails+oxidizer, maximum 40-300 ml+shampoo, from 2 to 50 ml for a deeper penetration and better distribution.

Scheme 2.3 Neutralization of Shades blue_orange
blue-green_orange-red
green_warm red
warm green_purple
yellow_blue-purple
emerald_magenta (red-red-purple)

Only after this procedure the hair can be dyed into the desired color using dyeing diffusions.

The dyeing diffusion composition can be taken from Section "Diffusion compositions used in the claimed method", Example 4.1. Dyeing diffusion with shampoo includes any dye (1 to 9 TDL)+oxidizer (1% to 9%), in the ratio of dye: oxidizer (1:2 to 1:6)+shampoo (2 to 300 ml).

The dyeing diffusion composition can be taken from Section "Diffusion compositions used in the claimed method", Example 4.2 Dyeing diffusion with mixture enrichment without shampoo.

Composition: Dye+oxidizer+liquid amino acids+jojoba oil or others+fish oil.

Proportions: oxidizer+dye (as specified by the manufacturer) for example 1:1, options 1:2 or 1:3 to 1:10 are possible. 1% to 9% oxidizer; amino acids are possible from 5 to 60 ml; oil from 5 to 60 ml; fish oil from 5 to 30 ml. The composition is applied on hair; then refinement is done with diluted diffusion.

Example 3.8.4.1. Hair was Dyed for 8 Years TDL 1.0—Black. The Desire is to have a Lighter Tone so that there is No Warm Shade, and the Color would not Leach into a Warm One Sequence of Diffusion Application:
Step 1. Acid diffusions (up to discoloration).
Step 2. Discoloration diffusions.
Step 3. Acid diffusions (after discoloration).
Step 4. Re-routing.

Diluted diffusion composition: 20 cm emerald mixtone+oxidizer 1% 50 ml+shampoo 20 ml.

The green color (emerald mixtone) is taken, as the lightening background 1.0 is red, the task is to remove the red completely. The oxidizer is the lowest 1%, because the hair after discoloration diffusion is damaged, and the cuticle is maximally opened. Thus, even a low oxidizer percentage will bring neutralization deep into the cortex.

Step 5. Return to gray with magenta and diluted diffusion.

If you need to increase the alkalinity, take the dye as an alkaline base.

Diffusion composition: dye TDL 10.0, 2 cm+5 cm magenta+60 ml oxidizer+30 ml shampoo.

The exposure time is visual. Green is watched to turn into gray. The mixture is removed (if overexposed, the tone will begin to turn pink, and hair may turn pink if the concentration and TDL magenta are concentrated).

Step 6. Creating the main desired color, for example TDL 6.11 (cold ash-blond)

Dyeing diffusion with mixture enrichment, composition:

Dye TDL 6.1, 60 g+1% oxidizer 80 ml+amino acids 20 ml+oil 20 ml+fish oil 20 ml. The exposure time is 20-30 minutes. The mixture is removed.

Step 7. Refinement. Perhaps, there was not enough dye TDL 6.1 or a colder color was desired. In this case, it can be modified by artistic diffusion comprising: dye TDL 6.1, 20 g+oxidizer 40 ml+shampoo 40 ml, applied for 7-30 minutes. Separately, a blue mixtone (5 cm) is diluted+oxidizer 100 ml.

Add the mixture to the hair, to the already applied artistic diffusion composition.

The exposure time is visual.

As a result, TDL 6.11 color is obtained, which will stay on hair for many months and will no longer be leached to red.

3.8.5 Hair Structure Recovery

Hair structure recovery procedure is as follows.

The composition is applied to wet hair: gelatin+glycerin, amino acids (or hydrolyzed keratin), collagen, various oils, fish oil, etc. Gelatin acts as a component carrier and a hair restorer, increasing the area of dye pigment attachment, i.e. fills voids in cortex and intercuticular space. The composition is left on hair under heat and preferably with water vapor for 20-30 minutes. Then rinse it with warm water.

The next hair recovery step, depending on the type and structure of customer's hair, is performed with various chemical compositions prepared in the salon or ready-made formulations of various brands are used.

For curly hair, it is preferable to apply more moisture and lipids: wheat proteins, hydrolyzed silk, glycerin, fish oil, panthenol, everything on a fatty base (such as BTMS emulgator). Amino acids and elastin are required in smaller quantities. Apply the composition to wet hair and leave for 15-30 minutes under heat and steam. Sometimes, when the hair is severely damaged, you can add substances by layers, i.e. apply each substance separately, and leave the hair under the vaporizer for 10 to 30 minutes. It takes longer, but gives better results.

For straight hair, protein and moisture are preferred: amino acids, elastin, collagen, oils, various masks and polyaquanteriums (silicones and polymers). The main thing is to create the necessary substrate density from active additives and restore the hair structure;

Masks are applied by hair type, combed and tapped in for 10-15 minutes.

Then, dyeing is done either on the mask or the hair is slightly washed with water and dyeing is performed on wet hair with low mask content.

We obtained a hair shaft aligned only on sites where there is no pigment, but on the same hair shaft there may be areas darker by TDL that need to be lightened to align the hair shaft by color along the entire length. Lightening in salons is executed either with a dye (special blonds) or with discoloration preparations.

According to the invention, dark areas on hair shaft are lightened using discoloration diffusion.

Since all people, depending on the available natural pigment, the natural base rises, i.e. the natural pigment is oxidized, and the color becomes warmer (reddish, yellowish, in different ways), lightening should be done based on the rule: the darker is the natural base, the more dye in the mixture and less shampoo and oxidizer shall be added.

3.8.6 Dyeing to Create Complex Colors

The dye can be found with shampoo and oxidizer in proportions 1:1:1.

These proportions may vary depending on the desired result from 0.02 g to 200 g. For example, dye 2 g+oxide 20 ml+shampoo 200 ml, or dye 50 g+oxide 100) ml+shampoo 5 ml.

The resulting color is the lightening background. The lightening background (LB) is the color expression of melanin after oxidation, which has been preserved inside the hair shaft. As a result of lightening, the color remains from red to warm yellow tones. By their combination, the lightening background is estimated in classical dyeing.

Under the claimed method, estimation is made based on the natural hair base, i.e. what color prevailed before the lightening process.

For example, in natural hair TDL 3 red pigment dominates; in TDL 6—red-orange or orange-red, or red-red-orange, or orange-orange orange-red and other sets, depending on the genotype; in TDL 8—orange and in TDL 10—yellow pigment prevails.

The next step in the claimed method of hair dyeing is to neutralize the resulting lightening background or existing undesirable color after dyeing on the hair with the opposite color to obtain a neutral, gray color, to spread the desired color on it with a predictable result.

The rules for neutralizing shades are based on the rule of combining mutually absorbing colors (a subtractive system of mixing colors, absorption of different wavelengths and reflection of certain ones. See: https://studopedia.net/2_15548_additivnaya-i-subtraktivnaya-sistemi-smesheniya-tsvetov.html. Published 2 May 2018). In the color wheel (Munsell Color Wheel), these colors are located opposite each other: red opposite green, blue opposite orange, yellow opposite purple. When mixed, they give a neutral color.

The author came to conclusion that it is necessary to neutralize not what is visible as a result of lightening, but what is genetically embedded in the hair structure. For example, a person was born with a dark color, and the pigment in hair is genetically red. If you lighten this hair to blonde, yellow will be visible, and this is scattered red. If you neutralize yellow, then the dyed hair will be constantly washed into yellow. If you neutralize it in green, then the color will never be leached again.

After the stage of lightening background neutralization, the desirable color is applied.

Below is an example of creating a complex color comprising different layers and mixes of different colors.

In classical dyeing, to create a complex color, a number of dyeing procedures are required to create the desired color.

Using the claimed method, it is possible to create a complex color at once, with an accurate getting into both color and brightness according to TDL.

A Scheme for Creating a Complex Color

Step 1. Create on the hair shaft the color of the necessary TDL (lightness).

Step 2. Create the desired color with pure local colors with mixtones or direct-effect pigments. Colors: blue, purple, red, pink, green, cyanide, yellow, orange and their combinations.

Step 3. Add gray color (it is a common diluted black with hairdressers, or gray mixtones and direct-effect pigments)

After Step 3, go back to Steps 2 and 1. Since gray mutes other colors, and the hair has a voluminous structure, it is almost impossible to calculate the right amount. Therefore, the hair is again saturated with pure colors. Since at Steps 2 and 3 hair has TDL, not to darken it, add colors with diluted oxidants (as in diluted diffusion). You can use acid diffusions (and lighten TDLs).

Step 4. Add brown. Brown greatly distorts the created color and makes it more natural, it also adds depth to color and, as a result, darkens it.

Step 5. Go back to Step 2, and then to Step 1.

Thus, you can get into any desired color and create a complex color on a volumetric hair shaft. This is the author's way of creating colors, and three factors play an important role in it:

Pure color TDLs (adding a large number of oxidizer parts to mixtones and direct-effect pigments);

Acid diffusion that blurs the color saturation, completely preserving all color nuances;

The possibility to obtain the desired color after a single visit to the hairdresser. The most important thing is that on a volumetric structure, such as hair, it is almost impossible to create a complex color at once, comprising many colors and nuances, at different cortex levels. In the claimed method, you can put a sufficiently dark color and blur it, and apply another color on top and also blur it, etc. Thus, the color is achieved within one visit to the hairdresser. With classical dyeing, it would take at least six months.

Also, in the claimed method, it is possible to combine lightening diffusion with dyeing diffusions (neutralizing, pre-pigmenting, etc.).

Example of Application of Neutralizing and Lightening Diffusion (8) on Previously Dyed Hair.

On previously dyed hair, there is a cosmetic strip TDL 7.43 (orange-gold). You need to make it lighter by tone and replace the warm color with a cold one.

A neutralizing and lightening diffusion is applied to the strip comprising: dye TDL 12.1 (20 cm)+TDL 7.1+mixtone blue-green (4 cm)+oxidizer 9% 120 ml+shampoo 20 ml. They are left for 20 minutes. Remove the mixture.

If this diffusion failed to achieve lightening by one tone, acid diffusion is performed. Rinse with shampoo several times, then rinse with water, apply a mask.

A dyeing diffusion is applied comprising: dye TDL 8.1+oxidizer 1.5%, 1:1.5+shampoo 20 ml. They are left on the hair for 7 to 30 minutes.

Advantages:

Neutralizing and lightening diffusion reduces the time of hair lightening and dyeing. In the claimed invention, the time of hair lightening and dyeing takes 7 to 30 minutes; in the salon −50 minutes.

The proposed method enables you to achieve neutralization on any kind of hair and perform it 100% accurate (to get into gray); it also enables you to visually control the color.

The exact amount of neutralizing mixtone can be calculated.

It is possible to penetrate deep into the hair by lightening and simultaneously and deeply as well to lay the background neutralization.

Step 6. Lightening and pre-pigmenting diffusions on previously dyed hair are required only for dyeing gray or previously dyed hair in warm colors and for lightening.

For example, the hair had been dyed before, it has TDL 8.54 (5—red, 4-orange); the desire is to have TDL 9.44.

Lightening and pre-pigmenting diffusion comprises: dye TDL 12.3 (9 cm)+TDL 9.44+orange mixtone (2 cm)+oxidizer 6%, 120 ml+shampoo 20 ml is applied to hair, left for 20-30 minutes. The mixture is removed.

It is preferably to be used when dyeing in warm shades.

However, only a single application on previously dyed hair is possible.

If the desired background has been achieved, i.e. all hair shaft is od identical quality and lightness (TDL), then pH is lowered, for example, with a postcolor mask, acidic shampoos, acids, and dyeing is started.

3.8.7 Hair Dyeing with a Composition with Water and Amino Acids

The dyeing water diffusion comprises: any desired dye+water+amino acids, in the ratio of 1:10, where there is 1 part of dye, 10 parts of water+5 parts of liquid amino acids. The composition is applied to pre-washed hair. The recovery procedure is performed with a mask (described above). The exposure time makes from 10 to 60 minutes. Then, an oxidizer is applied for 10-15 minutes, and the hair is washed. The recovery procedure with a mask is repeated, and, if there was not enough neutralization, the neutralization procedure with water is also repeated. Further on, dyeing is started with various diffusions, including dyeing, in the range of lowered pH. The components for hair recovery (amino acids, oil, glycerin, etc.) are added to the dyeing composition.

Such a composition facilitates not only hair dyeing, but also cortex filling and saturating with a pigment of a smaller fraction. The molecules penetrate deeper and saturate keratin, thereby restoring the hair by layers (with masks and active additives to dyeing). In addition, dyeing with water reduces the pigment oxidation time. Hair is saturated with pigment, and only then the pigment appears (the molecule becomes larger and color appears).

Further on, when the hair shaft has become smooth, hair recovery is made.

3.8.8. Comparison of THD Method and Classical Dyeing

The difference between the translucent hair dyeing method (THD method) from widely used dyeing methods at hairdressers' and salons (hereinafter referred to as "the classical method") is that the above-mentioned components of the claimed method help to guide the lightening and dyeing processes in the direction relevant for the hairdresser, to influence the process, to stop or to skip unnecessary steps, and to add the necessary substances to improve the hair condition.

Let's consider the simplest example of the difference between the classical dyeing method and the claimed THD method. First of all, it concerns the dyeing component proportions.

Example 3.8.8.1. Classical Dyeing

The dyeing composition comprises: dye+oxide in a ratio of 1:1 or 1:1.5 or very rarely 1:2, these proportions are indicated by the brand of the dye. These proportions are recommended for dyes of all TDLs (1; 2; 3; 4; 5; 6; 7; 8; 9; 10) in addition to TDL 11, 12 and 14 (special discoloration rows, their proportions are from 1:2 to 1:3).

The dyeing composition is applied to hair with an exposure from 15 to 65 minutes, depending on the brand and the depth level of the dye tone. After expiration of the exposure time after dyeing, the composition is washed off with shampoo, and a regenerating mask is applied.

For example, a dyeing composition is applied comprising: dye TDL 7.1+3% oxidizer (in the ratio of 1:1.5) with an exposure of 30 minutes. Then, Wash off with shampoo and a regenerating mask is applied.

Example 3.8.8.2. Translucent Hair Dyeing

Dyeing diffusion comprises: dye TDL 7.1+1.5% oxidizer (low concentration oxidizer 1%, 1.5%, 2% in priority, if you do not need to lighten or loosen hair), in proportions: dye: oxide (in a ratio of 1:6)+active agents 30-40% of the total weight of the composition+mask 5-10%+shampoo 10-20% of the total weight, applied to the hair twice with an exposure of 20 minutes. After expiration of the last exposure period after dyeing, the dyeing diffusion is washed off with shampoo and a regenerating mask is applied. If THD method is repeated, then the previous layer is simply washed off with water between the layers. When the process is over, the hair is washed with shampoo, and a recovery mask is applied.

The proportions may vary depending on hair structure and the desired color.

It is possible to use dyeing diffusion only in a mixture of a dye with an oxidizer: TDL 7.1+1.5% oxide dye (low concentration oxidizers are in priority 1%, 1.5%, 2%), if you do not need to lighten or loosen the hair), the exposure time is 7-20 minutes.

Example 3.8.8.3. Translucent Hair Dyeing into a Natural Tone TDL 7

Dyeing diffusion comprises: dye TDL 7.0+dye TDL 7.1+oxidizer 1% (in the proportion of 1 part of dye: 3 parts of oxidizer)+mask 20 g. The diffusion is applied 1 or 2 times (depending on the amount of the mixture and the desired result). The mechanical impact on hair is also provided. The dyeing composition is applied to wet (closer to wet) hair; the exposure time is 7-15 minutes. After the first application, simply wash off the dye with water and apply a second layer of the dyeing composition for 7-15 minutes. The diffusion is washed off. Hair recovery is executed, then washed off with shampoo. Hair recovery and hair care are repeated and a mask is applied.

Example 3.8.8.4. Translucent Hair Dyeing into a Natural Tone TDL 10

Dyeing diffusion comprises: dye TDL 1.0+dye TDL 8+oxidizer 1% (in the proportion of 1 part of dye: 30 parts of oxidizer)+shampoo 5 parts. The diffusion is applied to wet hair after recovery and on an unwashed mask. The mechanical impact on hair provided, i.e. the diffusion is rubbed with hands; left for 7-20 minutes. The diffusion is washed off with water and applied again by a thin layer. The procedure is repeated until the desired result is achieved—dyeing in TDL 10 blonde. After that, hair recovery and hair care are made: mask, shampoo, mask.

THD method takes into account the condition of customers' hair and coloristic rules.

Example 3.8.8.5. A Customer with Black Cosmetic Color TDL 2.0, Hair Length 50 cm; Natural Roots TDL 6.1 at the Length of 6 cm. Desired: TDL 7.1 Light Brown-Cool, Transparent Color (a Slight Tint of Pink, not Green); Very Natural Look, Color not Dense Step 1. Cosmetic Pigment Removal Remove cosmetic pigment by acid diffusion. The total working time is 2 hours. The tone was raised (TDL 2 to TDL 5). The hair shaft is unsmooth. As a rule, the structure of hair ends is denser, and the color is the darkest, because there is the main pigment accumulation (ends TDL 5.0, then TDL 5.5, TDL 6.0 and natural base TDL 6).

Step 2.

Discoloration diffusion comprises: discoloration powder+1.5% oxidizer (proportions 1:10 parts of the oxidizer)+amino acids+thickener+oils; there may be various active agents. The goal is to improve the mixture stability and to compensate for such a strong dilution with the oxidizer. The more is the oxidizer amount, the more is active oxygen and lower pH.

Discoloration diffusion is applied to wet hair, avoiding contact with the skin. The exposure time is 30 minutes. Rinse thoroughly with water. Apply repeatedly. The amount of oxidizer can be the same (1:10, or it can be diluted more). The diffusion is applied until the level higher than the desired one is reached, i.e. TDL 8, provided that hair quality enables you to work with such proportions.

Step 3.

As the natural roots have TDL 6, and the desire to have a lighter color, i.e. TDL 7, is applied to the hair roots and scalp with a ready-made lightening product for the time interval specified by the manufacturer and in dilution indicated on the package.

If there is no contact with the skin and you need to raise TDL by just one tone, lighten it with lightening. Discoloration diffusion with active agents is applied in the ratio of components: lightening powder 1 part+oxidizer 3%, 10 parts+thickener from 10 to 40 ml+liquid amino acids 10 to 60 ml+ silicone oil (dimethicone), 5-15 ml+argan oil 5-15 ml. The exposure time is visual, up to 40 minutes.

Instead of the above diffusion, a lightening diffusion for natural hair can be applied comprising: special blonde+oxidizer+shampoo, on natural hair (undyed roots) without getting on the scalp. The composition exposure time from 7 to 30 minutes, depending on how the natural base of the customer rises.

As a result, TDL 8 tone was achieved, the hair shaft is uniform, smooth by tone level.

The hair shaft can be different by quality. Where there was a cosmetic base, after lightening, hair quality will be many times worse. It is necessary to restore the damaged areas and bring to a uniform hair shaft quality. Then proceed to Step 4.

The hair shaft can be different by color, i.e. where there was a cosmetic base, there will be a dense red color, and where there is a natural base, there will not be such an amount of red, it will rather be orange-red or red-orange, someone has orange, someone on this TDL red, but not in the same amount as in the cosmetic base, depending on the genotype. Then proceed to Step 5.

Step 4: Hair Recovery and pH Reduction.

Apply the mixture of active agents+ steam. Masks are applied, necessarily with mechanical impact and care layering on sites where there are more damaged areas, until they achieve the same quality on the entire hair shaft. Slightly wash off the previous components with water. Apply care for 15-30 minutes and stand under heat. The total recovery time is 60-120 minutes.

Step 5: Color Alignment. Color Background.

On areas with red color, the opposite color is applied—green, using neutralizing diluted diffusion. Example: green "Russian" mixtone 10 cm+oxide 250 ml+shampoo 30 ml. Apply this composition to the areas where the hair had been previously dyed with cosmetic pigment. The exposure time is from 7 to 20 minutes. Neutral gray should be seen. If it does not occur, wash off the composition with water and apply the same composition again. The exposure time is from 7 to 20 minutes. Repeat until a neutral color (gray) appears.

Step 6: Adding Red Mixtone to Natural Hair Areas

Warm red or magenta mixtone 5 cm+oxidizer 150 ml+shampoo 20 ml. Apply to natural hair, avoiding contact with the skin. The exposure time is from 7 to 20 minutes. Wash off with water.

Step 7:

Make a hair mask with a mechanical impact, leave for 15-30 minutes under polyethylene.

Step 8: Dyeing in the Desired Color with Dyeing Diffusion

The dyeing diffusion comprises: dye TDL 7.1, 30 g+dye TDL 1.0, 3 cm+blue mixtone 6 cm+oxide 1.5% in the ratio 1 part of dye: 2 parts of oxide+oils 15 ml+amino acids 20 ml+ silicone compositions 15 ml+foam with panthenol 30 ml+acids 5 ml.

Apply to the hair for 15-30 minutes, depending on the desired color density as a result. Wash off with shampoo (shampoo helps to understand how much color will be washed after dyeing, as hair was dyed after lightening). Rinse with water, apply a mask for 10 minutes, rinse with water.

Step 9: Refinement of Irregularities.

It is possible that color irregularities will be visible on hair shaft, as hair porosity has not been fully leveled yet, and powder residuals may lighten a part of pigment.

Refinement means color alignment; its density depends on how the main dyeing was laid in Step 8. If it is very transparent, and a dense color is needed, the refinement will be quite dense in dilution, and vice versa. There may be different color density on some parts of the hair shaft. Let's assume that an average refinement density is needed.

In Example 4.4., the roots with a natural hair color have become colder by color, and they need adding orange-red.

Composition for alignment is a pre-pigmenting diffusion comprising: dye TDL 6.34 (yellow-orange-red), 8 cm+orange mixtone, 3 cm+magenta, 2 cm+oxide 1.5% (ratio—dye 1 part: oxide 10 parts)+shampoo 30 ml. The exposure time is visual, preferably 7-20 minutes, for color fastness.

The hair ends, on the contrary, need adding more green, because their color is warmer than the rest, due to the pigment that was laid in the hair.

Neutralizing diffusion is used comprising: dye TDL 6.2 (green) 15 cm+green mixtone 5 cm+blue mixtone (to make the color colder) 3 cm (ratio—dye 1 part: oxide 10 parts)+shampoo 50 ml. It is advisable to make the dye more transparent so that the color does not quickly turn into the opposite one (for example, green) and would not have to be washed off, which will not give a stable result. The composition is applied to the necessary areas, the color is visually monitored. The exposure time is 7-20 minutes. If there is not enough color, the same composition is added again or a new composition is made, denser in color. The previous one is washed off with water.

Step 10: Recovery Mask

Apply a recovery mask for 20-30 minutes under heat and steam. Mechanically affect and comb.

Step 11: Final Translucent Dyeing

Final translucent dyeing is performed to add a desired second shade on top of the main color.

The basis of the dyeing composition is diluted diffusion or diffusion with direct-effect pigment, most often a mixtone of a purer color. It is possible to add direct-effect pigments (they lie in the upper layers of the hair and provide an optical shift).

Diffusion with direct-effect pigment comprises: dye, magenta mixtone 3 cm+direct-effect pigment, magenta 6 cm+direct-effect pigment, blue 3 cm+1% oxidizer (ratio— dye 1 part: oxide 25 parts)+ silicone (dimethicone, or the composition of dimethicone+cyclomethicone)+shampoo 40-50 ml (depends on hair thickness and the pigment amount to be diluted). They are balanced by diluting the dye with an oxidizer and shampoo. It is possible to make several finish translucent hair coatings depending on the desired color. For example, if you want to make the color more sprayed, they do gray finish coating. Wash off with water and shampoo.

Hair recovery with active agents is done for Example 4.1.5.

The recovery is done with active agents, such as, for example, emulsifiers, masks, various oils (jojoba, linseed), amino acids, liquid and dry solutions, glycerin, acids, and thickeners.

Layer-by-layer dyeing with pre-neutralization, pre-pigmentation, substrates and layer-by-layer applications of various diffusions facilitate dyeing your hair with an accurate color-to-color fitting. Besides, the customer gets dyeing durability from 1 to 6 months, depending on hair quality. The color will no longer be leached to red, it will become lighter by a tone and will become TDL 7.5, and 31 in color direction—golden ashy.

Diffusions with direct-effect pigments (Table 1, Item 12) are used in the end of dyeing or, if a transparent blonde is created, can be used as an independent dyeing.

Diluted diffusion (Table 1, Item 11) is used when it is necessary to introduce the purest possible color and reduce the alkalinity of the dye as much as possible.

Artistic diffusion (Table 1, Item 10) is used while dyeing when it is difficult to calculate the amount of mixtone needed to be added to neutralize or pre-pigment and not to darken hair shafts. Then mixtones with an oxidizer are diluted in separate containers, one for each color. Separately, the dye is diluted. The dye is applied onto the hair shaft, and then pre-diluted mixtones are gradually applied as well. Thereby controlling the process of color movement and avoiding possible darkening. It can be either an independent type of dyeing, or a color refinement.

Max-mix diffusion (neutralization+pre-pigmentation+lightening+dyeing) (Table 1, Item 9) is used for vitreous hair type, which is also found in natural hair, and not only in gray hair.

Interchangeable diffusions are provided. For example, you can do a pigmenting diffusion and then the dyeing one. But you can do artistic diffusion, i.e. add mixtones of any color to the dye, including orange and add warm colors, which will be pre-pigmentating diffusion. For example, you can do lightening diffusion, then pre-pigmentating diffusion, afterwords dyeing into natural color diffusion and possibly a neutralizing one will also be required. But you can take max-mix diffusion, wherein all these components already exist in one mixture.

Example 3.8.8.6. The Use of Artistic Diffusion

Baseline hair roots are natural base TDL 7. Length is cosmetic base TDL 8.34 (8-light brown, 3—gold, 4—orange). Desire: to color the length and roots in TDL 7.1 (1—ash color).

Step 1. Apply the composition of dye TDL 7.1+1.5%+shampoo to the hair for 10-15 minutes, avoiding contact with the scalp.

Next, Mixture 1 is diluted in a container: mixtones of colors yellow, orange and warm red, warm green, emerald are diluted in the ratio of 1:20 with an oxidizer. The mixture is left to stay.

Mixture 2 is diluted in a separate container: mixtones of colors green-blue, blue-green, blue, blue-purple, magenta, purple in the ratio of 1:40 with an oxidizer. The mixture is left to stay.

Step 2. Wash off 20-30% of the composition applied in Step 1 (TDL 7.1+1.5%+shampoo). Mixtone blue from Mixture 2 is applied above the composition with TDL 7.1 dye, left for a while and compacted with mixtone blue if necessary. It will turn out to be TDL 7.1, and the more blue you add, the colder the color 7.11 will be.

If too much blue is put in the dyeing composition, 20% of the mixture is washed off and a mixtone is applied from the first container. They are left until the desired color is obtained, from 7 to 30 minutes. The mixture is removed with water, then shampoo is applied, then a hair mask, after which it is washed off with water.

Example 3.8.8.7. The Use of Max-Mix Diffusion

Baseline hair: natural base TDL 8, vitreous hair, hair length dyed TDL 5.0.

Dye to TDL 5.0 twice. The first time when applying TDL 5.0 to natural hair, 6.5 TDL is obtained, i.e. lighter than necessary. Apply TDL 5.0 a second time. As a result, the desired TDL 5.0 will be obtained.

Example 3.8.8.8. The Use of Max-Mix Diffusion with Composition

The composition to be used: dye 10.0 TDL, 5 g (for loosening vitreous hair)+dye TDL 6.5, 5 g (the dye with red: 6.5—dark brown, 5—red, because there is no red color in TDL 8, which should be in TDL 5) for pre-pigmentation of natural hair at the roots+blue mixtone 1.5 cm (as red could be shifted, together they will give a natural color)+desired tone 5.0 TDL (40 g)+TDL 1.0 (3-4 cm) (thus, not only loosening, but also darkening occurs)+oxidizer 80 ml+shampoo 30 ml. The exposure time is 30 to 50 minutes. Then remove the composition.

Diffusion, which includes several diffusions at once, enables you to develop an individual composition for a specific customer and to replace several stages of applying individual diffusions with a single, complex diffusion.

For comparison, consider the classical dyeing in the example below.

Example 3.8.8.9

A customer with a black cosmetic color (TDL 2.0) along the length of 50 cm and natural roots of TDL 6.1, length 6 cm. Desire: TDL 7.1 light brown as a cool, transparent color (a slight tint of pink, not green), so that it would look very natural, not a dense color.

Step 1: Cosmetic Pigment Removal.

Apply a commercial lightening powder, more often on unwashed hair, although the option of pre-washing the hair is possible.

The classical composition is 1 part of powder: 3 parts of the oxidizer. Possible violations of mixing proportions 1:2 or 1:1 are intended to make more of the discoloration mixture, and, as a result, to enhance the lightening effect, which leads to damage to the hair structure. The exposure time, as indicated on the powder packaging, more often from 20 to 60 minutes. But this time is also often violated in beauty salons, to achieve a better lightening result, expose for 180 minutes to greatly lighten and raise the tone to 8 tone levels. It leads to hair damage up to its complete destruction. Often the hairdressers raises the tone to the desired limit, in this case 7TDL, not taking into account the color failure during neutralization. Hairdressers resort to heating the mixture (it reduces the time spent by the hairdresser, but negatively affects the hair).

If everything is done correctly and according to the guidelines, you will have to apply the finished compositions 5-6 times, it means apply, leave, rinse with shampoo and water. Dry the hair. Apply a new composition, leave for 60 minutes, rinse, dry and in this manner, 6 times, possibly more, if the result is not achieved in terms of lightness. More often it will not be achieved, as hair quality will not enable to lighten for so long.

Let's assume that the hairdresser has reached the desired tone level, then, hair quality will be much worse than using the claimed method.

Step 2. Dyeing into the Desired Color.

Dyeing composition: dye TDL 7.1 or 6.1, 60 g (one can take a darker dye so that it would accurately dye over all the irregularities)+oxide 1.5% to 9%-12%), more often 3% are chosen, and the ratios specified by the manufacturer, for example, 1:1. The exposure time specified by the manufacturer makes most often 20-30 minutes.

The result will be much warmer, and the durability of such dyeing is 5 to 14 days, a maximum of a month, depending on hair TDL that was achieved after the powder and hair quality.

The main disadvantages of classical dyeing in this case are a large loss of hair quality and a large amount of brown in the dye, the absence of a pure opposite color needed for neutralization (green mixtone). Hairdressers do not use these colors, because they can darken hair and they cannot calculate the amount of mixtones required for hair of a particular customer (because depending on the genetic factor, the amount may be different for different people, 1 cm to 30 cm, for example). The classical method does not facilitate visual control of the process, and the result is visible only after a full exposure time.

As a result, the hair is destroyed to remove the dense brown cosmetic pigment, and again dyed with a dye that already comprises about 75% brown, only lighter.

Such dyeing will wash out in a fairly dense orange color TDL 7.44, where 4 is orange (but it is visually orange, in fact, it is a blurry red, because TDL 2.0 corresponds to red).

When the customer returns after 2-3 weeks, he is dyed again with the chosen dye and, at the best, 1 cm of blue mixtone will be added, without counting an oxidizer for it (as a result, red neutralization is not done)+a new portion of brown+blue will also darken the color. The desired result was short-lived, and it will always be washed into warm, and with each visiting the salon, a new dyeing will darken customer's hair.

THD method enables you to accurately get into the desired result, and prevent color washout. Therefore, the customer will dye his hair much less often.

Due to the layers of diluted components, it is possible to restore the hair structure, and to get perfectly into color. The first procedure using THD method with recovery and alignment of the hair shaft can take a long time. In the future, the restored and uniform-dyed hair will be dyed much faster.

3.9. Implementation of Translucent Hair Dyeing Method According to Option 3—Dyeing Gray Hair Gray hair is devoid of natural hair color. A special pigment, melanin, is responsible for hair color. With age, it begins to be produced worse, as a result of which gray hair appears. The hair becomes empty, stiff, does not respond well to chemical influences, and loses its shine.

The result of the claimed method is rejuvenation of gray hair, when a transparent natural shade is obtained without excessive density, but with 100% overlap of gray hair. It is achieved by loosening the hair structure and maintaining the TDL balance. The method of translucent hair dyeing enables you to find a balance in the amount of lightening background and gives a more transparent result.

The difficulty of dyeing gray hair lies in the fact that gray hair is vitreous. It is difficult to penetrate into it with a dye. Therefore, it should be loosened with ammonia beforehand. Classical dyeing provides for the use of a dye with enhanced ammonia for this purpose.

The customer may have a small percentage of gray hair, but the customer wants to get rid of gray hair. If you take a specialized dye for gray hair (from 0 to 30%), after dyeing a browner and denser color will be obtained in the future, which is not always needed.

The claimed THD method provides for this purpose a step-by-step procedure, as a result of which the dyed gray hair looks more natural and transparent.

THD method according to Option 3 is intended for dyeing gray hair. It may include the following steps.

Cleansing hair from impurities and metals or from direct-effect pigments;
Loosening of gray hair;
Removal of the composition from hair with water;
Making a substrate for gray hair (neutralization+pre-pigmentation+addition of a natural brown tone);
Removal of the composition: shampoo, water, and mask.
Dyeing to the desired tone;
Removal of the composition with shampoo and water;
Color refinement;
Removal of the composition with shampoo and water;
Restoration of hair with active agents or Cleansing hair from impurities and metals or from direct-effect pigments;
Loosening+pre-pigmentation of gray hair;
Removal of the composition from the hair with water;
Making a substrate for gray hair (neutralization+pre-pigmentation+addition of a natural brown tone;
Removal of the composition: shampoo, water and mask;
Hair recovery;
Dyeing to the desired tone;
Removal of the composition with shampoo and water;
Color refinement;
Removal of the composition with shampoo and water;
Restoration of hair with active agents, or Cleansing hair from impurities and metals or from direct-effect pigments;
Loosening+substrate for gray hair (neutralization+pre-pigmentation+natural brown) of gray and natural hair (gray hair up to 60%);
Removal of the composition from the hair with water;
Hair recovery;
Hair dyeing into the desired tone;
Color refinement;
Removal of the composition: shampoo, water, mask;
Hair recovery with active agents.

Cleansing Gray Hair from Dirt by Shampooing

Shampoo is applied to hair, close to the scalp; it is left for 3-5 minutes.

Removal of direct-effect pigments or plant dyes is done with clay diffusion. Alcohol is applied to dry hair. The exposure time until complete evaporation is 10 minutes on average. Then diluted clay+hot water+glycerin is applied. It is left for 20-40 minutes under heat and polyethylene. It is washed with pH 5.5 shampoo once or twice. If necessary, the procedure is repeated.

Loosening Gray Hair

Since it is difficult to penetrate into vitreous gray hair with a dye, the hair needs to be loosened. Loosening is done with ammonia. To do it, either lightening diffusion or a mixture of ammonia with an oxidizer is used.

The Use of Lightening Diffusion for Gray Hair

The composition of lightening diffusions is described in detail in Section "Diffusion compositions used in the claimed method", Part 2.

The composition of lightening diffusion includes a dye (special blonds and 10 TDL rows)+oxidizer+shampoo.

The lightening strength is 1-3 tones up. It loosens hair well. It is advisable not to apply to the scalp, because the shampoo in the mixture helps the dye components penetrate deeper into the skin. It enables not just to lighten, but to loosen the hair for deeper penetration of the subsequent dyeing composition.

Lightening diffusion according to the claimed invention is used as a preparation for dyeing, for the uniform coincidence of TDL of their own hair with TDL of dyed hair, and a smooth transition from natural color to the dyed one. Diffusion enables you to loosen and lighten better after 10-30 minutes, as a preliminary stage, to understand what the lightening background and its density on the hair of a particular type of hair.

Application of Lightening Diffusion Type 1

Composition: dye special blonde TDL 11, 12, 14 (00 ammonia and LT, Ltx—various designations of special blonds)+oxide 12% or 9%+shampoo.

Dilution proportions: 1 part of dye: from 1 to 30 parts of oxide: shampoo from 2 to 300 ml.

The more shampoo, the stronger is the effect, because the composition is more dispersed, penetrates deeper and loosens the hair better and lightens deeper in the cortex.

This lightening diffusion is also created for loosening gray hair.

Application of Lightening Diffusion Type 2

The lightening strength is weaker than that of Lightening Diffusion Type 1.

Composition: dye TDL 10+oxide 3%-12%+shampoo.

The dye is less alkaline and, as a result, provides less lightening effect.

Lightening Diffusion Type 2 is less aggressive Type 1. It is often necessary to raise one tone up or to loosen the gray hair, and parallel lightening is not desirable. In this case, Lightening Diffusion Type 2 is preferable.

Dilution proportions: 1 part of dye: from 1 to 30 parts of oxide: shampoo from 2 to 300 ml.

Example: dye TDL 10.0, 10 g+oxide 9%, 30-100 ml+shampoo 5-50 ml.

It is left 10 to 30 minutes. Avoid contact with the scalp. Wash off the mixture with water.

Loosening can be done with a mixture of ammonia with an oxidizer. Composition: ammonia+oxidizer, where the oxidizer is 6% to 12%.

Example. A mixture of 40 ml of oxide and 5 to 10 g of ammonia is applied to hair without contact with the scalp. The exposure time is 20-30 minutes. Washed with water, shampoo, water again. With more percentage of gray hair or, if gray hair is more vitreous, increase the amount of ammonia up to 12 g.

Simultaneous Loosening and Pre Pigmentation of Gray Hair

In addition to loosening, the method makes it possible to simultaneously perform two actions: loosening and pre-pigmentation with the following diffusions described earlier. The use of lightening and pre pigmentation diffusion (Section "Diffusion compositions used in the claimed method", Part 6.

Lightening and pre-pigmentation diffusions are used for natural and gray hair.

The lightening strength is 1-3 tones up. Loosens the hair well. It is advisable not to apply it to the scalp, because due to the shampoo, it helps the dye components penetrate deeper into the scalp.

Application of Lightening and Pre-Pigmentation Diffusion Type 1

Composition: dye+special blonde TDLs 11, 12, 14 (00 ammonia and LT, Ltx are designations of special blonds)+12% or 9% oxidizer+shampoo+warm color dye+warm-color mixtone.

Dilution proportions: 1 part of dye special blond of warm colors (warm yellow, orange, orange-red, red-orange, warm red): from 1 to 30 parts of the oxidizer: shampoo from 2 to 300 ml+dye TDL 5 to 9. 0.01 parts to 3 parts+mixtone 1 to 20 cm.

Since this diffusion should lighten and pre-pigment at the same time, a balance is needed in terms of the amount of oxidizer and shampoo;

The proportions of the oxidizer are close to those recommended by the manufacturer (mainly 1:2, where 2 are parts of the oxidizer, but there may be more);

Mixtone and dye (not a special blend), add the color itself, necessary for pre-pigmentation.

Example (see Section "Diffusion compositions used in the claimed method", Part 6). dye TDL 12.3 (30 g)+8.44 (30 g)+mixtone (3 cm)+oxidizer 110 ml+shampoo (30 ml).

Application of Lightening and Pre-Pigmentation Diffusion Type 2

The dye is less alkaline and, as a result, less lightening;

The diffusion is less aggressive than Lightening and Pre-Pigmentation Diffusion Type 1. It is often necessary to raise one tone up or loosen the gray hair, and parallel lightening is not desirable, then this composition will be preferred.

Dye 10 TDL+3%-12% oxidizer+shampoo.

Dilution proportions: 1 part of dye 10 TDL blonde warm colors (warm yellow, orange, orange-red, red-orange, warm red): from 1 to 30 parts of the oxidizer: shampoo from 2 to 300 ml+dye TDL 5 to 9. 00.01 parts to 3 parts+mixtone 1 to 20 cm.

Example: 10.3 (30 g)+8.44 (30 g)+mixtone (3 cm)+oxidizer 70 ml+shampoo (30 ml).

Loosening+Substrate with Lightening

This procedure enables you to bring the necessary pigment deep enough into hair cortex, while not seeing a smooth color, but the necessary colors are brought deep into the cortex. Subsequent dyeing is performed in the upper layers of the hair, and the dye will be formed without darkening in the same layer of the hair.

It is performed with TDL dyes of 10 rows and special blonds TDL rows 11, 12, 14 (00 ammonia and LT, Ltx are designations of special blonds)+a warm-dyed mixtone (orange, red, yellow-orange.)+mixtone to neutralize lightening of natural hair (green, blue, blue-green, blue-purple) and provided that this neutralization is necessary (and that in addition to gray hair, there is hair with pigment.)+oxidizer 3% to 12%+shampoo.

The exposure time is 15 to 50 minutes.

The amount of warm and cold colors is selected based on Table 1, those based on the percentage of gray hair.

This combined type of neutralization, pre-pigmentation and loosening solves several problems at once in the dyeing of gray hair and prepares gray hair for the very process of dyeing, i.e. the dye will lie down as intended by the manufacturer.

Example: TDL dye 10.1 30 cm+orange-red mixtone 5 cm+blue-green 3 cm+oxidizer 12%+shampoo 20 ml without contact with the scalp, exposure time from 15 to 50 minutes. Removing the Composition with Water.

If there was contact with the skin, which is not desirable, then the removal of the composition is done with shampoo, water is washed abundantly. If there was no contact with the skin, then rinse with shampoo, then with water. The mask is not applied.

The Substrate for Gray Hair

Neutralization+pre-pigmentation+adding a natural brown tone. This type of substrate is used to correct irregularities before dyeing gray hair, because gray hair is one of the most difficult types of hair. The substrate should be lighter than the desired TDL by at least 1-2 tones up.

The substrate is closely interrelated with the dyeing process itself. If a lot of neutralizing and pre-pigmenting colors are put into the substrate, then these colors will either not be at all in the main dyeing, or will be several times less than in the substrate. Visually, after the color substrate, you can already see a fairly uniform base in color. The task of the substrate is to create a "hair shaft" for further hair dyeing. It enables you to bring various lightening backgrounds, which are closely related to the genotype of the person who owns these hairs, into the right color with 100% hit, and directly see the process of color formation and stop it at the right moment.

This type of substrate is formed from the desired dye+ neutralizing mixtone+pre-pigmenting mixtone+oxidizer 1% to 12% (from 5 to 300 ml)+shampoo from 5 to 150 ml.

The number of mixtones will vary from 0.5 cm to 15 cm. If we visually see a highly saturated lightening background, then the amount of mixtone having the color of neutralization tends to increase, i.e. from 0.5 cm to 15 cm. And vice versa, if gray hair after loosening is poorly prepared (white or cold pink color remained), then the amount of mixtone with a warm color of pigmentation will prevail over the amount of neutralization: cold color from 0.5 cm to 15 cm and warm color from 0.5 cm to 15 cm, you need to find a balance based on the hair.

Approximate proportions:

15 cm neutralization: 15 cm pre-pigmentation 15 cm of neutralization: 5 cm of pigmentation 15 cm of pre-pigmentation: 8 cm of neutralization and other options.

To correctly select the quantitative composition of the substrate, you can use Table 2.

According to this table, you can not only make a neutralizing and pre-pigmenting substrate, but also use it to form a complete composition of the dyeing composition. Also, the ratios indicated in the table can be used for both mixtone and dye.

The most common diffuse type of gray hair occurs when gray hair (without pigment) grows next to natural hair with pigment. Gray hair needs loosening and pre-pigmentation. Natural hair, on the contrary, when loosened, will immediately show a lightening background: red or orange, or yellow, or a mixture of these colors.

Thus, the colorist is faced with the task of dyeing over gray hair smoothly, making them lightening background, which they are deprived of. Only then the dye will show the desired color, and in addition, to neutralize the natural hair. The composition recipe should contain both warm and cold colors in different proportions depending on the percentage of gray hair.

Recipes of preparations for gray hair

TABLE 2

| Warm | Neutral | Cold | Colors |
|---|---|---|---|
| Recipe for gray hair <40% | | | |
| warm > cold 2.5:1 | warm > cold 1.5:1 | cold > warm 2:1 | 10 Yellow-orange 9 Blue-purple 8 7 Orange-red 6 Blue-green 5 |
| Recipe for gray hair 40-60% Warm *2+\0 or *2+\0+\7 | | | |
| warm > cold 5:1 +\0 warm > cold 5:1 +\0+\7 | warm > cold 3:1 +\0 warm > cold 3:1.5 +\0+\7 | cold > warm 2:2 +\0 cold > warm 2:1 +\0 | 4 Red 3 Green 2 1 |
| For gray hair 60-100% | | | |
| Pre-pigmentation Re-pigmentation Dyeing stage by stage | | | |

The recipe for the dyeing composition depends on the degree of gray hair, which can be of the following types:

Gray hair >40%;

Gray hair 40-60%;

Gray hair 60-100%.

Based on the percentage of gray hair, the recipe for the dyeing composition will change.

Gray hair >40%.

The amount of gray hair is less than half of the total amount of hair, and up to 10%. The lower the percentage of gray hair, the more the composition recipe for dyeing should contain neutralization of natural hair and less pre-pigmentation.

The table shows the parts of warm (those pre-pigmenting colors) and cold (neutralizing colors) to create different end results, you want to create a neutral color in the end, either warm or cold.

Gray hair 40-60%

Comprising for dyeing, a warm color is added twice as much, a significant amount of a natural series of TDL 7.0-1.0 is added, since the amount of gray hair prevails.

With gray hair, which is closer to 60%, in addition to pre-pigmentation and the addition of a natural row, another brown-red color is added. Table 1 also shows the parts of warm and cold colors. The parts in Table 1 refer to both mixtones and dyes.

In addition, alkalinity is added to the composition with a dye of 12 or 10 rows.

Gray hair 60-100%

When dyeing gray hair 60% to 100%, it is desirable to make loosening and pre-pigmentation;

Hair recovery;

Dyeing with water;

and then the compositions discussed above, but without neutralization, since there is a minimum amount of natural hair.

Example of dyeing gray hair up to 40% Creating a cool final color:
1. Loosening of gray hair by lightening diffusion+neutralizing-pre-pigmenting substrate.
2. Removing the mixture of water, shampoo, mask
3. Substrate without loosening.
4. Hair recovery.
5. Dyeing by diffusion of dyeing.
6. Removal of the mixture: water, shampoo, mask.
7. Refinement by diluted diffusion.
8. Recovery.

The Composition for Dyeing Gray Hair is Up to 40%

Loosening gray hair by lightening diffusion+neutralizing-pigmenting substrate. Composition TDL dye 12.3 (15 cm)+6 cm orange-red mixtone+12 cm blue-green mixtone+oxide 12%+shampoo 15 ml. Applying the composition without skin contact, only on the hair, leaving 0.5 cm to the scalp.

Substrate without Loosening

Composition. The desired dye, for example TDL 7.1+ based on the result seen, a mixtone correction is made. For example, if neutralization was not enough, then a blue-green mixtone 6 cm+orange-red 2 cm+an oxidizer 2%+shampoo is added to the TDL 7.1 dye. Applying the composition occurs without contact with the scalp.

Application of Dyeing Diffusion

Dyeing diffusion, which is the desired dye, for example TDL 7.1+pre-pigmentation+neutralization.

Composition: dye TDL 7.1, 30 g+blue mixtone, 10 cm+orange mixtone 5 cm+oxidizer 3%, 50 ml.

Refinement of the color based on what you saw. For example, dye TDL 7.1, 2 cm+oxidizer 1%, 40 ml+shampoo.

Example of Dyeing Gray Hair 40%-60%
1. Loosening of gray hair with lightening diffusion or lightening+pre-pigmenting.
2. Removal of the mixture with water, shampoo, and a mask.
3. Hair recovery.
4. Dyeing with dyeing diffusion.
5. Removal of the mixture with water, shampoo, and a mask.
6. Refinement with diluted diffusion.
7. Hair recovery.

The Composition for Dyeing Gray Hair 40%-60%.

The loosening of gray hair is done with lightening diffusion or lightening+pre-pigmenting diffusion.

The composition of lightening diffusion: TDL dye 12.3, 15 cm+oxide 12%+shampoo 15 ml.

The composition of the diffusion is lightening+pre-pigmenting. dye TDL 12.3, 15 cm+orange-red mixtone, 6 cm+oxide 12%+shampoo 15 ml. Applying the composition without skin contact, only on the hair, leaving 0.5 cm to the scalp. Exposure time 30 min.

Dyeing with Dyeing Diffusion.

Composition: the desired dye, for example TDL 7.0, 30 g+blue mixtone 5 cm+orange mixtone 15 cm+dye TDL 1.0, 4 cm+oxidizer 3%, 60 ml.

Refinement with Diluted Diffusion

Depending on the result you see, add the necessary mixtone and according to the proportions specified in the diffusions.

Example: orange mixtone, 4 cm+direct-effect pigment pink, 5 cm+oxidizer 1.5%, 60 ml+shampoo 20 ml. Exposure time visually, at least 5-7 minutes, for durability 7 to 15 minutes.

After applying the substrate and refining with diluted diffusion, hair recovery is made with active products.

Example of dyeing with gray hair up to 100%

Creating a neutral final color (i.e. neither warm nor cold tone, for example, TDL 7.3).
1. Loosening of gray hair by lightening (or lightening+pre-pigmenting) diffusion
2. Removal of the mixture with water, shampoo, and a mask.
3. Hair recovery.
4. Dyeing with water.
5. Removal of the mixture with water, shampoo, and a mask.
6. Dyeing with dyeing diffusion
7. Removal of the mixture with water, shampoo, and a mask.
8. Refinement with diluted diffusion.
9. Hair recovery.

The Composition for Dyeing Gray Hair Up to 100%

Loosening+Pre Pigmentation

The composition of the diffusion is lightening+pre-pigmenting. TDL dye 12.3, 15 cm+orange-red mixtone, 6 cm+oxide 12%+shampoo 15 ml. Applying the composition without skin contact, only on the hair, leaving 0.5 cm to the scalp. Exposure time 30 min.

Dyeing with Water

A dyeing diffusion with water is used, described in Example 4.3. in the section "Diffusions". Composition: dye+water+liquid amino acids The ratio of the dye to water is 1:1 to 1:20, where 20 are parts of water+amino acids 1 part to 5 parts.

The exposure time is 10 to 40 minutes under heat or use a vaporizer.

Then, without washing, the oxidizer is applied for 10-15 minutes 1% to 6%, depending on the depth of penetration.

Example: the desired tone TDL 7.13 (where TDL 7 is light brown, 1 is ash color, 3 is gold. Total-neutral color) (20 cm)+water 80 ml+20 ml of amino acid.

The exposure time is 30 minutes under heat. Then an oxidizer of 3% is applied for 15 minutes. The mixture is removed with water.

This diffusion is one of the most preferred compositions in dyeing according to the claimed method. It enables durable hair dyeing with minimal damage. It is excellent for weakened and damaged hair and refers to safe dyeing.

Dyeing with Dyeing Diffusion

The desired dye, for example, is TDL 7.13.

Composition. TDL dye 7.13, 15 cm+orange mixtone, 15 cm+dye TDL 1.0, 2 cm+oxidizer 1.5%, 60 ml. The exposure time is 20 minutes.

Refinement with Diluted Diffusion

Depending on the result you see, add the necessary mixtone or dye.

Example: pink mixtone, 2 cm+dye TDL 7.13, 2 cm+oxidizer 1.5%, 30 ml+shampoo 20 ml. Exposure time visually, at least 5-7 minutes, for durability 7 to 15 minutes.

Addition of a natural series of TDL 1.0 occurs due to a large amount of pigment in black, which contributes to a better dyeing of gray hair and darkens the color well, if necessary, after loosening.

Addition of a warm brown color is due to coloristics. Gray hair lacks, as a rule, a natural red or brown-red color. Adding it to the dye mixture will make any color more natural.

Removal of the Composition

The hair is washed abundantly with water; washed with shampoo for 5 minutes; a "post color" mask is applied for 15 minutes, with mechanical impact, heat is applied. Then they are washed with water.

Color Refinement

This stage enables you to refine the errors after dyeing, which cannot be solved only with the dye.

At this stage, the thinnest layer of dye is applied, i.e. the final lamination. It can be performed with the following diffusions: artistic diffusion (Table 1, Item 9), diluted diffusion (Table 1, Item 11), diffusion with direct-effect pigments (Table 1, Item 12). A detailed description of these diffusions is given in the relevant parts of Section "Diffusion compositions used in the claimed method".

The artistic diffusion is used for hair dyeing of artistic dyeing type. Each mixtone is diluted in a separate container. Mixtones are diluted in the ratio mixtone: oxidizer from 1:10 to 1:40, preferably 1:20. The oxidizer in this case is low, 1% to 3%.

The dyeing artistic diffusion is applied to hair, for example, dye TDL 7.1+1.5% oxidizer in the ratio of 1:2; left for 10 minutes; massage mechanically; 20% of the composition is washed off with water, and the desired color is applied from a container with a certain mixtone. In this example blue mixtone+oxidizer in the ratio of 1:20. The exposure time is visual, but not less than 7 minutes (dilution enables to elevate the ratio to 1:40). When the desired color is reached, it is washed off with water and the process is completed with a mask with an acidic pH ("post color") and washed off with water.

If the color does not suit the customer, you can simply wash off 20% of the composition with water and apply another color, for example, pink. As a result, TDL 7.112 is obtained, where 7 is TDL, the number 1 after the dot is a cold color, ash-blue and 2 is pink. The mixtone has strengthened the dye 7.1 to 7.11.

You can create any colors, change them within 2-3 minutes and control the whole process of obtaining color.

The use of diluted diffusion for dyeing gray hair is stipulated in Section "Diffusion compositions used in the claimed method", see examples below.

Example. The diluted diffusion comprises the dye amount in a small amount, from 1 cm to 20 cm, and mixtones predominate. The amount of oxidizer is maximum 40-300 ml; shampoo—depending on hair density for distribution and as a diluent, including 2 to 200 ml.

Composition: dye from 1 cm to 20 cm, a mixtone from 1 to 100 cm, oxidizer from 40 to 300 ml; shampoo from 2 to 200 ml.

Example. The Diluted Diffusion Comprises Only Dye+Oxidizer.

Diluted diffusion can be without the addition of a shampoo.

If the dye needs to penetrate deeper, then shampoo is needed, if surface application of the dye, then shampoo is not required.

Composition: dye from 1 cm to 20 cm, the oxidizer is maximum 40-300 ml.

Example. The Diluted Diffusion Comprises Only Mixtone+Oxidizer.

In the composition of the diluted diffusion. The amount of mixtone is from 1 to 100 cm, and mixtone prevails in the composition. The amount of oxidizer is maximum 40-300 ml.

If the dye needs to be diluted to make the color lighter, or a finely dispersed consistency is needed, shampoo is added in the amount of from 2 to 200 ml.

Example of color refinement. As a result of dyeing, the tone turned out to be too cold.

The composition of the diffusion diluted for refinement: mixtone orange 5 cm+low oxidizer, preferably 1%-1.5%, 70 ml+dye TDL 7.4, 2 cm (as a carrier containing more ammonia, for durability)+shampoo 30 ml.

Application for dyeing of diffusion with direct-effect pigments (Table 1, Item 12).

The diffusion is applied to wet hair: direct-effect pigments, 50 g+oxidizer from 5 to 200 ml or direct-effect pigments (50 g)+oxidizer (5 to 200 ml)+oxidative dye (dye TDL 10.0, from 1 cm to 20 cm); exposure time 5 to 40 minutes, preferably under heat;

or diffusion is applied to wet hair: direct-effect pigments, 50 g+oxidizer from 5 to 200 ml)+shampoo, or direct-effect pigments, 50 g+oxidizer (from 5 to 200 ml)+oxidizer dye (dye TDL 10.0, from 1 cm to 20 cm)+shampoo.

Rinse with cool water, apply a mask, leave for 15 minutes under heat; rinse with water.

It is possible to re-apply diffusion, i.e. make glaze coating.

Hair Recovery

Hair recovery is performed as follows:

Gelatin (from 50 to 400 g) is dissolved with hot water, the temperature is close to boiling. Let the mixture cool for 1-2 minutes and add the active agents:

amino acids (from 5 to 100 ml);
various oils (from 5 to 150 ml);
glycerin or hyaluronic acid (from 3 to 100 ml);
various silicones (from 5 to 100 ml).

Mix them over.

Apply the components under polyethylene and heat to wet hair for 20-30 minutes.

Next, lightly rinse with water and apply a recovery mask.

You can apply a deep recovery mask over it without washing it off. Put it under polyethylene. The exposure time is another 10-40 minutes. It is advisable to periodically comb and mechanically work with your hands.

Example. Hair recovery is done as follows.

Apply a hair mask to moisturize wet hair;

It is tapped mechanically into the cortex (the movements are light and top-down or slightly vibratory);

Periodically comb with a comb;

Perform this procedure for 10-15 minutes;

Then, the hair is covered with polyethylene and placed under heat or without polyethylene under a vaporizer. Exposure time is 10-30 minutes.

Rinse with slightly cool water;

Repeat the procedure until the desired quality, density and moisture content is achieved.

It is preferable to perform hair recovery before dyeing. I is also possible to make recovery between dyeing by layers, as well as at the end of the whole process. Finally, the compositions are removed with water.

Application of Max-Mix Diffusion (Table 1, Item 10).

Besides, gray hair can be dyed with fewer stages with max-mix diffusion (10).

Max-mix diffusion is used for simultaneous neutralization, lightening, pre-pigmentation and dyeing to the desired color.

Classical dyeing should fill these needs, but due to the lack of color concentration, it does not achieve this.

With this diffusion, you can dye over 100% gray hair; dye over 100% of unsmooth hair shaft (highlights, lightened and darkened stripes).

Example. Composition: dye TDL 10.0, 10 g (for loosening gray hair, for example)+dye TDL 6.34, 10 g (for pre-pigmentation of gray hair)+blue-green mixtone, 10 cm (to neutralize the color of natural hair)+desired tone TDL 7.1, 40 g+mixtone magenta, 3 cm (if green will prevail)+orange mixtone, 4 cm (because pre-pigmentation from the dye may not be enough)+oxidizer 110 g+shampoo 30 ml.

In this diffusion, there may also be a black color (TDL 1.0) to add gray and a natural base (brown).

All these types of diffusions help to create colors with 100% getting into the desired color and restore the hair structure at the same time with dyeing.

You can add loosening to the dyeing process itself+pre-pigmentation+neutralization+black+natural black.

Example: dye TDL 12.3, 20 cm+orange mixtone from 1 to 30 cm+blue mixtone from 1 to 30 cm+black TDL 1.0, from 1 cm to 30 cm+dye TDL 7.77 brown from 2 to 30 cm+desired tone TDL 6.0, 30 cm+desired tone TDL 6.1, 30 cm;

or dye TDL 12.3, 20 cm+dye TDL 6.34 from 1 to 30 cm+dye TDL 6.8 (where 8 is blue), from 1 to 30 cm+black TDL 1.0, from 1 cm to 30 cm+dye TDL 7.77 brown from 2 to 30 cm+desired tone TDL 6.1, 30 cm.

Thus, all stages are performed simultaneously. Dyeing can take 30 minutes. At the same time, gray hair does not darken, which is the main problem in beauty salons.

As a rule, after such dyeing, the color refinement mentioned above is important.

In the process of dyeing gray hair, acid diffusion can also be used if the hair was previously dyed in length. The compositions of acid diffusion are provided in Section "Diffusion compositions used in the claimed method", Part 1. The use of acid diffusions is similar to the use in the method according to Option 2.

According to the claimed method, within the first visit of the customer, the procedure for his hair is selected step by step: loosening, pre-pigmentation, dyeing, refinement, etc.

In the subsequent visit, max-mix diffusion is performed for him, adding to it all the recorded indicators from the first visit of the customer, individually selected for this customer and his hair.

The given examples of the method and diffusion compositions are not limiting. They are given only to explain the essence of the invention.

4. Industrial Applicability

The claimed method of hair dyeing and diffusion compositions for its implementation can be applied in beauty salons using well-known dyes to obtain the predicted desired result on hair with a high degree of accuracy, with high dyeing durability and wearability.

REFERENCES CITED

1. RF Patent No. 2679606 Method of gradual hair dyeing (Application No. 2016134428, IPC A61K 8/22, A61K 8/34, A61K 8/44, A61Q 5/10. The patent holder is COMBE INTERNATIONAL LTD. (US). Published 12 Feb. 2019.
2. U.S. Pat. No. 6,758,867 Method of gradual permanent hair dyeing using intermediate dyes based on shampoo (Application US20010034511; IPC:A61K8/34, A61K8/41, A61Q5/02. The applicant is UNILEVER HOME & PERSONAL CARE [US]). Published on 31 Jul. 2003.
3. U.S. Pat. No. 4,104,021 Method of hair dyeing in which the shade depth gradually increases with successive procedures (Application US20010034511; IPC A61K8/00; A61K8/22; A61K8/23; A61K8/33. Applicant: COMBE INC. Published 1 Aug. 1978.
4. RF Patent No. 2308936 (Application No. 2003130278; MPKA61K 8/18, A61Q 5/08, A61Q 5/10. The patent holder is L'AVAN GARD INC (US). Published on 27 Oct. 2007.

What is claimed is:

1. A translucent hair dyeing (THD) method via step-by-step and layer-by-layer application of the components to a hair shaft with mechanical impact and with constant process monitoring, including
    hair preparation for dyeing to obtain the hair shaft aligned along a whole length by quality and color and reduced to a neutral tone, and dyeing with a dye agent diluted with an oxidizer, to obtain a transparency of dye agent layers applied on the hair shaft;
    wherein a hair preparation for dyeing is done using diffusion compositions, being a mixture of components, where a shampoo is used as an active agent;
    wherein dyeing is done using diffusion compositions which are a mixture of components containing at least one oxidative coloring agent and a low concentration oxidizer;
    wherein the hair preparation for dyeing includes the following steps:
    a) a hair cleansing;
    b) a hair shaft alignment by quality and color,
    wherein the hair shaft alignment by quality is done by a hair recovery with a help of active components,
    wherein the hair shaft alignment by color is done by introducing a missing colors into damaged hair sections,
    wherein a lightening background is replenished with pigments of warm shades with a simultaneous hair structure recovery;
    c) the hair shaft alignment by neutralizing a resulting lightening background on the hair with an opposite color to obtain a neutral, gray color, for laying out thea required color on the hair with a predicted result;
    d) applying a color substrate to create a base for the required dye color;
    wherein the dyeing to a desired color includes the following steps:
    e) Applying the composition with a main dye color on the hair as a thin transparent translucent dye layer;
    f) leaving the hair dye composition on the hair;
    g) removing the hair dye composition from the hair after a maturity period;
    h) visual control of a color manifestation;
    i) the hair shaft alignment with color or refinement of a previous result;
    k) repeating a steps sequence, including the Steps d), e), g), h), and i);
    l) a final translucent color application;
    m) as soon as a required result is obtained, the compositions applied are washed off from hair, and the hair is restored.
2. The method according to claim 1 that differs by using diffusion compositions:
    an acid diffusion;
    or a lightening diffusion;
    or a bleaching diffusion;

or a dyeing diffusion;
or a pre-pigmenting diffusion;
or a lightening and pre-pigmenting diffusion;
or a neutralizing diffusion;
or a lightening and neutralizing diffusion;
or a artistic diffusion;
or a max-mix neutralizing, pre-pigmenting, lightening, and dyeing diffusion;
or a diluted diffusion;
or a clay diffusion.

3. The method according to claim 1 that differs by making a lightening after cleansing the hair to obtain a final color lighter than the natural tone, and then the applied composition is removed.

4. The method according to claim 1 that differs by the hair shaft alignment by quality with hair structure recovery is done by applying gelatin, glycerin, amino acids, collagen, and oils.

5. The method according to claim 1 that differs by a color alignment with warm-shade pigments with simultaneous hair structure recovery that is done with pre-pigmenting diffusion.

6. The method according to claim 1 wherein the neutralization of the resulting lightening background is done using a neutralizing diffusion composition comprising a neutralizing dye agent, a mixtone, and 1% to 9% oxidizer.

7. The method according to claim 1 wherein the substrate for creating a base for the required dye color is made using diffusion compositions, while the shampoo is used as an active substance for the substrate base.

8. The method according to claim 1 further comprising introduction into a dyeing diffusion of orange or red mixtones while dyeing a natural hair with darkening; the mixtones correspond to the lightening background, blue or green mixtones to neutralize the background of lightening, a 1% to 3% low concentration oxidizer, and the shampoo.

9. The method according to claim 1 that differs by using a reduced pH composition when dyeing natural hair with a tone-to-tone dyeing diffusion with oxidative dyes.

10. The method according to claim 1 that differs by using a neutralizing or a pre-pigmenting, or an artistic, or a diluted diffusions to adjust the dye color.

11. The method according to claim 1 that differs by achieving the refinement of the dye color by pre-pigmenting water-free diffusions.

12. The method according to claim 1 that differs by application of final translucent color coating using a dilute diffusion composition comprising mixtones, 1% oxidizer, the shampoo, and a mask.

13. The method according to claim 12 that differs by a hair exposure period to the diluted diffusion totaling to 7-25 minutes, while application of a final translucent color is done by constant mechanical impact with hands, with a visual control of color manifestation; a composition removal with water and washing with a shampoo; and completing with a recovery mask with an acidic pH application further on washed off with water.

14. The diffusion composition for hair dyeing comprises:
an acid diffusion comprising: a shampoo and an acid hair color remover proportioned 0.5-3.0 units of a shampoo to 3.0-0.5 units of an acid hair color remover;
a lightening diffusion comprising: a dyeing agent, an oxidizer, the shampoo;
a bleaching diffusion comprising: 1 unit of a lightening powder: 1 unit of the oxidizer to 1 unit of the lightening powder: 200 units of the oxidizer;
a dyeing diffusion comprising: a dyeing agent of Tone Depth Level from 1 to 9, the oxidizer from 1% to 9%, and the shampoo;
or a dyeing agent, 1% to 9% of the oxidizer, amino acids, an oil, a fish oil, or
a dyeing agent+water+liquid amino acids;
a pre-pigmenting diffusion comprising: a warm-shade dyeing agent, a mixtone, the oxidizer, the shampoo, and a mask or
the mixtone, the oxidizer, the shampoo, and the mask,
or a warm-shade dyeing agent, the mixtone, a direct-effect pigment, the oxidizer, the shampoo, and the mask,
or the warm-shade dyeing agent, a warm-shade mixtone, water,
or the warm-shade dyeing agent, a mixtone from orange to fuchsia, the oxidizer, and the shampoo;
a lightening and pre-pigmenting diffusion mix comprising: a dyeing agent, the mixtone, the oxidizer, and the shampoo;
a neutralizing diffusion comprising: a neutralizing effect dyeing agent+the mixtone+1% to 9% of the oxidizer;
a lightening and neutralizing diffusion comprising: a neutralizing effect dyeing agent of Tone Depth Level from 1 to 9, a neutralizing mixtone, blonds of 10, 11, 12, 14 Tone Depth Levels, a 4.5% to 12% oxidizer, and the shampoo;
a artistic diffusion comprising: a mixtone, an oxidizer in the ratio of 1:10; the oxidizer is 1% to 3%;
a maxmix diffusion of neutralizing, pre-pigmenting, lightening, and dyeing effect comprising: a dyeing agent for gray hair mordonsage, a dyeing agent for gray hair pre-pigmentation, a mixtone for natural hair color neutralization, the main tone, mixtones for color alignment or adding, the oxidizer, and the shampoo;
a diluted diffusion comprising: a dyeing agent, the mixtone, the oxidizer, and the shampoo or a dyeing agent and the oxidizer, or the mixtone and the oxidizer;
a diffusion with direct pigments comprising: pigments of direct effect, the oxidizer or an additional oxidative dyeing agent or the shampoo;
a clay diffusion comprising: clay, hot water, and glycerin.

* * * * *